US007595327B2

(12) United States Patent
Levin et al.

(10) Patent No.: US 7,595,327 B2
(45) Date of Patent: Sep. 29, 2009

(54) BETA-SULFONAMIDE HYDROXAMIC ACID INHIBITORS OF TACE/MATRIX METALLOPROTEINASE

(75) Inventors: Jeremy I. Levin, New City, NY (US); Zhong Li, Congers, NY (US); George Diamantidis, Randolph, NJ (US); Frank E. Lovering, Acton, MA (US); Weiheng Wang, Bedford, MA (US); Jeffrey S. Condon, Cambridge, MA (US); Yang-I Lin, Jackson, NJ (US); Jerauld S. Skotnicki, Westfield, NJ (US); Kaapjoo Park, Congers, NY (US)

(73) Assignee: Wyeth, Madison, NJ (US)

( * ) Notice: Subject to any disclaimer, the term of this patent is extended or adjusted under 35 U.S.C. 154(b) by 267 days.

(21) Appl. No.: 11/377,886

(22) Filed: Mar. 16, 2006

(65) Prior Publication Data

US 2006/0211730 A1 Sep. 21, 2006

Related U.S. Application Data

(60) Provisional application No. 60/663,785, filed on Mar. 21, 2005.

(51) Int. Cl.
*A61K 31/44* (2006.01)
*C07D 453/02* (2006.01)
(52) U.S. Cl. .................. 514/306; 514/451; 514/461; 546/134; 546/135; 549/356; 549/362; 549/429
(58) Field of Classification Search .......... 546/134, 546/135; 549/356, 362, 429; 514/306, 451, 514/461
See application file for complete search history.

(56) References Cited

U.S. PATENT DOCUMENTS

| 5,977,408 | A | 11/1999 | Levin et al. |
| 6,365,587 | B1 | 4/2002 | Voss et al. |
| 6,626,516 | B2 | 9/2003 | Tsukuda et al. |

FOREIGN PATENT DOCUMENTS

| EP | 1081137 | 3/2001 |
| WO | WO 98/03166 | 1/1998 |
| WO | WO 99/58528 | 11/1999 |
| WO | WO 00/44723 | 8/2000 |
| WO | WO 01/70673 | 9/2001 |
| WO | WO 03/079986 | 10/2003 |

OTHER PUBLICATIONS

Bauer et al., "Stereospecific Lossen Rearrangements," *J Org Chem* (1959) 24:1293-1296.
Beutler et al., "Tumor necrosis, cachexia, shock, and inflammation: a common mediator," *Ann Rev Biochem* (1988) 57:505-518.
Camussi et al., "The future role of anti-tumour necrosis factor (TNF) products in the treatment of rheumatoid arthritis," *Drugs* (1998) 55(5):613-620.
Cimarelli et al., "An Improved Synthesis of Enantiopure β-Amino Acids," *Synth Commun* (2001) 31(19):2943-2953.
Citterio et al., "α-Hydroxyalkylation of heteroaromatic bases by alcohols and hydroxylamine-O-sulphonic acid," *Tetrahedron* (1985) 41:617-620.
Clements et al., "Matrix metalloproteinase expression during experimental autoimmune encephalomyelitis and effects of a combined matrix metalloproteinase and tumour necrosis factor-alpha inhibitor," *J Neuroimmunol* (1997) 74:85-94.
Colon et al., "Implication of TNF-alpha convertase (TACE/ADAM17) in inducible nitric oxide synthase expression and inflammation in an experimental model of colitis," *Cytokine* (2001) 16:220-226.
Davies et al., "Asymmetric synthesis of (-)-(1R,2S)-cispentacin and related *cis*- and *trans*-2-amino cyclopentane- and cyclohexane-1-carboxylic acids," *J Chem Soc Perkin Trans 1* (1994) Issue No. 11, pp. 1411-1415.
Duffy et al., "The ADAMs family of proteins: from basic studies to potential clinical applications," *Thromb Haemost* (2004) 89:622-631.
Feldman et al., "The role of tumor necrosis factor in the pathophysiology of heart failure," *J Am Coll Cardiol* (2003) 35(3):537-544.
Ferrari et al., "Tumor necrosis factor soluble receptors in patients with various degrees of congestive heart failure," *Circulation* (1995) 92(6):1479-1486.

(Continued)

*Primary Examiner*—Rei-tsang Shiao
(74) *Attorney, Agent, or Firm*—Pepper Hamilton LLP

(57) ABSTRACT

This invention provides compounds of Formula I, having the structure:

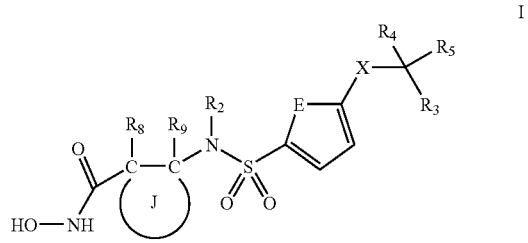

that are useful in treating diseases or disorders mediated by TNF-α, such as arthritis (rheumatoid arthritis (RA), juvenile RA, psoriatic arthritis, osteoarthritis etc), tumor metastasis, tissue ulceration, abnormal wound healing, periodontal disease, bone disease, diabetes (insulin resistance) and HIV infection, ankylosing spondylitis, psoriasis, sepsis, multiple sclerosis, Crohn's disease, degenerative cartilage loss, asthma, idiopathic pulmonary fibrosis, vasculitis, systemic lupus erythematosus, irritable bowel syndrome, acute coronary syndrome, hepatitis C, cachexia, COPD, stroke or type 2 diabetes, and for alleviation of symptoms thereof. The invention further provides methods for use of the compounds.

17 Claims, No Drawings

OTHER PUBLICATIONS

Forro et al., "Lipase-catalyzed enantioselective ring opening of unactivated alicyclic-fused beta-lactams in an organic solvent," *Org Lett* (2003) 5:1209-1212.

Gilchrist et al, "Addition and cycloaddition reactions of the electrophilic vinyl nitroso compounds 3-nitrosobut-3-en-2-one, 2-nitrosopropenal, and ethyl 2-nitrosopropenoate," *J Chem Soc Perkin Trans 1* (1983) Issue No. 1, pp. 1283-1292.

Gilles et al., "Release of TNF-alpha during myocardial reperfusion depends on oxidative stress and is prevented by mast cell stabilizers," *Cardiovascular Res* (2003) 60:608-616.

Grossman et al., "Rheumatoid arthritis: current clinical and research directions," *Women's Health* (1997) 6(6):627-638.

Hallenbeck "The many faces of tumor necrosis factor in stroke," *Nature Medicine* (2002) 8:1363-1368.

Hotamisligil et al., "Adipose expression of tumor necrosis factor-alpha: direct role in obesity-linked insulin resistance," *Science* (1993) 259:87-91.

Hotamisligil et al., "Tumor necrosis factor alpha: a key component of the obesity-diabetes link," *Diabetes* (1994) 43:1271-1278.

Isomaki et al., "Pro- and anti-inflammatory cytokines in rheumatoid arthritis," *J Ann Med* (1997) 29:499-507.

Jin et al., "A continuous fluorimetric assay for tumor necrosis factor-alpha converting enzyme," *Analytical Biochemistry* (2002) 302:269-275.

Kirkegaard et al., "Tumour necrosis factor-alpha converting enzyme (TACE) activity in human colonic epithelial cells," *Clin Exp Immunol* (2004) 135:146-153.

Knight et al., "A novel coumarin-labelled peptide for sensitive continuous assays of the matrix metalloproteinases," *FEBS Lett* (1992) 296:263-266.

Kreuger et al., "Potential of Tumor Necrosis Factor Inhibitors in Psoriasis and Psoriatic Arthritis," *Archives of Dermatology* (2004) 140:218-225.

Kristensen et al., "Localization of tumour necrosis factor-alpha (TNF-alpha) and its receptors in normal and psoriatic skin: epidermal cells express the 55-kD but not the 75-kD TNF receptor," *Clin Exp Immunol* (1993) 94:354-362.

Ksontini et al., "Revisiting the role of tumor necrosis factor alpha and the response to surgical injury and inflammation," *Arch Surg* (1998) 133:558-567.

Levin et al., "The amino acid sequence of a major nonimmunoglobulin component of some amyloid fibrils," *Synth Commun* (2004) 34(15):2773-2776.

Li et al., "Prevalence and significance of mild bleeding disorders in children with recurrent epistaxis," *Synthesis* (1988) 73-76.

Lorenz et al., "Perspectives for TNF-alpha-targeting therapies," *Arthritis Res* (2002) 4(Suppl 3):S17-24.

Lowe "Tumour necrosis factor-α antagonists and their therapeutic applications," *Exp Opin Ther Patents* (1998) 8(10):1309-1322.

Mamoru et al., "Increased expression of tumor necrosis factor-α converting enzyme and tumor necrosis factor-α in peripheral blood mononuclear cells in patients with advanced congestive heart failure," *Eur J Heart Failure* (2004) 6(7):869-875.

Mathison et al., "Participation of tumor necrosis factor in the mediation of gram negative bacterial lipopolysaccharide-induced injury in rabbits," *J Clin Invest* (1988) 81:1925-1937.

Miethke et al., "T cell-mediated lethal shock triggered in mice by the superantigen staphylococcal enterotoxin B: critical role of tumor necrosis factor," *J Exp Med* (1992) 175:91-98.

Meli et al., "In pneumococcal meningitis a novel water-soluble inhibitor of matrix metalloproteinases and TNF-alpha converting enzyme attenuates seizures and injury of the cerebral cortex," *J Neuroimmunology* (2004) 151:6-11.

Morimoto et al., "KB-R7785, a novel matrix metalloproteinase inhibitor, exerts in antidiabetic effect by inhibiting tumor necrosis factor-alpha production," *Life Sci* (1997) 61:795-803.

Moro et al., "Expression and function of tumour necrosis factor-alpha-converting enzyme in the central nervous system," *Neurosignals* (2003) 12:53-58.

Nelson et al., "Matrix metalloproteinases: biologic activity and clinical implications," *J Clin Oncol* (2000) 18(5):1135-49.

Newton et al., "Biology of TACE inhibition," *Ann Rheum Dis* (2001) 60 Suppl 3:iii25-32.

Newton et al., "Therapeutic potential and strategies for inhibiting tumor necrosis factor-alpha," *J Med Chem* (1999) 42(13):2295-314.

Old, "Tumor necrosis factor (TNF).," *Science* (1985) 230(4726):630-2.

Packer "Is tumor necrosis factor an important neurohormonal mechanism in chronic heart failure?," *Circulation* (1995) 92(6):1379-82.

Pallares-Trujillo et al., "TNF and AIDS: two sides of the same coin," *Med Res Reviews* Nov. 1995; 15(6):533-46.

Peterson et al., "Human cytomegalovirus-stimulated peripheral blood mononuclear cells induce HIV-1 replication via a tumor necrosis factor-alpha-mediated mechanism," *J Clin Invest* (1992) 89(2):574-80.

Peterson et al., "Moving beyond disclosure: women's perspectives on barriers and motivators to seeking assistance for intimate partner violence.," *Heart Failure Reviews* (2004) 40(3):9:63-76.

Piguet et al., "Tumor necrosis factor/cachectin is an effector of skin and gut lesions of the acute phase of graft-vs.-host disease.," *J Exp Med* (1987) 166(5):1280-9.

Rankin et al., "The therapeutic effects of an engineered human anti-tumour necrosis factor alpha antibody (CDP571) in rheumatoid arthritis," *J Rheumatol* (1995) 34(4):334-42.

Reimold "TNFa as Therapeutic Target: New Drugs, More Applications," *Drug Targets-Inflammation & Allergy* (2002) 1(4):377-392.

Renkiewicz et al., "Broad-spectrum matrix metalloproteinase inhibitor marimastat-induced musculoskeletal side effects in rats," *Arthritis and Rheumatism* (2003) 48(6):1742-9.

Robertshaw et al., "Release of tumour necrosis factor alpha (TNFalpha) by TNFalpha cleaving enzyme (TACE) in response to septic stimuli in vitro," *Br J Anaesth* (2005) 94(2):222-8.

Rutgeerts et al., "Novel Therapies for Crohn's Disease," *Drugs of Today* (2000) 36(Suppl G):59-68.

Shire et al., "TNF-α inhibitors and rheumatoid arthritis," *Exp. Opin. Ther. Patents* (1998) 8(5):531-544.

Skotnicki et al., "TNF-α Converting Enzyme (TACE) as a Therapeutic Target," *Ann Reports Med Chem* Aug. 2003;110(2):863-8. 38:153.

Spurr et al., "Synthesis of difunctionalized iceane derivatives: 3,13-dimethylene-8-oxapentacyclo[8.3.1.12,6.04,12.06,10]pentadecane," *J Am Chem Soc* (1983) 105(14):4734-4739.

Stajer et al., "Stereochemical Studies. 58. Saturated Heterocycles. 39. Preparation and Steric Structures of Dihydro-1,3-oxazines, 1,3-Oxazin-2-ones and 1,3-Oxazine-2-thiones Fused with Norbornane and Norbornene," *Heterocyclic Chem* (1983) 20:1181-1185.

Tang et al., "Enantioselective hydrogenation of tetrasubstituted olefins of cyclic beta-(acylamino)acrylates," *J Am Chem Soc* (2003) 125(32):9570-9571.

Trifilieff et al., "Pharmacological profile of PKF242-484 and PKF241-466, novel dual inhibitors of TNF-alpha converting enzyme and matrix metalloproteinases, in models of airway inflammation.," *Brit J Pharmacol* (2002 135(7):1655-64.

Van Assche et al., "Anti-TNF agents in Crohn's disease," *Exp. Opin. Invest. Drugs* (2000) 9(1):103-11.

Wang et al., "Inhibition of tumor necrosis factor-alpha-converting enzyme by a selective antagonist protects brain from focal ischemic injury in rats," *Mol Pharmacol* (2004) 65(4):890-6.

Wang et al., "Design, Synthesis, and Structural Analysis of Influenza Neuraminidase Inhibitors Containing Pyrrolidine Cores," *J Med Chem* (2001) 44(8):1192-1201.

Wang et al., "Inhibition of Tumor Necrosis Factor-alpha Convering Enzyme by a Selective Small Molecular Antagonist Protects Brain from Thrombo-Embolic Ischemic Injusry in Rat," *Circulation* (2003) 108(17 Supp):iv-103.

Wendling et al., "Anti-TNF-alpha therapy in ankylosing spondylitis," *Exp Opin Pharmacotherapy* (2004) 5(7):1497-507.

Wolf-Pflugmann et al. "Synthesis and muscarinic activity of a series of tertiary and quaternary N-substituted guvacine esters structurally related to arecoline and arecaidine propargyl ester." *Arzneimittelforschung* (1989) 39(5):539-544.

Zhang et al., "Identification and characterization of 4-[[4-(2-butynyloxy)phenyl]sulfonyl]-N-hydroxy-2,2-dimethyl-(3S)thiomorpholinecarboxamide (TMI-1), a novel dual tumor necrosis factor-alpha-converting enzyme/matrix metalloprotease inhibitor for the treatment of rheumatoid arthritis," *J of Pharmacology and Experimental Therapeutics* (2004) 309(1):348-55. Epub Jan. 12, 2004.:348-355.

*Pharmaprojects* (1996) Therapeutic Updates 17 (Oct.), au197-M2Z.

McGeehan et al., "TNF-alpha in human diseases," *Current Pharmaceutical Design* (1996) 2(6):662-667.

"Bayer and Agouron compete in MMp inhibitor field," *Scrip* (1998) 2349:20.

Higuchi et al., "Pro-drugs as novel delivery systems," *ACS Symposium Series*, vol. 14 (p. 19).

Davies S.G. et al., "Asymmetric synthesis of α-amino carbonyl derivatives using lithium (R)-N-benzyl-N-α-methylbenzamide." *Tetrahedron Asymmetry*, 2002, 13, 1555.

BETA-SULFONAMIDE HYDROXAMIC ACID INHIBITORS OF TACE/MATRIX METALLOPROTEINASE

This application claims benefit of priority to U.S. provisional patent application Ser. No. 60/663,785 filed on Mar. 21, 2005, which is hereby incorporated in its entirety.

FIELD OF THE INVENTION

This invention relates to beta-sulfonamide hydroxamic acid inhibitors of TNF-α converting enzyme (TACE)/matrix metalloproteinases (MMPs). The compounds of the present invention are useful in disease conditions mediated by TNF-α, such as rheumatoid arthritis (RA), juvenile RA, psoriatic arthritis, ankylosing spondylitis, psoriasis, osteoarthritis, tumor metastasis, sepsis, AIDS, ulcerative colitis, multiple sclerosis, diabetes (insulin resistance), Crohn's disease, degenerative cartilage loss, asthma, idiopathic pulmonary fibrosis, vasculitis, systemic lupus erythematosus, irritable bowel syndrome, acute coronary syndrome, hepatitis C, cachexia, COPD, stroke, and type 2 diabetes.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. Exp. Opin. Ther. Patents 1998, 8(5), 531; Grossman, J. M.; Brahn, E. J. Women's Health 1997, 6(6), 627; Isomaki, P.; Punnonen, J. Ann. Med. 1997, 29, 499; Camussi, G.; Lupia, E. Drugs, 1998, 55(5), 613], Crohn's disease [Van Assche, G.; Rutgeerts, P.; Exp. Opin. Invest. Drugs, 2000, 9, 103; Rutgeerts, P.; Baert, F. Drugs of Today, 2000, 36(Suppl. G, Doctor in Focus), 59], psoriatic arthritis [Kreuger, G.; Callis, K.; Archives of Dermatology, 2004, 140, 218], psoriasis [Kristensen, M.; Chu, C. Q.; Eedy, D. J.; et al.; Clin. Exp. Immunol., 1993, 94, 354], vasculitis [Lorenz, H.-M.; Kalden, J. R.; Arthritis Res., 2002, 4(suppl 3), S17], ankylosing spondylitis [Wendling, D.; Toussirot, E.; Exp. Opin. Pharmacotherapy, 2004, 5, 1497], septic shock [Mathison, et. al. J. Clin. Invest. 1988, 81, 1925; Miethke, et al. J. Exp. Med. 1992, 175, 91; Robertshaw, H. J.; Brennan, F. M.; Br. J. Anaesth., 2005, 94, 222], graft rejection [Piguet, P. F.; Grau, G. E.; et al. J. Exp. Med. 1987, 166, 1280], cachexia [Beutler, B.; Cerami, A. Ann. Rev. Biochem. 1988, 57, 505], anorexia, inflammation [Ksontini, R.; MacKay, S. L. D.; Moldawer, L. L. Arch. Surg. 1998, 133, 558], congestive heart failure [Packer, M. Circulation, 1995, 92(6), 1379; Ferrari, R.; Bachetti, T.; et. al. Circulation, 1995, 92(6), 1479; Feldman, A. M.; Combes, A.; Wagner, D,; J. Am. Coll. Cardiol., 2003, 35, 537; Mamoru, S.; Iwasaka, J.; Nakamura, M.; et al.; Eur. J. Heart Failure, 2004, 6, 869], post-ischaemic reperfusion injury [Gilles, S.; Zahler, S.; Welsch, U.; et al.; Cardiovascular Res., 2003, 60, 608], inflammatory disease of the central nervous system [Moro, M. A.; Hurtado, O.; Cardenas, A; et al.; Neurosignals, 2003, 12, 53], inflammatory bowel disease and ulcerative colitis [Colon, A. L.; Menchen, L. A.; Hurtado, O.; De Cristobal, J.; Lizasoain, I.; Leza, J. C.; Lorenzo, P.; Moro, M. A.; Cytokine, 2001, 16, 220; Kirkegaard, T.; Pedersen, G.; Saermark, T.; Brynskov, J.; Clin. Exp. Immunol.; 2004, 135, 146], insulin resistance and diabetes [Hotamisligil, G. S.; Shargill, N. S.; Spiegelman, B. M.; et. al. Science, 1993, 259, 87; Hotamisligil, G. S.; Spiegelman, B. M.; Diabetes, 1994, 43, 1271; Morimoto, Y.; Nishikawa, K.; Ohashi, M. Life Sci., 1997, 61, 795], chronic obstructive pulmonary disease (COPD) and asthma [Trifilieff, A.; Walker, C.; Keller, T.; Kottirsch; Neumann, U.; Brit. J. Pharmacol., 2002, 135, 1655], stroke [Wang, X.; Feuerstein, G. Z.; Xu, L.; et al.; Mol. Pharmacol., 2004, 65, 890; Wang, X.; Xu, L.; Feuerstain, G. Z.; et al. Circulation, 2003, 108 (17 Supp.), iv-103; Hallenback, J. M.; Nature Medicine, 2002, 8, 1363. ], pneumococcal meningitis [Meli, D. N.; Loeffler, J. M.; Baumann, P. et al.; J. Neuroimmunology, 2004, 151, 6], tumor metastasis [Nelson, A. R.; Fingleton, B.; Rothenberg, M. L.; et al.; J. Clin. Oncol., 2000, 18, 1135], multiple sclerosis [Clements, J. M.; Cossins, J. A.; Wells, G. M.; et al.; J. Neuroimmunol., 1997, 74, 85]] and HIV infection [Peterson, P. K.; Gekker, G.; et. al. J. Clin. Invest. 1992, 89, 574; Pallares-Trujillo, J.; Lopez-Soriano, F. J. Argiles, J. M. Med. Res. Reviews, 1995, 15 (6), 533], in addition to its well-documented antitumor properties [Old, L. Science, 1985, 230, 630]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. Br. J. Rheumatol. 1995, 34, 334; Pharmaprojects, 1996, Therapeutic Updates 17 (Oct.), au197-M2Z]. This observation has recently been extended to humans as well ["TNF-α in Human Diseases", Current Pharmaceutical Design, 1996, 2, 662].

Numerous small molecule TACE inhibitors have been disclosed, as reviewed in "TNF-α Converting Enzyme (TACE) as a Therapeutic Target", [Skotnicki, J. S.; Levin, J. I.; Ann. Reports Med. Chem., 2003, 38, 153]. The biology of inhibition of TACE by small molecule inhibitors has also been described [Newton, R. C.; Solomon, K. A.; Covington, M. B.; et al. Ann. Rheum. Dis. 2001, 60, iii25]. In addition the therapeutic potential of inhibitors of TACE has been reviewed [Duffy, M. J.; Lynn, D. J.; Lloyd, A. T.; O'Shea, C. M.; Thromb. Haemost. 2004, 89, 622; Lowe, C.; Exp. Opin. Ther. Patents, 1998, 8, 1309; Newton, R. C.; DeCicco, C. P.; J. Med. Chem. 1999, 42, 2295. Reinhold, A. M.; Curr. Drug Targets-Inflammation & Allergy, 2002, 1, 377]. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) and/or MMP-14 has been postulated to cause joint pain in clinical trials of MMP inhibitors [Scrip, 1998, 2349, 20; Peterson, J. T.; Heart Failure Reviews, 2004, 9, 63; Renkiewicz, R.; Qiu, L.; Lesch, C.; Arthritis and Rheumatism, 2003, 48, 1742]. Selective, orally bioavailable non-peptide inhibitors of TACE would thus be highly desirable for the treatment of the disease states discussed above.

SUMMARY OF THE INVENTION

In some embodiments, the invention provides compounds having the Formula I:

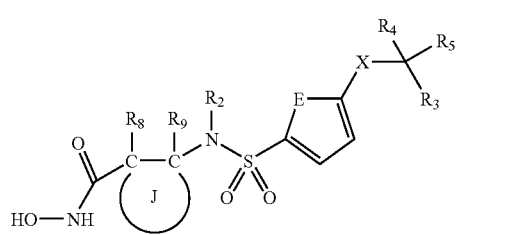

wherein:
J is a monocyclic or bicyclic 5-8 membered cycloalkyl ring optionally containing one double bond; or a monocyclic or bicyclic 5-8 membered heterocycloalkyl ring containing one or two heteroatoms selected from $NR_{31}$, O, and S, and optionally containing one double bond;
   wherein each of said monocyclic or bicyclic 5-8 membered cycloalkyl or heterocycloalkyl ring optionally is substituted with up to four independently selected $R_{14}$ groups;
$R_2$ is hydrogen, $C_1$-$C_6$ alkyl, $C_2$-$C_6$ alkenyl or $C_2$-$C_6$ alkynyl;
   wherein each of said $C_1$-$C_6$ alkyl, $C_2$-$C_6$ alkenyl or $C_2$-$C_6$ alkynyl optionally is substituted with up to four independently selected $R_{14}$ groups;
$R_3$ is naphthyl or bicyclic heteroaryl;
   wherein each of said naphthyl or bicyclic heteroaryl is optionally substituted with up to four independently selected $R_{14}$ groups;
$R_4$ and $R_5$ are each independently hydrogen, $C_1$-$C_6$ alkyl, $C_2$-$C_6$ alkenyl or $C_2$-$C_6$ alkynyl;
   wherein each of said $C_1$-$C_6$ alkyl, $C_2$-$C_6$ alkenyl or $C_2$-$C_6$ alkynyl is optionally substituted with up to four independently selected $R_{15}$ groups;
$R_8$ and $R_9$ are each independently hydrogen, OH, $OR_{17}$, $-OCOR_{12}$, $-OC(O)NR_{12}R_{13}$, $-NR_{12}R_{13}$, $-N(R_{12})COR_{13}$, $-N(R_{20})COOR_{12a}$, $-N(R_{20})SO_2R_{13a}$, $-N(R_{20})CONR_{12}R_{13}$, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ heterocycloalkyl, phenyl, naphthyl or heteroaryl;
   wherein each of said $C_1$-$C_6$ alkyl, $C_2$-$C_6$ alkenyl, $C_2$-$C_6$ alkynyl, $C_1$-$C_6$ alkoxy, $C_3$-$C_8$ cycloalkyl, $C_3$-$C_8$ heterocycloalkyl, phenyl, naphthyl or heteroaryl is optionally substituted with up to four independently selected $R_{16}$ groups;
      each $R_{14}$, $R_{15}$ and $R_{16}$ is independently halogen, $NO_2$, CN, $C_{1-6}$ alkyl, $C_{2-6}$ alkenyl, $C_{2-6}$ alkynyl, $C_{3-8}$ cycloalkyl, $-OR_{17}$, $COR_{12}$, $-OCOR_{12}$, $C_{1-6}$ haloalkyl, $C_{1-6}$-perhaloalkyl, $CONR_{12}R_{13}$, $-S(O)_nR_{13a}$, $-OPO(OR_{12a})OR_{12a}$, $-PO(OR_{12a})R_{13}$, $-OC(O)OR_{12a}$, $-O-C_{1-6}$ alkyl-$NR_{12}R_{13}$, $-OC(O)NR_{12}R_{13}$, $-C(O)NR_{12}OR_{12a}$, $-COOR_{12a}$, $-NR_{12}R_{13}$, $-N(R_{20})-C_{1-6}$ alkyl-$NR_{12}R_{13}$, $-N(R_{12})COR_{13}$, $-N(R_{20})COOR_{12a}$, $-SO_2NR_{12}R_{13}$, $-N(R_{20})SO_2R_{13a}$, $-N(R_{20})CONR_{12}R_{13}$, $-N(R_{20})C(=NR_{13})NR_{12}R_{13}$, $-N(R_{20})C(=NR_{13})N(SO_2R_{13a})R_{13}$, tetrazol-5-yl, $-SO_2NHCN$, $-SO_2NHCONR_{12}R_{13}$, aryl, phenyl, heteroaryl, $C_{3-8}$ heterocycloalkyl, $C_{1-6}$ alkyl$-OR_{22}$, $-C_{1-6}$ alkyl $-SR_{22}$, $-C(=NR_{13})-$, $CSR_{12}$, or $-C(=NR_{13})NR_{12}R_{13}$;
      each $R_{12}$ and $R_{13}$ is, independently, H, $OR_{12a}$, $C_{1-6}$ alkyl, $C_{2-6}$ alkenyl, $C_{2-6}$ alkynyl, $C_{1-6}$ haloalkyl, $C_{1-6}$ perhaloalkyl, $C_{3-8}$ cycloalkyl, aryl, heteroaryl, $C_{1-6}$ alkoxy, $C_{2-6}$ alkenyloxy, $C_{2-6}$ alkynyloxy, $C_{1-6}$ haloalkoxy, $C_{1-6}$ perhaloalkoxy, aralkyl, or $C_{3-8}$ heterocycloalkyl; or $-NR_{12}R_{13}$ may form a pyrrolidine, piperidine, morpholine, thiomorpholine, oxazolidine, thiazolidine, pyrazolidine, piperazine, or azetidine ring, wherein one nitrogen atom of a pyrazolidine or piperazine ring can optionally bear a $R_{13a}$, $-COR_{12a}$, $-COOR_{13a}$, $-SO_2R_{13a}$, or $-CONR_{12}R_{13}$ group;
      each $R_{12a}$ is, independently, H, $C_{1-6}$ alkyl, $C_{2-6}$ alkenyl, $C_{2-6}$ alkynyl, $C_{1-6}$ haloalkyl, $C_{1-8}$ perfluoroalkyl, $C_{3-8}$ cycloalkyl, aryl, heteroaryl, , aralkyl, or $C_{3-8}$ heterocycloalkyl;
      each $R_{13a}$ is, independently, H, OH, $C_{1-6}$ alkyl, $C_{2-6}$ alkenyl, $C_{2-6}$ alkynyl, $C_{1-6}$ haloalkyl, $C_{1-6}$ perfluoroalkyl, $C_{3-8}$ cycloalkyl, $C_{1-6}$ alkoxy, $C_{2-6}$ alkenyloxy, $C_{2-6}$ alkynyloxy, aryl, heteroaryl, aralkyl, or $C_{3-8}$ heterocycloalkyl;
      each $R_{20}$ is independently H or $C_{1-6}$ alkyl;
      each $R_{17}$ is, independently, H, $C_{1-6}$ alkyl, $C_{2-6}$ alkenyl, $C_{2-6}$ alkynyl, $C_{1-6}$ haloalkyl, $C_{1-6}$ perhaloalkyl, $C_{3-8}$ cycloalkyl, aryl, heteroaryl, , aralkyl or $C_{3-8}$ heterocycloalkyl;
      each $R_{22}$ is independently H or $C_{1-3}$ alkyl;
      E is $-C=C-$, $-C=N-$, $-N=C-$, S or O;
      X is O, $S(O)_n$, or $NR_{12}$;
      n is 0, 1 or 2; and
$R_{31}$ is H, $C_1$-$C_6$ alkyl, $C_2$-$C_6$ alkenyl, $C_2$-$C_6$ alkynyl, $C_1$-$C_6$ perhaloalkyl, aryl, heteroaryl, aralkyl, $C_{3-8}$ cycloalkyl, $C_{3-8}$ heterocycloalkyl, $-COR_{12}$, $-COOR_{12a}$, $-SO_2R_{12a}$, $-SO_2NR_{12}R_{13}$, or $CONR_{12}R_{13}$, where said $C_1$-$C_6$ alkyl, $C_2$-$C_6$ alkenyl, $C_2$-$C_6$ alkynyl, aryl, heteroaryl, aralkyl, $C_{3-8}$ cycloalkyl, and $C_{3-8}$ heterocycloalkyl, are each optionally substituted with up to four independently selected $R_{14}$ groups;
or a pharmaceutically acceptable salt thereof.

In some embodiments, J is a monocyclic or bicyclic 5-8 membered cycloalkyl ring optionally containing one double bond and optionally substituted with up to four independently selected $R_{14}$ groups.

In some embodiments, J is a monocyclic or bicyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, J is a monocyclic 5-8 membered cycloalkyl ring optionally containing one double bond and optionally substituted with up to four independently selected $R_{14}$ groups; or a monocyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, J is a bicyclic 5-8 membered cycloalkyl ring optionally containing one double bond and optionally substituted with up to four independently selected $R_{14}$ groups; or a bicyclic 5-8 membered heterocycloalkyl ring containing one or two heteroatoms selected from $NR_{31}$, O, and S, optionally containing one double bond and optionally substituted with up to four independently selected $R_{14}$ groups.

Also provided in accordance with the present invention are pharmaceutically acceptable salts, and prodrugs, of the compounds disclosed herein.

DETAILED DESCRIPTION

In some embodiments, the invention provides compounds having the Formula I:

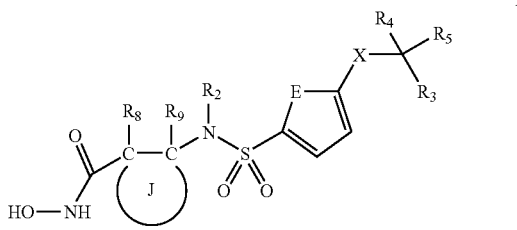

wherein:
J is a monocyclic or bicyclic 5-8 membered cycloalkyl ring optionally containing one double bond; or a monocyclic or bicyclic 5-8 membered heterocycloalkyl ring containing one or two heteroatoms selected from $NR_{31}$, O, and S, and optionally containing one double bond;
wherein each of said monocyclic or bicyclic 5-8 membered cycloalkyl or heterocycloalkyl ring optionally is substituted with up to four independently selected $R_{14}$ groups;

$R_2$ is hydrogen, $C_1$-$C_6$ alkyl, $C_2$-$C_6$ alkenyl or $C_2$-$C_6$ alkynyl;
wherein each of said $C_1$-$C_6$ alkyl, $C_2$-$C_6$ alkenyl or $C_2$-$C_6$ alkynyl optionally is substituted with up to four independently selected $R_{14}$ groups;

$R_3$ is naphthyl or bicyclic heteroaryl;
wherein each of said naphthyl or bicyclic heteroaryl is optionally substituted with up to four independently selected $R_{14}$ groups;

$R_4$ and $R_5$ are each independently hydrogen, $C_1$-$C_6$ alkyl, $C_2$-$C_6$ alkenyl or $C_2$-$C_6$ alkynyl;
wherein each of said $C_1$-$C_6$ alkyl, $C_2$-$C_6$ alkenyl or $C_2$-$C_6$ alkynyl is optionally substituted with up to four independently selected $R_{15}$ groups;

$R_8$ and $R_9$ are each independently hydrogen, OH, $OR_{17}$, —$OCOR_{12}$, —$OC(O)NR_{12}R_{13}$, —$NR_{12}R_{13}$, —$N(R_{12})COR_{13}$, —$N(R_{20})COOR_{12a}$, —$N(R_{20})SO_2R_{13a}$, —$N(R_{20})CONR_{12}R_{13}$, halogen, $C_1$-$C_6$ alkyl, $C_2$-$C_6$ alkenyl, $C_2$-$C_6$ alkynyl, $C_3$-$C_8$ cycloalkyl, $C_3$-$C_8$ heterocycloalkyl, phenyl, naphthyl or heteroaryl;
wherein each of said $C_1$-$C_6$ alkyl, $C_2$-$C_6$ alkenyl, $C_2$-$C_6$ alkynyl, $C_1$-$C_6$ alkoxy, $C_3$-$C_8$ cycloalkyl, $C_3$-$C_8$ heterocycloalkyl, phenyl, naphthyl or heteroaryl is optionally substituted with up to four independently selected $R_{16}$ groups;

each $R_{14}$, $R_{15}$ and $R_{16}$ is independently halogen, $NO_2$, CN, $C_{1-6}$ alkyl, $C_{2-6}$ alkenyl, $C_{2-6}$ alkynyl, $C_{3-8}$ cycloalkyl, —$OR_{17}$, $COR_{12}$, —$OCOR_{12}$, $C_{1-6}$ haloalkyl, $C_{1-6}$ perhaloalkyl, $CONR_{12}R_{13}$, —$S(O)_nR_{13a}$ —$OPO(OR_{12a})OR_{12a}$, —$PO(OR_{12a})R_{13}$, —$OC(O)OR_{12a}$, —O—$C_{1-6}$ alkyl-$NR_{12}R_{13}$, —$OC(O)NR_{12}R_{13}$, —$C(O)NR_{12}OR_{12a}$, —$COOR_{12a}$, —$NR_{12}R_{13}$, —$N(R_{20})$—$C_{1-6}$ alkyl-$NR_{12}R_{13}$, —$N(R_{12})COR_{13}$, —$N(R_{20})COOR_{12a}$, —$SO_2NR_{12}R_{13}$, —$N(R_{20})SO_2R_{13a}$, —$N(R_{20})CONR_{12}R_{13}$, —$N(R_{20})C(=NR_{13})NR_{12}R_{13}$, —$N(R_{20})C(=NR_{13})N(SO_2R_{13a})R_{13}$, tetrazol-5-yl, —$SO_2NHCN$, —$SO_2NHCONR_{12}R_{13}$, aryl, phenyl, heteroaryl, $C_{3-8}$ heterocycloalkyl, $C_{1-6}$ alkyl—$OR_{22}$, —$C_{1-6}$ alkyl —$SR_{22}$, —$C(=NR_{13})$—, $CSR_{12}$, or —$C(=NR_{13})NR_{12}R_{13}$;

each $R_{12}$ and $R_{13}$ is, independently, H, $OR_{12a}$, $C_{1-6}$ alkyl, $C_{2-6}$ alkenyl, $C_{2-6}$ alkynyl, $C_{1-6}$ haloalkyl, $C_{1-6}$ perhaloalkyl, $C_{3-8}$ cycloalkyl, aryl, heteroaryl, $C_{1-6}$ alkoxy, $C_{2-6}$ alkenyloxy, $C_{2-6}$ alkynyloxy, $C_{1-6}$ haloalkoxy, $C_{1-6}$ perhaloalkoxy, , aralkyl, or $C_{3-8}$ heterocycloalkyl; or —$NR_{12}R_{13}$ may form a pyrrolidine, piperidine, morpholine, thiomorpholine, oxazolidine, thiazolidine, pyrazolidine, piperazine, or azetidine ring, wherein one nitrogen atom of a pyrazolidine or piperazine ring can optionally bear a $R_{13a}$, —$COR_{12a}$, —$COOR_{13a}$, —$SO_2R_{13a}$, or —$CONR_{12}R_{13}$ group;

each $R_{12a}$ is, independently, H, $C_{1-6}$ alkyl, $C_{2-6}$ alkenyl, $C_{2-6}$ alkynyl, $C_{1-6}$ haloalkyl, $C_{1-8}$ perfluoroalkyl, $C_{3-8}$ cycloalkyl, aryl, heteroaryl, aralkyl, or $C_{3-8}$ heterocycloalkyl;

each $R_{13a}$ is, independently, H, OH, $C_{1-6}$ alkyl, $C_{2-6}$ alkenyl, $C_{2-6}$ alkynyl, $C_{1-6}$ haloalkyl, $C_{1-6}$ perfluoroalkyl, $C_{3-8}$ cycloalkyl, $C_{1-6}$ alkoxy, $C_{2-6}$ alkenyloxy, $C_{2-6}$ alkynyloxy, aryl, heteroaryl, aralkyl, or $C_{3-8}$ heterocycloalkyl;

each $R_{20}$ is independently H or $C_{1-6}$ alkyl;
each $R_{17}$ is, independently, H, $C_{1-6}$ alkyl, $C_{2-6}$ alkenyl, $C_{2-6}$ alkynyl, $C_{1-6}$ haloalkyl, $C_{1-6}$ perhaloalkyl, $C_{3-8}$ cycloalkyl, aryl, heteroaryl, aralkyl or $C_{3-8}$ heterocycloalkyl;

each $R_{22}$ is independently H or $C_{1-3}$ alkyl;
E is —C=C—, —C=N—, —N=C—, S or O;

X is O, $S(O)_n$, or $NR_{12}$;
n is 0, 1 or 2; and
$R_{31}$ is H, $C_1$-$C_6$ alkyl, $C_2$-$C_6$ alkenyl, $C_2$-$C_6$ alkynyl, $C_1$-$C_6$ perhaloalkyl, aryl, heteroaryl, aralkyl, $C_{3-8}$ cycloalkyl, $C_{3-8}$ heterocycloalkyl, —$COR_{12}$, —$COOR_{12a}$, —$SO_2R_{12a}$, —$SO_2NR_{12}R_{13}$, or $CONR_{12}R_{13}$, where said $C_1$-$C_6$ alkyl, $C_2$-$C_6$ alkenyl, $C_2$-$C_6$ alkynyl, aryl, heteroaryl, aralkyl, $C_{3-8}$ cycloalkyl, and $C_{3-8}$ heterocycloalkyl, are each optionally substituted with up to four independently selected $R_{14}$ groups;

or a pharmaceutically acceptable salt thereof.

In some embodiments, J is a monocyclic or bicyclic 5-8 membered cycloalkyl ring optionally containing one double bond and optionally substituted with up to four independently selected $R_{14}$ groups.

In some embodiments, J is a monocyclic or bicyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, J is a monocyclic 5-8 membered cycloalkyl ring optionally containing one double bond and optionally substituted with up to four independently selected $R_{14}$ groups; or a monocyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, J is a bicyclic 5-8 membered cycloalkyl ring optionally containing one double bond and optionally substituted with up to four independently selected $R_{14}$ groups; or a bicyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, at least one of $R_8$ and $R_9$ is other than hydrogen.

In some embodiments, ring J has the formula:

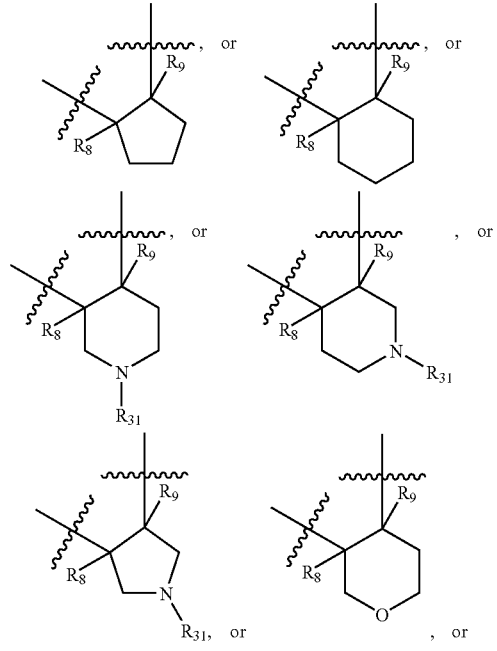

-continued

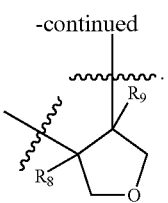

In some such embodiments, at least one of $R_8$ and $R_9$ is selected from $C_{1-6}$ alkyl, $OR_{17}$ and halogen, wherein said $C_1$-$C_6$ alkyl optionally is substituted with up to four independently selected $R_{14}$ groups.

In some further such embodiments, at least one of $R_8$ and $R_9$ is selected from methyl, ethyl, $CH_2OH$, OH and fluorine.

In some further such embodiments, $R_3$ is a bicyclic heteroaryl comprising a phenyl ring fused to a heteroaryl ring, said bicyclic heteroaryl being optionally substituted with up to four independently selected $R_{14}$ groups.

In some embodiments, $R_{31}$ is selected from H, COH, CO—$C_{1-6}$ alkyl, COO—$C_{1-6}$ alkyl, $C_{1-6}$ alkyl, $C_{2-6}$ alkynyl, $CONR_{12}R_{13}$, and $SO_2$—$C_{1-6}$ alkyl.

In still further embodiments, $R_2$ is hydrogen or $C_1$-$C_6$ alkyl, $R_4$ and $R_5$ are each hydrogen, E is —C≡C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl.

In some further embodiments, $R_2$, $R_4$ and $R_5$ are each hydrogen, E is —C≡C—, X is oxygen, and $R_3$ is 2-methylquinoline-4-yl. In some such embodiments, the sulfonamide and hydroxamate substituents attached to ring J occupy cis-positions relative to each other. In some such embodiments, at least one of $R_8$ and $R_9$ is selected from $C_{1-6}$ alkyl, $OR_{17}$ and halogen, wherein said $C_1$-$C_6$ alkyl optionally is substituted with up to four independently selected $R_{16}$ groups. In some further embodiments, at least one of $R_8$ and $R_9$ is selected from methyl, ethyl, $CH_2OH$, OH and fluorine.

The $R_{31}$ substituent can be any as defined above. However, in some preferred embodiments, $R_{31}$ is selected from H, COH, CO—$C_{1-6}$ alkyl, COO—$C_{1-6}$ alkyl, $C_{1-6}$ alkyl optionally substituted with OH, $C_{2-6}$ alkynyl, $CONR_{12}R_{13}$, and $SO_2$—$C_{1-6}$ alkyl. Some preferred $R_{31}$ groups include $SO_2CH_3$, $SO_2CH(CH_3)_2$, —$CH(CH_3)_2$, $CH_2C\equiv H$, —$CH_2CH_2OH$, $COCH_3$, COH, $COOC(CH_3)_3$, CONH—$CH_2$—$CH_3$, $CONHC(CH_3)_3$ and $CONHCH_3$.

In some embodiments, J is a bicyclic 5-8 membered cycloalkyl ring optionally containing one double bond and optionally substituted with up to four independently selected $R_{14}$ groups. In some such embodiments, ring J has the formula:

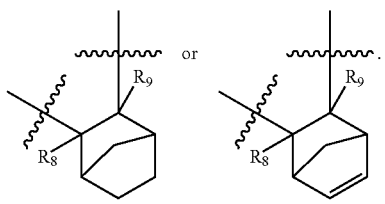

In some such embodiments, $R_3$ is a bicyclic heteroaryl comprising a phenyl ring fused to a heteroaryl ring, said bicyclic heteroaryl being optionally substituted with up to four independently selected $R_{14}$ groups.

In some further embodiments, $R^2$ is hydrogen or $C_1$-$C_6$ alkyl, E is —C≡C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl.

In some further embodiments, $R_2$, $R_4$ and $R_5$ are each hydrogen, E is —C≡C—, X is oxygen, and $R_3$ is 2-methylquinoline-4-yl. In some such embodiments, the sulfonamide and hydroxamate substituents attached to ring J occupy cis-positions relative to each other.

In some embodiments, J is a bicyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, J is a bicyclic 5-8 membered heterocycloalkyl ring containing one or two ring $NR_{31}$ groups. In some such embodiments, ring J has the formula:

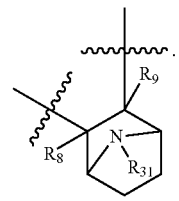

In some such embodiments, $R_3$ is a bicyclic heteroaryl comprising a phenyl ring fused to a heteroaryl ring, said bicyclic heteroaryl being optionally substituted with up to four independently selected $R_{14}$ groups. In some further such embodiments, $R_2$ is hydrogen or $C_1$-$C_6$ alkyl, $R_4$ and $R_5$ are each hydrogen, E is —C≡C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl. In some further such embodiments, $R_2$, $R_4$, and $R_5$ are each hydrogen, E is —C≡C—, X is oxygen, and $R_3$ is 2-methylquinoline-4-yl. In some further such embodiments, the sulfonamide and hydroxamate substituents attached to ring J occupy cis-positions relative to each other.

In some further embodiments, $R_{31}$ is selected from H, $C_{1-6}$ alkyl, $C_{2-6}$ alkenyl, $C_{2-6}$ alkynyl, $COR_{12}$, $COOR_{12a}$, $CONR_{12}R_{13}$, and $S(O)_nR_{13a}$. In some such embodiments, $R_{31}$ is selected from $SO_2CH_3$, $SO_2CH(CH_3)_2$, $CH(CH_3)_2$, $CH_2C\equiv H$, $COCH_3$, COH, $COOC(CH_3)_3$, $CONHCH_2CH_3$, $CONHC(CH_3)_3$ and $CONHCH_3$.

In some embodiments, J is a bicyclic 5-8 membered heterocycloalkyl ring containing one ring O atom optionally containing one double bond and optionally substituted with up to four independently selected $R_{14}$ groups. In some such embodiments, ring J has the formula:

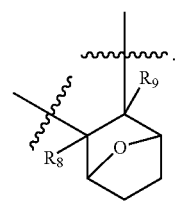

In some such embodiments, $R_3$ is a bicyclic heteroaryl comprising a phenyl ring fused to a heteroaryl ring, said bicyclic heteroaryl being optionally substituted with up to four independently selected $R_{14}$ groups. In some further such embodiments, $R_2$ is hydrogen or $C_1$-$C_6$ alkyl, $R_4$ and $R_5$ are each hydrogen, E is —C═C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl. In some further such embodiments, $R_2$, $R_4$ and $R_5$ are each hydrogen, E is —C═C—, X is oxygen, and $R_3$ is 2-methylquinoline-4-yl. In some further such embodiments, the sulfonamide and hydroxamate substituents attached to ring J occupy cis-positions relative to each other.

In some embodiments, J is a bicyclic 5-8 membered heterocycloalkyl ring containing one ring S atom optionally containing one double bond and optionally substituted with up to four independently selected $R_{14}$ groups.

In some embodiments, J is a monocyclic 5-8 membered cycloalkyl ring optionally containing one double bond and optionally substituted with up to four independently selected $R_{14}$ groups. In some embodiments, J is a monocyclic 5 or 6 membered cycloalkyl ring optionally containing one double bond and optionally substituted with up to four independently selected $R_{14}$ groups. In some such embodiments, ring J has the formula:

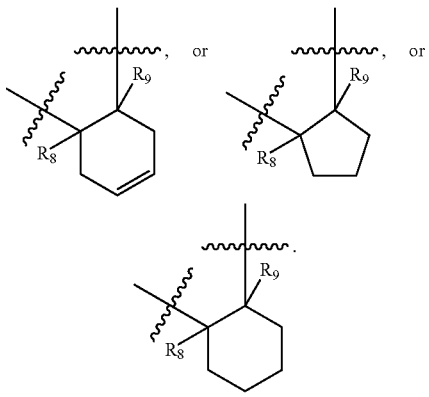

In some such embodiments, $R_3$ is a bicyclic heteroaryl comprising a phenyl ring fused to a heteroaryl ring, said bicyclic heteroaryl being optionally substituted with up to four independently selected $R_{14}$ groups. In some further such embodiments, $R_2$ is hydrogen or $C_1$-$C_6$ alkyl, E is —C═C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl. In some further such embodiments, $R_2$, $R_4$ and $R_5$ are each is hydrogen, E is —C═C—, X is oxygen, and $R_3$ is 2-methylquinoline-4-yl. In some further such embodiments, the sulfonamide and hydroxamate substituents attached to ring J occupy cis-positions relative to each other.

In some embodiments, J is a monocyclic 5-8 membered heterocycloalkyl ring containing one or two heteroatoms selected from $NR_{31}$, O, and S, optionally containing one double bond and optionally substituted with up to four independently selected $R_{14}$ groups.

In some embodiments, J is a monocyclic 5-8 membered heterocycloalkyl ring containing one or two ring $NR_{31}$ groups, further optionally containing one double bond and further optionally substituted with up to four independently selected $R_{14}$ groups.

In some embodiments, J is a monocyclic 5 or 6 membered heterocycloalkyl ring containing one ring $NR_{31}$ group and optionally containing one double bond and optionally substituted with up to four independently selected $R_{14}$ groups.

In some embodiments, ring J has the formula:

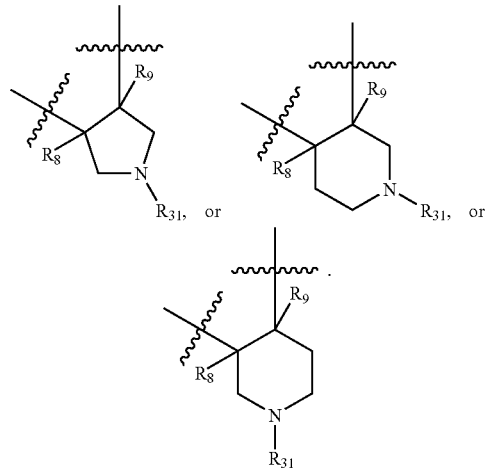

In some such embodiments, $R_3$ is a bicyclic heteroaryl comprising a phenyl ring fused to a heteroaryl ring, said bicyclic heteroaryl being optionally substituted with up to four independently selected $R_{14}$ groups. In some further such embodiments, $R_2$ is hydrogen or $C_1$-$C_6$ alkyl, E is —C═C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl. In some further such embodiments, $R_2$, $R_4$ and $R_5$ are each hydrogen, E is —C═C—, X is oxygen, and $R_3$ is 2-methylquinoline-4-yl. In some further such embodiments, the sulfonamide and hydroxamate substituents attached to ring J occupy cis-positions relative to each other. In some further such embodiments, $R_{31}$ is selected from H, $C_{1-6}$ alkyl, $C_{2-6}$ alkenyl, $C_{2-6}$ alkynyl, $COR_{12}$, $COOR_{12a}$, $CONR_{12}R_{13}$, and $S(O)_nR_{13a}$. In some further such embodiments, $R_{31}$ is selected from $SO_2CH_3$, $SO_2CH(CH_3)_2$, $CH(CH_3)_2$, $CH_2C\equiv H$, $COCH_3$, $COH$, $COOC(CH_3)_3$, $CONHCH_2CH_3$, $CONHC(CH_3)_3$ and $CONHCH_3$.

In some embodiments, J is a monocyclic 5-8 membered heterocycloalkyl ring containing one or two ring O atoms optionally containing one double bond and optionally substituted with up to four independently selected $R_{14}$ groups.

In some embodiments, J is a monocyclic 5 or 6 membered heterocycloalkyl ring containing one ring O atom optionally containing one double bond and optionally substituted with up to four independently selected $R_{14}$ groups.

In some embodiments, ring J has the formula:

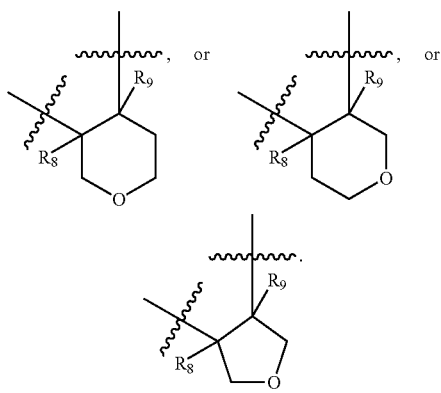

In some such embodiments, $R_3$ is a bicyclic heteroaryl comprising a phenyl ring fused to a heteroaryl ring, said bicyclic heteroaryl being optionally substituted with up to four independently selected $R_{14}$ groups. In some further such embodiments, $R_2$ is hydrogen or $C_1$-$C_6$ alkyl, E is —C═C—, X is oxygen, and $R_3$ is 2-methylquinoline-4-yl, 1-H-1,2,3-benzotriazol-1-yl, 1-H-benzimidazol-5-yl, or 2,1,3-benzoxadiazol-5-yl. In some further such embodiments, $R_2$, $R_4$ and $R_5$ are each hydrogen, E is —C═C—, X is oxygen, and $R_3$ is 2-methylquinoline-4-yl. In some such embodiments, the sulfonamide and hydroxamate substituents attached to ring J occupy cis-positions relative to each other.

In some embodiments, J is a monocyclic 5-8 membered heterocycloalkyl ring containing one ring S atom optionally containing one double bond and optionally substituted with up to four independently selected $R_{14}$ groups.

In some embodiments, J is a monocyclic 5 or 6 membered heterocycloalkyl ring containing one ring S atom optionally containing one double bond and optionally substituted with up to four independently selected $R_{14}$ groups.

In some embodiments of the compounds of Formula I, $R_2$ is hydrogen or $C_{1-6}$ alkyl. In some embodiments of the compounds of Formula I, E is —C═C—. In some further embodiments of the compounds of Formula I, X is oxygen. In still further embodiments of the compounds of Formula I, $R_3$ is a bicyclic heteroaryl optionally substituted with up to four independently selected $R_{14}$ groups. In some such embodiments, the bicyclic heteroaryl comprises a phenyl ring fused to a heteroaryl ring.

In some embodiments of the compounds of Formula I, $R_3$ is quinoline optionally substituted with up to four independently selected $R_{14}$ groups. In some such embodiments, $R_3$ is quinoline substituted with methyl. In some such embodiments, $R_3$ is 2-methylquinoline-4-yl.

In some embodiments of the compounds of Formula I, $R_2$ is hydrogen or $C_1$-$C_6$ alkyl, E is —C═C—, X is oxygen, and $R_3$ is 2-methylquinoline-4-yl. In some further embodiments of the compounds of Formula I, $R_2$ is hydrogen or methyl, and $R_4$ and $R_5$ are each hydrogen. In some further embodiments of the compounds of Formula I, $R_2$, $R_4$ and $R_5$ are each hydrogen, E is —C═C—, X is oxygen, and $R_3$ is 2-methylquinoline-4-yl. In some such embodiments, the sulfonamide and hydroxamate substituents attached to ring J occupy cis-positions relative to each other. In some such embodiments, $R_3$ is 2-methylquinoline-4-yl, 1-H-1,2,3-benzotriazol-1-yl, 1-H-benzimidazol-5-yl, or 2,1,3-benzoxadiazol-5-yl.

In some embodiments of the compounds of Formula I, the compounds have the absolute stereochemistry shown in Formula II:

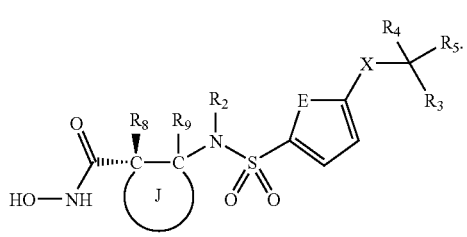

II

In some embodiments of the compounds of Formula I, the compounds have the absolute stereochemistry shown in Formula III:

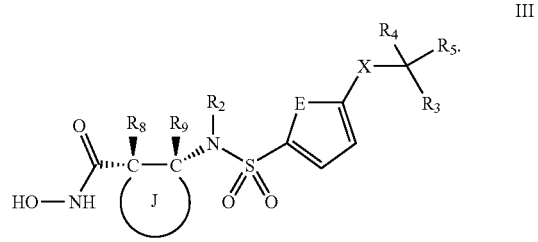

III

Also provided in accordance with the present invention are pharmaceutically acceptable salts, and prodrugs, of the compounds disclosed herein.

The compounds of the present invention are useful for the treatment of disease conditions mediated by TNF-α, such as rheumatoid arthritis (RA), juvenile RA, psoriatic arthritis, ankylosing spondylitis, psoriasis, osteoarthritis, tumor metastasis, sepsis, AIDS, ulcerative colitis, multiple sclerosis, diabetes (insulin resistance), Crohn's disease, degenerative cartilage loss, asthma, idiopathic pulmonary fibrosis, vasculitis, systemic lupus erythematosus, irritable bowel syndrome, acute coronary syndrome, hepatitis C, cachexia, COPD, and type 2 diabetes and for the alleviation of symptoms thereof. Accordingly, the present invention further provides methods of treating these diseases and disorders using the compounds described herein. In some embodiments, the methods include identifying a mammal having a disease or disorder mediated by TNF-α, and providing to the mammal an effective amount of a compound as described herein.

In further embodiments, the methods are provided for alleviating a symptom of a disease or disorder mediated by TNF-α. In some embodiments, the methods include identifying a mammal having a symptom of a disease or disorder mediated by TNF-α, and providing to the mammal an amount of a compound as described herein effective to ameliorate (i.e., lessen the severity of) the symptom.

Pharmaceutically acceptable salts of the compounds of Formula (I) having an acidic moiety can be formed from organic and inorganic bases. Suitable salts with bases are, for example, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

The present invention also includes prodrugs of the compounds described herein. As used herein, "prodrug" refers to a moiety that releases a compound of the invention when administered to a mammalian subject. Prodrugs can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a mammalian subject, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, s-butyl, t-butyl), pentyl (e.g., n-pentyl, isopentyl, neopentyl) and the like. Alkyl groups can contain from 1 to about 20, 1 to about 10, 1 to about 8, 1 to about 6, 1 to about 4, or 1 to about 3 carbon atoms. In some embodiments, alkyl groups can be substituted with up to four independently selected $R_{14}$ groups, as described herein. As used herein, the term "lower alkyl" is intended to mean alkyl groups having up to six carbon atoms.

As used herein, "alkenyl" refers to an alkyl group having one or more double carbon-carbon bonds. Example alkenyl groups include ethenyl, propenyl, butenyl, pentenyl, hexenyl, butadienyl, pentadienyl, hexadienyl, and the like. In some embodiments, alkenyl groups can be substituted with up to four independently selected $R_{14}$ groups, as described herein.

As used herein, "alkynyl" refers to an alkyl group having one or more triple carbon-carbon bonds. Examples of alkynyl groups include ethynyl, propynyl, butynyl, pentynyl, and the like. In some embodiments, alkynyl groups can be substituted with up to four independently selected $R_{14}$ groups, as described herein.

As used herein, "cycloalkyl" refers to non-aromatic carbocyclic groups including cyclized alkyl, alkenyl, and alkynyl groups. Cycloalkyl groups can be monocyclic (e.g., cyclohexyl) or poly-cyclic (e.g. 2, 3, or 4 fused ring, bridged, or spiro monovalent saturated hydrocarbon moiety), wherein the carbon atoms are located inside or outside of the ring system. Any suitable ring position of the cycloalkyl moiety may be covalently linked to the defined chemical structure. Examples of cycloalkyl groups include cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcarnyl, adamantyl, spiro[4.5]deanyl, homologs, isomers, and the like. Also included in the definition of cycloalkyl are moieties that have one or more aromatic rings fused (i.e., having a bond in common with) to the cycloalkyl ring, for example, benzo derivatives of cyclopentane (indanyl), cyclohexane (tetrahydronaphthyl), and the like. In some embodiments, cycloalkyl groups can be substituted with up to four independently selected $R_{14}$ groups, as described herein.

As used herein, "hydroxy" or "hydroxyl" refers to OH.

As used herein, "halo" or "halogen" includes fluoro, chloro, bromo, and iodo.

As used herein, "cyano" refers to CN.

As used herein, "alkoxy" refers to an —O-alkyl group. Example alkoxy groups include methoxy, ethoxy, propoxy (e.g., n-propoxy and isopropoxy), t-butoxy, and the like. An alkoxy group can contain from 1 to about 20, 1 to about 10, 1 to about 8, 1 to about 6, 1 to about 4, or 1 to about 3 carbon atoms. In some embodiments, alkoxy groups can be substituted with up to four independently selected $R_{14}$ groups, as described herein.

As used herein, "alkenyloxy" refers to an —O-alkenyl group. Examples of alkenyloxy groups include prop-3-enyloxy, but-2-enyloxy, but-3-enyloxy, pent-2-enyloxy, 2-methyl-pent-3-enyloxy and the like. Alkenyloxy groups can contain from 2 to about 20, 2 to about 10, 2 to about 8, 2 to about 6, 2 to about 4, or 2 to about 3 carbon atoms. In some embodiments, alkenyloxy groups can be substituted with up to four independently selected $R_{14}$ groups, as described herein.

As used herein, "alkynyloxy" refers to an —O-alkynyl group. Examples of alkenyloxy groups include prop-3-ynyloxy, but-2-ynyloxy, but-3-ynyloxy, pent-2-ynyloxy, 2-methyl-pent-3-ynyloxy and the like. Alkynyloxy groups can contain from 2 to about 20, 2 to about 10, 2 to about 8, 2 to about 6, 2 to about 4, or 2 to about 3 carbon atoms. In some embodiments, alkynyloxy groups can be substituted with up to four independently selected $R_{14}$ groups, as described herein.

As used herein, "haloalkyl" refers to an alkyl group having one or more halogen substituents. Examples of haloalkyl groups include $CF_3$, $C_2F_5$, $CHF_2$, $CCl_3$, $CHCl_2$, $C_2Cl_5$, and the like. An alkyl group in which all of the hydrogen atoms are replaced with halogen atoms can be referred to as "perhaloalkyl." Examples perhaloalkyl groups include perfluoroalkyl groups (e.g., $CF_3$ and $C_2F_5$).

As used herein, "haloalkoxy" refers to an —O-haloalkyl group, and "perhaloalkoxy" refers to an —O-perhaloalkyl group.

As used herein, "aryl" refers to aromatic carbocyclic groups including monocyclic or polycyclic aromatic hydrocarbons such as, for example, phenyl, 1-naphthyl, 2-naphthyl anthracenyl, phenanthrenyl, and the like. In some embodiments, aryl groups have from 6 to about 20 carbon atoms. In some preferred embodiments, aryl groups are phenyl or naphthyl groups that optionally contain up to four, preferably up to 2, independently selected $R_{14}$ groups as described herein.

As used herein, "heteroaryl" is intended to refer to monocyclic or polycyclic aromatic ring systems having from 5 to 10 ring atoms and containing 1-3 ring heteroatoms selected from O, N and S. In some embodiments, one or more ring nitrogen atoms can bear a substituent as described herein. In some preferred embodiments, heteroaryl groups are 5-6 member aromatic heterocyclic rings containing 1-3 hetero ring atoms selected from O, N and S. Examples of heteroaryl groups include, without limitation, the following:

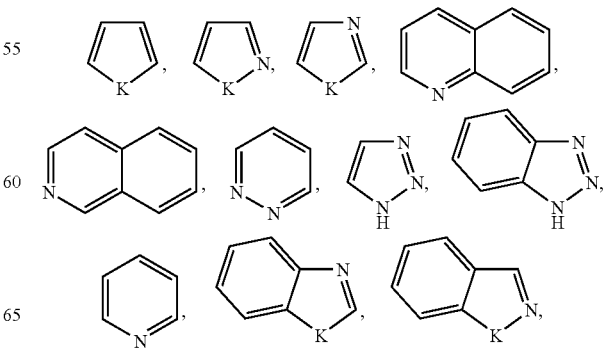

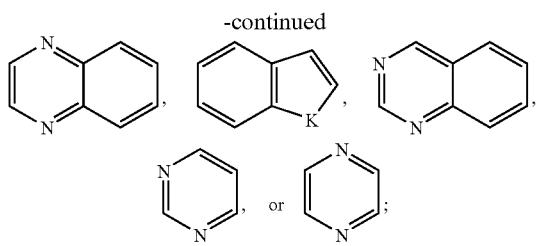

wherein K is defined as O, S, N or $NR_{31}$. Examples of heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, 2-methylquinoline-4-yl, 1-H-1,2,3-benzotriazol-1-yl, 1-H-benzimidazol-5-yl, 2,1,3-benzoxadiazol-5-yl and benzoxazole. In some embodiments, heteroaryl groups can be substituted with up to four, preferably up to two, independently selected $R_{14}$ groups as described herein.

As used herein, "bicyclic heteroaryl" refers to bicyclic aromatic ring systems having from 8 to 12 ring atoms and containing 1-3 ring heteroatoms selected from O, N and S, with the proviso that the bicyclic heteroaryl ring does not contain O—O, S—S, or S—O bonds. In some embodiments, one or more ring nitrogen atoms can bear a substituent as described herein. Bicyclic heteroaryl groups include any of the monocyclic heteroaryl rings described herein fused to a phenyl ring. The bicyclic heteroaryl group may be attached to its pendant group at any heteroatom or carbon atom that results in a stable structure. Bicyclic heteroaryl groups may be substituted by up to four independently selected $R_{14}$ groups as described herein.

Examples of bicyclic heteroaryl groups include, but are not limited to, benzimidazolyl, benzofuranyl, benzothiofuranyl, benzothiophenyl, benzoxazolyl, benzthiazolyl, benztriazolyl, benztetrazolyl, benzo[c]isoxazolyl, benzo[d]isoxazolyl, benzo[c]isothiazolyl, benzo[d]isothiazolyl, cinnolinyl, 1H-indazolyl, 2H-indazolyl, indolizinyl, indolyl, isobenzofuranyl, isoindolyl, isoquinolinyl, naphthyridinyl, phthalazinyl, pteridinyl, purinyl, oxazolopyridinyl, thiazolopyridinyl, imidazopyridinyl, furopyridinyl, thienopyridinyl, pyridopyrimidine, pyridopyrazine, pyridopyridazine, quinazolinyl, quinolinyl, quinoxalinyl, thienothiazolyl, thienoxazolyl, and thienoimidazolyl.

As used herein, "aryloxy" refers to an —O-aryl group, for example and not limitation, phenoxy. In some embodiments, aryloxy groups optionally contain up to four, preferably up to 2, independently selected $R_{14}$ groups as described herein.

As used herein, "arylalkyl" or "aralkyl" refers to a group of formula -alkyl-aryl. Preferably, the alkyl portion of the arylalkyl group is a lower alkyl group, i.e., a $C_{1-6}$ alkyl group, more preferably a $C_{1-3}$ alkyl group. Examples of aralkyl groups include benzyl and naphthylmethyl groups. In some embodiments, arylalkyl groups can be optionally substituted with up to four, preferably up to 2, independently selected $R_{14}$ groups as described herein.

As used herein, "heteroarylalkyl" or "heteroaralkyl" refers to a group of formula -alkyl-heteroaryl. Nonlimiting examples of heteroaralkyl groups include pyridylmethyl and pyrrolemethyl groups. In some embodiments, heteroarylalkyl groups can be substituted with up to four, preferably up to 2, independently selected $R_{14}$ groups as described herein.

As used herein, "heterocycloalkyl" refers to a non-aromatic cycloalkyl group that contains at least one ring heteroatom (i.e., non-carbon atom), preferably selected from O, N and S, and optionally contains one or more double or triple bonds. Examples of heterocycloalkyl groups include morpholine, pyran, piperidine piperazine, and the like. In some embodiments, heterocycloalkyl groups can be optionally substituted with up to four, preferably up to 2, independently selected $R_{14}$ groups as described herein. In some embodiments, nitrogen atoms of heterocycloalkyl groups can bear a substituent, for example a $R_{12}$ or $R_{13}$ group, as described herein. Also included in the definition of heterocycloalkyl are moieties that have one or more aromatic rings fused (i.e., having a bond in common with) to the heterocycloalkyl ring, for example, benzimidazolinyl, chromanyl, chromenyl, indolinetetrahydorquinolinyl, and the like.

At various places in the present specification substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, propyl, isopropyl, n-butyl, sec-butyl, isobutyl, etc.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The compounds of the present invention can contain an asymmetric atom (also referred as a chiral center), and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

The compounds of present invention can be conveniently prepared in accordance with the procedures outlined in the schemes below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatograpy (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Although not wishing to be limited to any source, publications and literatures such as WO 200044723; Li, J. P.; Newlander, K. A.; Yellin, T. O. *Synthesis*, 1988, 73-76; Gilchrist, T. L.; Roberts, T. G. *J. Chem. Soc. Perkin. Trans* 1 1983, 1283-1292 are useful and recognized references of organic synthesis known to those in the art. Each of the foregoing is incorporated herein by reference in its entirety.

General Schemes for the Preparation of the Present Invention Compounds

The invention compounds are prepared using conventional techniques known to those skilled in the art of organic synthesis. The starting materials used in preparing the compounds of the invention are known, made by known methods or are commercially available. Some of the starting materials and intermediates, and methods for making starting materials and intermediates are described in EP1081137 A1, W003/079986 A2, W09958528, W001/70673 A2, U.S. Pat. Nos. 5,977,408, 6,365,587 and 6,326,516 and literature [(a) Bauer, L.; Miarka, S. V. *J. Org. Chem.* 1959, 24, 1293-1296; (b) Stajer, G.; Szabo, E. A.; Fulop, F.; Bernath, G.; Sohar, P. *J. Heterocyclic Chem.*, 1983, 20, 1181-1185; (c) Citterio, A.; Gentile, A.; Minisce, F.; Serravalle, M.; Ventura, S. *Tetrahedron*, 1985, 41, 617-620. ], each of which is incorporated herein in its entirety.

Those skilled in the art of organic synthesis will recognize that the nature and order of the synthetic steps presented may be varied for the purpose of optimizing the formation of the compounds of the invention.

The compounds of this invention may be prepared form the precursors shown in Scheme 1. For example, O-protected hydroxamic acid 2, where the protecting group R is a t-butyl moiety, may be converted into hydroxamic acid 1 by the reaction with trifluoroacetic acid between room temperature and 50° C. Other suitable protecting groups R include, tetrahydropyran, Boc, and benzyl, for example. The protected hydroxamic acids 2 are available by the reaction of carboxylic acids 3 with the appropriate O-substituted hydroxylamine, such as O-(tert-butyl)hydroxylamine, in the presence of a peptide coupling reagent such as benzotriazol-1-yloxy-tris (dimethylamino)-phosphonium hexafluorophosphate (BOP), and a tertiary amine such as N,N-diisopropylethylamine (Hunig's base) in a polar aprotic solvent such as DMF at a temperature between 0° C. and 50° C. Alternatively, protected hydroxamic acids 2 are available by reaction of esters 4 with the appropriate O-substituted hydroxylamine and trimethylaluminum or other Lewis acid. Hydroxamic acids 1 are also available from the carboxylic acids 3 by reaction with pepetide coupling reagents, for example with 1-hydroxybenzotriazole in the presence of 1-(3-dimethylaminopropyl)-3-ethylcarbodiimide in DMF, followed by reaction with 50% aqueous hydroxylamine. Alternatively, carboxylic acids 3 can be converted into the corresponding acid chloride by reaction with oxalyl chloride and DMF, followed by reaction with hydroxylamine to provide hydroxamates 1. Carboxylic acids 3 can be prepared from the corresponding esters 4 via acid hydrolysis with hydrogen chloride or trifluoroacetic acid when R' is a tert-butyl group. Acid hydrolysis with aqueous hydrochloric acid or basic hydrolysis with aqueous sodium hydroxide can also be used to convert esters 4 into carboxylates 3. Esters 4 may be converted directly into hydroxamic acids 1 by reacting the ester with hydroxylamine in the presence of methanolic potassium hydroxide (Feiser & Feiser, *Reagents for Organic Synthesis*, Volume 1, p.478).

SCHEME 1

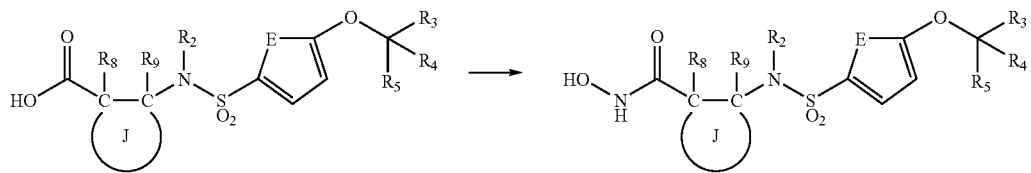

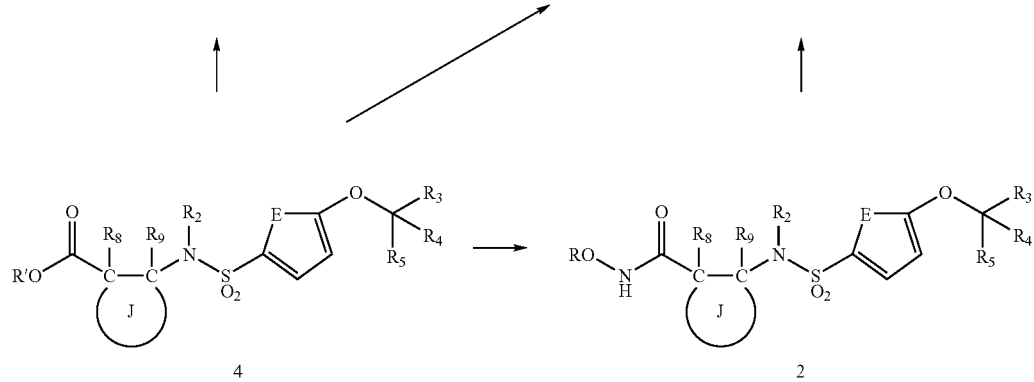

Carboxylic acids 3 may also be prepared according to the method in Scheme 2. Reaction of the desired β-amino acid 5 with sulfonyl chloride 6 in the presence of pyridine or a tertiary amine base such as triethylamine, or N-methylmorpholine, provides carboxylates 3 directly. The β-amino acid 5 and sulfonyl chloride 6 may also be reacted under Schotten-Baumann conditions using aqueous sodium bicarbonate solution and dichloromethane. Furthermore, β-amino acid 5 may first be reacted with bis(trimethylsilyl)trifluoroacetamide in dichloromethane at reflux temperature, followed by reaction with the desired sulfonyl chloride in the presence of base such as N-methylmorpholine at room temperature overnight, to give sulfonamide carboxylic acids 3 in high yield. As shown in Scheme 1, carboxylates 3 can be prepared from ester 4. As shown in Scheme 2, esters 4 are available from the reaction of β-amino esters 9 with 4-benzyloxy-benzenesulfonyl chloride 10 (prepared, for example, by a procedure described in WO 98/03166) to give sulfonamide-ester 8. Hydrogenation of 8 over palladium on carbon then affords phenol 7 which may then be alkylated with the desired alkyl halide, mesylate, tosylate, or triflate, such as 4-chloromethyl-2-methyl-quinoline (prepared from thionyl chloride and (2-methyl-quinolin-4-yl)-methanol [*Tet.*, 1985, 41, 617-620]) in a polar aprotic solvent such as DMF, between room temperature and 50° C., using a base such as potassium carbonate or cesium carbonate (for R$_2$=hydrogen) to give esters 4. Compounds 8, wherein both R and R$_2$ are equal to hydrogen may also be dialkylated with an alkyl halide such as iodomethane in the presence of a base such as potassium carbonate in a solvent such as DMF to give N-alkyl sulfonamide esters of general structure 8. Alternatively, β-amino esters 9 may be directly sulfonylated with 4-hydroxybenzenesulfonyl chloride (Levin, et al. *Synth. Commun.* 2004, 34(15) 2773) to afford sulfonamide-ester 7. In yet another route to esters 4, β-amino esters 9 may be reacted with sulfonyl chlorides 6, such as 4-(2-methyl-quinolin-4-ylmethoxy)-benzenesulfonyl chloride (prepared from 4-chloromethyl-2-methylquinoline 7 by the procedure described in W003/079986), in the presence of a tertiary amine base or under Schotten-Baumann conditions, to give 4 directly.

SCHEME 2

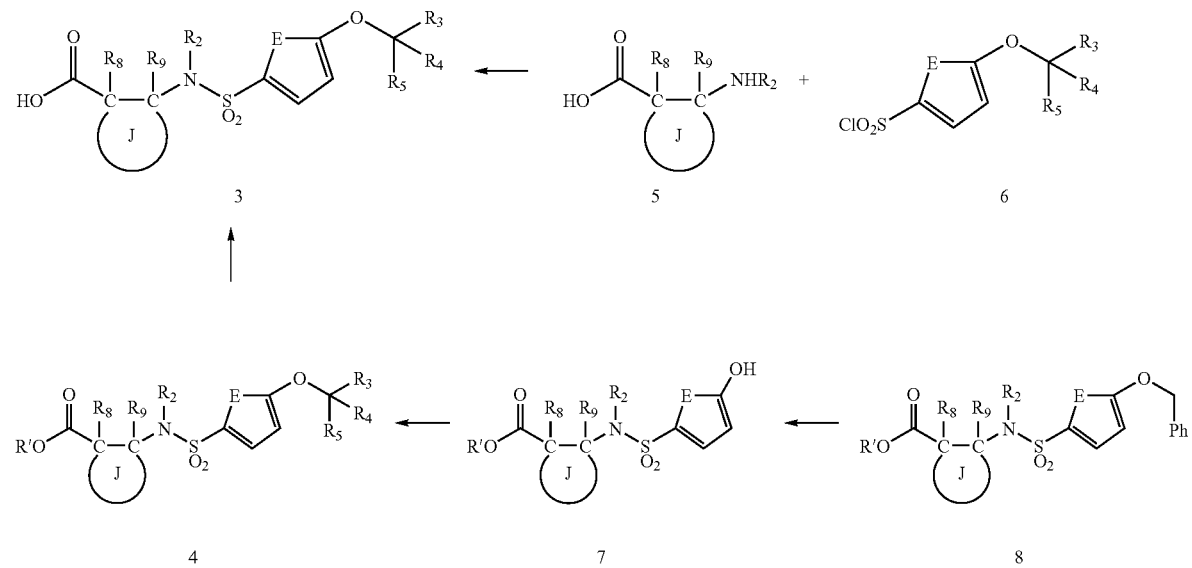

-continued

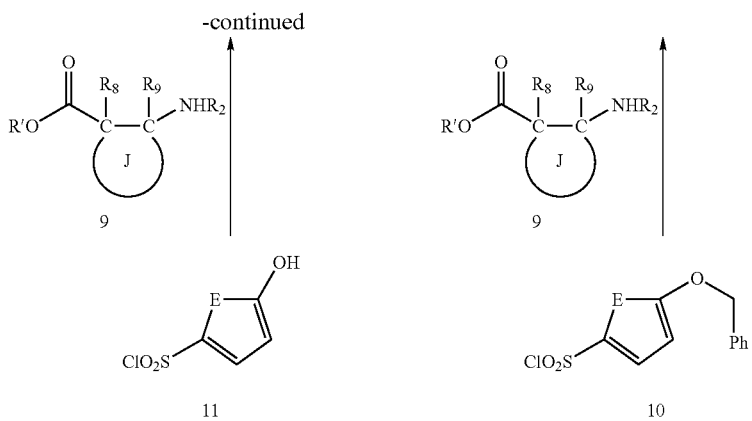

Carboxylic acids 3, wherein $R_2$ is other than hydrogen may be prepared as Shown in Schemes 3 and 4. Thus, as shown in Scheme 3, β-amino acid 5 ($R_2$=H) reacts with sulfonyl chloride 10 to give the sulfonamide-acid 12. Arylsulfonamide carboxylic acid 12 is then reacted with DMF di-tert-butyl acetal in a mixture of toluene and DMF at reflux temperature to give tert-butyl ester 13. Alkylation of 13 with an alkyl iodide such as iodomethane, or an alkyl chloride, in DMF in the presence of a base such as potassium carbonate then provides 14. Debenzylation of 14 by transfer hydrogenation with cyclohexadiene or hydrogenation with hydrogen at 30-45 psi in the presence of palladium on carbon gives phenol 7. Alkylation of 7 analogously to Scheme 2, for example with 4-chloromethyl-2-methyl-quinoline, in DMF in the presence of potassium carbonate, followed by removal of the t-butyl group with hydrogen chloride gas or trifluoroacetic acid affords carboxylates 3.

Synthetic routes to sulfonamide esters 4 wherein $R_2$ is other than hydrogen are shown in Scheme 4. Reaction of β-amino esters 9 with sulfonyl chloride 6, for example 4-(2-methyl-quinolin-4-ylmethoxy)-benzenesulfonyl chloride gives sulfonamide esters 15. Alkylation of 15 with an alkyl iodide such as iodomethane, or an alkyl chloride, in DMF in the presence of a base such as potassium carbonate then provides 4. In the same manner, reaction of β-amino esters 9 with sulfonyl chloride 10, gives sulfonamide ester 12, which is then alkylated with an alkyl iodide such as iodomethane, or an alkyl chloride, in DMF in the presence of a base such as potassium carbonate to give 8. Removal of the benzyl group of 8 via hydrogenolysis, followed by alkylation of the resulting phenol with an alkyl halide such as 4-chloromethyl-2-methyl-quinoline, as described in Scheme 2, provides the desired sulfonamide esters 4.

SCHEME 3

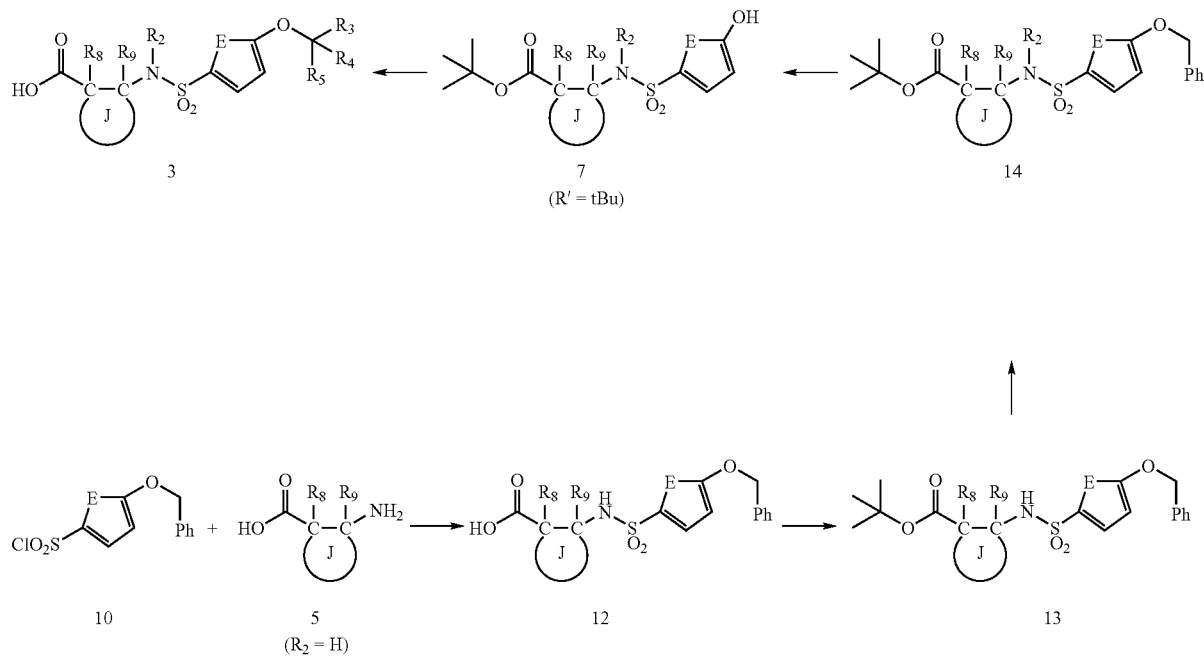

SCHEME 4

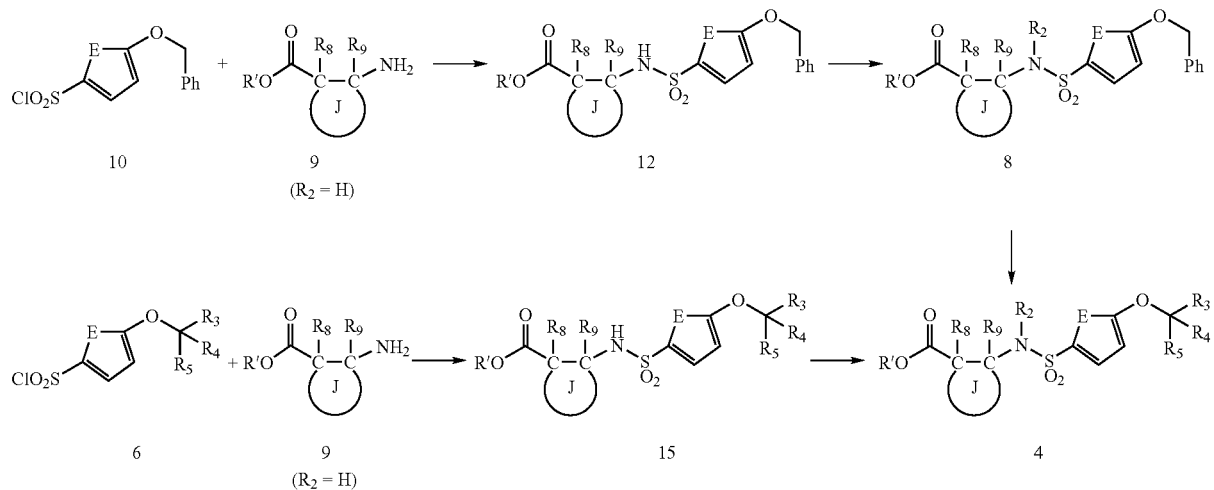

Although the foregoing examples include compounds wherein X is oxygen, it is to be understood that the invention encompasses compounds wherein X is S or $NR_{12}$. Using known synthetic methods in combination with the methods described above, one skilled in the art could synthesize compounds wherein X is S or $NR_{12}$.

The desired β-amino acid groups of the invention may be synthesized according to a variety of literature methods (see for example "Enantioselective Synthesis of β-Amino Acids", E. Juaristi, E d. Wiley-VCH, 1997). As shown in Scheme 5 the readily available β-keto esters 16 can be reacted with amines, such as benzylamine and α-methylbenzylamine, optimally in the presence of ytterbium(III)triflate or similar Lewis acid, to give the enamino-esters 17. The double bond of 17 is then reduced with a hydride reducing agent such as sodium triacetoxyborohydride or sodium cyanoborohydride, or hydrogenated over palladium on carbon, or in the presence of another suitable catalyst, to give β-amino esters 9. A similar method, affording enantiopure material, is disclosed by C. Cimarelli, et al, in Synth. Commun. 2001, 31, 2943-2953. If desired, the group $R_2$ of compounds 9 may be removed prior to reaction with a sulfonyl chloride; for example when $R_2$ is a benzyl or substituted benzyl moiety, hydrogenolysis over palladium on carbon provides β-amino esters 9 with a primary amino group (i.e. $R_2$=H). A similar route that provides enantiomerically pure β-amino acids of structure 5 has been reported with analogs of enamino-ester 17. Thus, compounds of structure 17 wherein $R_2$ is an acetyl or Boc group can be hydrogenated in the presence of a chiral catalyst to provide enantiopure β-amino acids 5 useful as intermediates for the invention (W. Tang, et al., J. Am. Chem. Soc., 2003, 125, 9570-9571).

SCHEME 5

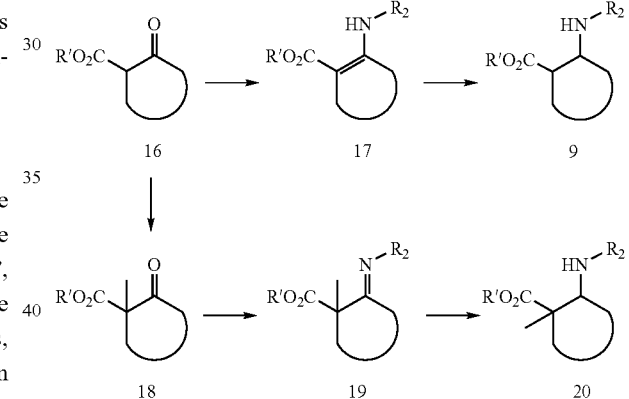

Alpha-substituted β-amino esters 20 are also available from keto-esters 16 as shown in Scheme 5. For example, alkylation of keto-ester 16 with an alkyl halide, triflate, mesylate or tosylate, such as iodomethane in a polar aprotic solvent such as DMF in the presence of a base such as sodium hydride at 0° C. to room temperature gives the α-substituted keto-ester 18. Reaction of keto-ester 18 with an amine such as α-methylbenzylamine in the presence of ytterbium(III)triflate or similar Lewis acid, with the removal of water using for example Dean-stark conditions, affords an imine 19. Compounds 19 can be reduced with a hydride reducing agent such as sodium triacetoxyborohydride or sodium cyanoborohydride, or hydrogenated over palladium on carbon, or in the presence of another suitable catalyst, to give α-substituted β-amino esters 20. Where necessary the $R_2$ group of these α-substituted β-amino esters 20 can be removed, for example by hydrogenation of an α-methylbenzyl $R_2$ group, prior to sufonylation and conversion into the compounds of the invention.

Another literature method that provides intermediate β-amino acids of structure 5 for the invention via enzymatic kinetic resolution of bet-lactam products of [2+2] cycloadditions of chlorosulfonyl isocyanate and cyclic alkenes, such as cyclopentene, is disclosed by E. Forro, et al, in Org. Lett. 2003, 5, 1209-1212. Scheme 6 illustrates the synthesis of one particular β-amino acid, 2-aminocyclopentanecarboxylic acid, using this procedure. β-amino acids having different ring sizes can be synthesized in a similar manner.

Another method for the synthesis of intermediate β-amino acids of structure 5 is disclosed by Davies, et al, in *J. Chem. Soc. Perkin Trans.* I, 1994, 1411 (Scheme 7). Thus, lithium (R)-N-benzyl-N-α-methylbenzylamide reacts with α, β-unsaturated esters (as shown for cyclopentene 2-butyl ester) to afford a Michael adduct in high diastereomeric excess. Hydrogenation of the two N-benzyl groups then provides the enantiopure, β-amino acids of structure 21. A modification of this route is also useful for providing α-substituted β-amino esters and acids. Thus, addition of lithium (R)-N-benzyl-N-α-methylbenzylamide followed by quenching of the resulting ester enolate with (1R)-(−)-(10-camphorsulfonyl)oxaziridine provides the α-hydroxy ester 22. Similarly, quenching the enolate with an alkyl halide, such as iodomethane or iodoethane provides the corresponding α-alkyl, ester 23, using N-fluorobenzene sulfonamide provides the α-fluoro ester 24, and quenching with an aldehyde such as formaldehyde provides the α-hydroxyalkyl ester 25. Hydrogenation of the N-benzyl groups then yields the desired primary amino functionality (26, 27, 28, and 29, respectively). It is understood by those skilled in the art that when this route is applied to the synthesis of heterocyclic β-amino esters, such as piperidine or pyrrolidine β-amino esters, protecting groups may be required on the heteroatom of the heterocyclic ring. In this respect the N-suberyl group, available via alkylation of the heterocyclic amine with 5-chlorodibenzosuberane, is preferable. It is understood by those skilled in the art that protecting groups may be removed or interchanged at any point in the synthesis.

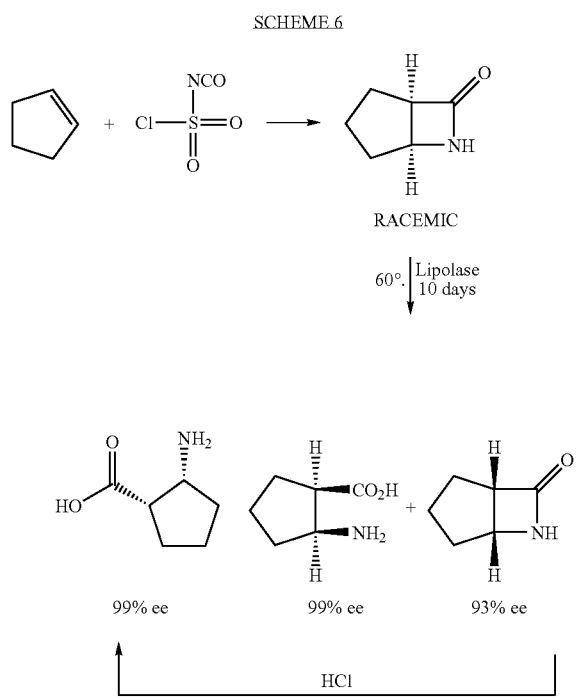

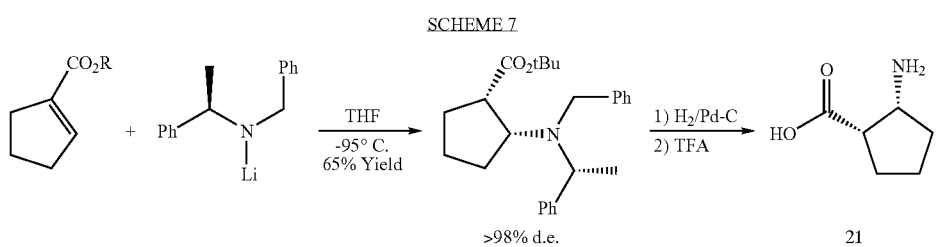

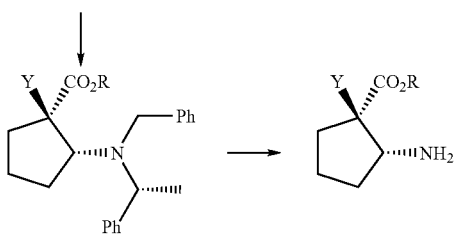

Beta-substituted β-amino esters of structure 9 are available from the [2+2] cycloaddition of chlorosulfonyl isocyanate with cycloalkenyl or heterocyclo-alkenyl precursors bearing one exocyclic substiuent on the olefin. For example, treatment of cycloalkene 30 (e.g. 1-methyl-1-cyclohexene) with chlorosulfonyl isocyanate affords the substituted β-lactam 31, as shown in Scheme 8 (following the procedure of Spurr et al, *J. Am. Chem. Soc.*, 1983, 105, 4735). Reaction of the β-lactam 31 with trimethylsilyl chloride in methanol then affords the ring opened methyl ester 32, suitable for sulfonylation.

SCHEME 8

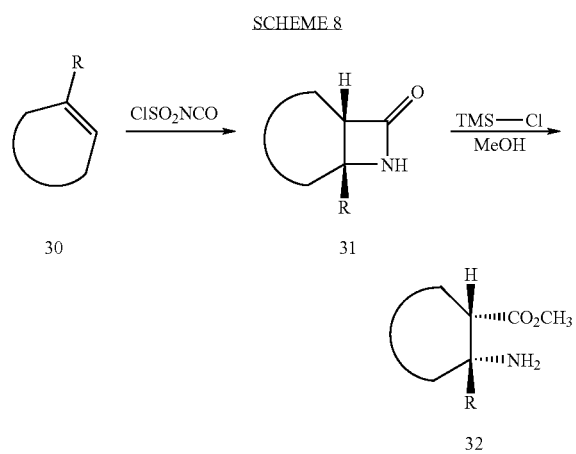

The compounds of this invention may be also prepared by the epimerization of cis-sulfonamide esters (i.e. compounds of structure 4, wherein $R_1$ is cis-substituted) with sodium methoxide in methanol at reflux temperature overnight to provide the corresponding trans-isomers.

EXAMPLES

Preparation of Compounds of the Invention

The following describes the preparation of representative compounds of this invention in greater detail. The following examples are offered for illustrative purposes, and are not intended to limit the invention in any manner. Those of skill in the art will readily recognize a variety of noncritical parameters which can be changed or modified to yield essentially the same results.

Mass spectral data is reported as the mass-to-charge ratio, m/z; and for high resolution mass spectral data, the calculated and experimentally found masses, [M+H]+, for the neutral formulae M are reported. Nuclear magnetic resonance data is reported as δ in parts per million (ppm) downfield from the standard, tetramethylsilane; along with the solvent, nucleus, and field strength parameters. The spin-spin homonuclear coupling constants are reported as J values in hertz; and the multiplicities are reported as a: s, singlet; d, doublet; t, triplet; q, quartet; quintet; or br, broadened.

The following compounds were prepared using the procedures of Schemes 1-8 described above.

Exemplary Syntheses of Compounds of the Invention

Example 1 exo-N-Hydroxy-3-[methyl({4-[(2-methylquinolin-4-yl)methoxy]phenyl}sulfonyl)amino]bicyclo[2.2.1]heptane-2-carboxamide

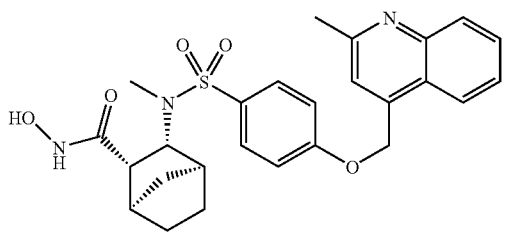

Step 1

To a solution of 8.32 g (54.3 mmol) of sulfur trioxide N,N-dimethylformamide complex in 10 mL of dichloromethane was added a solution of 10 g (54.3 mmol) of benzyl phenyl ether in 15 mL of dichloromethane. The reaction mixture was refluxed for 1 h and cooled to room temperature. Thionyl chloride (4.31 mL, 59 mmol) was added to the reaction mixture. The resulting reaction mixture was heated at 75° C. for 2 h. After cooling, the volatile materials were removed under reduced pressure. The residue was dissolved in 250 mL of ethyl acetate, washed with 15 mL of saturated sodium bicarbonate solution and 15 mL of saturated sodium chloride solution and dried over sodium sulfate. After filtration, the ethyl acetate was removed under reduced pressure. The residue was triturated with hexane to give 7.5 g of 4-benzyloxybenzenesulfonyl chloride as colorless crystals.

Step 2

To a suspension of 1.55 g (10 mmol) of 3-exo-aminobicyclo[2.2.1]heptane-2-exo-carboxylic acid in 25 mL of dichloromethane under nitrogen was added 5.32 mL (20 mmol) of bis(trimethylsilyl)trifluoroacetamide. The resulting mixture was stirred under nitrogen at reflux temperature for 1 h and then cooled with an ice-bath. To the stirred reaction mixture was added a solution of 2.83 g of 4-benzyloxybenzenesulfonyl chloride in 15 mL of dichloromethane and 1.43 mL of N-methylmorpholine. The resulting mixture was stirred at room temperature overnight and diluted with 30 mL of dichloromethane. To the mixture was added 15 mL of water and the aqueous layer was adjusted to pH 1 with 1N HCl solution. After stirring the mixture for 15 min, the desired product precipitated. The colorless solid was collected by filtration, washed with a small volume of cold water and dried under reduced pressure to give 3.48 g of exo-3-({[4-(benzyloxy)phenyl]sulfonyl}amino)bicyclo[2.2.1]heptane-2-carboxylic acid as colorless crystals.

Electrospray Mass Spec 400.2 (M−H)−.

Step 3

To 3.44 g of the product from Step 2 was added 30 mL of toluene and 11 mL of N,N-dimethylformamide di-tert-butyl acetal. The resulting mixture was heated at 110° C. for 4.5 h under nitrogen. The volatile materials were removed under reduced pressure. The residue was triturated with ethyl acetate to give 1.28 g of tert-butyl exo-3-({[4-(Benzyloxy)

phenyl]sulfonyl}amino)bicyclo[2.2.1]heptane-2-carboxylate as a colorless solid.

Electrospray Mass Spec 456.2 (M–H)⁻.

Step 4

To a solution of 1.28 g of the product from Step 3 in 6 mL of N,N-dimethylformamide was added 2 g of potassium carbonate and 0.6 mL of iodomethane. The reaction mixture was stirred at room temperature for 17 h. After removal of the volatile materials, the residue was purified by silica gel chromatography eluting with ethyl acetate/hexane to give 1.2 g of tert-butyl exo-3-[{[4-(benzyloxy)phenyl]sulfonyl}(methyl) amino]bicyclo[2.2.1]heptane-2-carboxylate as a colorless solid.

Electrospray Mass Spec 472.2 (M+H)⁺.

Step 5

A mixture of 1.2 g (2.5 mmol) of the product from Step 4, 1.06 g of 10% Pd/C and 30 mL of ethanol/dichloromethane mixture (9/1) was deoxygenated with nitrogen for 10 min. To the mixture was added 2.8 mL (30 mmol) of 1,4-cyclohexadiene. The resulting reaction mixture was stirred overnight. After filtration, the volatile materials were removed under reduced pressure and the residue was purified by silica gel flash column chromatography to give 0.95 g of tert-butyl exo-3-[[(4-hydroxyphenyl)sulfonyl](methyl)amino]bicyclo [2.2.1]heptane-2-carboxylate as a white solid.

Electrospray Mass Spec 380.1 (M–H)⁻.

Step 6

A mixture of 0.381 g (1 mmol) of the product from Step 5, 0.342 g (1.5 mmol) of 4-chloromethyl-2-methyl-quinoline hydrochloride, 0.553 g (4 mmol) of potassium carbonate and 7 mL of N,N-dimethylformamide was stirred at 38° C. for 16 h. After filtration, the N,N-dimethylformamide was removed under reduced pressure and the residue was purified by silica gel column chromatograpy eluting with ethanol/hexane mixture to give 0.464 g of tert-butyl exo-3-[methyl({4-[(2-methylquinolin-4-yl)methoxy]phenyl}sulfonyl)amino]bicyclo [2.2.1]heptane-2-carboxylate as a yellow solid.

Electrospray Mass Spec 537.2 (M+H)⁺.

Step 7

A solution of 0.439 g (0.82 mmol) of the product from Step 6 in 9 mL of dichloromethane and 3 mL of trifluoroacetice acid was stirred at room temperature for 2 h. After removal of the dichloromethane and trifluoroacetic acid under reduced pressure, 0.595 g of exo-3-{methyl-[4-(2-methyl-quinolin-4-ylmethoxy)-benzenesulfonyl]-amino}-bicyclo[2.2.1]heptane-2-carboxylic acid, trifluoroacetic acetic acid salt, was obtained as a yellow oil.

Electrospray Mass Spec 481.2 (M+H)⁺.

Step 8

To a solution of 0.595 g (0.76 mmol) of the product from Step 7 and 0.308 g (2.28 mmol) of 1-hydroxybenzotriazole in 6 mL of N,N-dimethylformamide at 0° C. was added 0.437 g (2.28 mmol) of 1-[3-(dimethylamino)propyl]-3-ethylcarbodiimide hydrochloride. The reaction mixture was stirred at room temperature for 1.5 h. To the reaction mixture at 0° C. was added 0.372 mL of 50% hydroxylamine solution. The resulting reaction mixture was stirred at room temperature for 18 h. The volatile materials were removed under reduced pressure at below 40° C. The residue was partitioned between 80 mL of ethyl acetate and 15 mL of water. The organic layer was washed with 15 mL of saturated sodium bicarbonate solution and 15 mL of saturated sodium chloride solution and dried over sodium sulfate. After removal of the ethyl acetate, the residue was triturated with a mixture of hexane and ethyl acetate to give 0.215 g of exo-N-hydroxy-3-[methyl({4-[(2-methylquinolin-4-yl)methoxy]phenyl}sulfonyl)amino]bicyclo[2.2.1]heptane-2-carboxamide as a yellow solid.

Electrospray Mass Spec 496.2 (M+H)⁺.

A chiral method was developed to separate the two enantiomers of exo-N-hydroxy-3-[methyl({4-[(2-methylquinolin-4-yl)methoxy]phenyl}sulfonyl)amino]bicyclo[2.2.1] heptane-2-carboxamide, 1a and 1b. This sample was screened using normal phase conditions with Heptane/DEA and Ethanol, with 4 different chiral columns. Only the Chiralpak OJ-H 250*4.6 mm column gave baseline separations. The mobile phase is 40% Heptane/DEA and 60% Ethanol. The flow rate used was 1 mL/min. An AGLIENT LC-1100 BDAD, analyzed these samples at 215 nm. Enantiomer 1 eluted at 5.2 min and enantiomer 2 at 9.2 min with a baseline resolution of 3.4.

Example 2 exo-N-Hydroxy-3-[({4-[(2-methylquinolin-4-yl) methoxy]phenyl}sulfonyl)amino]-7-oxabicyclo [2.2.1]heptane-2-carboxamide

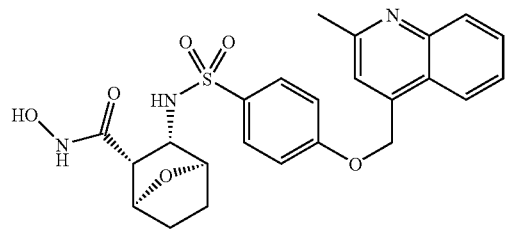

Step 1

A solution of hydroxylamine was prepared by adding sodium carbonate (10.25 g) to an aqueous solution of hydroxylamine hydrochloride (13.15 g in 30 mL of water). exo-7-Oxabicyclo[2.2.1]heptane-2,3-dicarboxylic anhydride (25.6 g) was added slowly to the aqueous solution. After addition, the reaction mixture solidified. The resulting reaction mixture was heated at 65° C. for 1 h. After cooling, 16.8 g of exo-2-hydroxyhexahydro-1H-4,7-epoxyisoindole-1,3-dione were collected as a colorless solid.

Electrospray Mass Spec 182.0 (M–H)⁻.

Step 2

A solution of 9.16 g (0.05 mol) of the product from Step 1 in a mixture of 50 mL of dichloromethane and 9.6 mL (0.055 mol) of diisopropylethylamine was cooled in an ice-bath. To the resulting solution was added a solution of 8.83 g (0.05 mol) of phenylsulfonyl chloride in 25 mL of dichloromethane. The reaction mixture was stirred for 0.5 h (the product precipitated almost immediately). Colorless crystals of exo-2-[(phenylsulfonyl)oxy]hexahydro-1H-4,7-epoxyisoindole-1,3-dione (13.4 g) were collected by filtration and washed with 50 mL of dichloromethane.

Electrospray Mass Spec 324.1 (M+H)⁺.

Step 3

A mixture of 3.23 g of the product from Step 2 and 20 mL of 10% NaOH solution was heated at 70 C with stirring for 5 min. A clear solution was obtained, cooled with an ice-bath and acidified with 6 mL of 12 N HCI. The water was removed under reduced pressure at 30 C and the residue was extracted with boiling ethanol (3×25 mL) to give 1.5 g of exo-3-amino- 7-oxa-bicyclo[2.2.1]heptane-2-carboxylic acid compound with benzenesulfonic acid as a colorless solid.

Electrospray Mass Spec 158.1 (M+H)+.

Step 4

To a suspension of 1.89 g (6 mmol) of the product from Step 3 in 25 mL of dichloromethane under nitrogen was added 3.09 g (12 mmol) of bis(trimethylsilyl)trifluoroacetamide. The resulting mixture was stirred under nitrogen at reflux temperature for 1 hour and then cooled with an ice-bath. To the stirred reaction mixture was added 2.08 g (5.4 mmol) of 4-(2-methyl-quinolin-4-ylmethoxy)-benzenesulfonyl chloride hydrochloride and 2.64 mL of N-methylmorpholine. The resulting mixture was stirred at room temperature overnight and diluted with 100 mL of dichloromethane. To the mixture was added ~30 mL of 0.5 N HCl (pH ~5). The organic layer was washed with 15 mL of water and 40 mL of saturated sodium chloride solution and dried over magnesium sulfate. After filtration and removal of the dichloromethane, the residue was triturated with ethyl acetate/hexane to give 1.82 g of exo-3-[({4-[(2-methylquinolin-4-yl)methoxy]phenyl}sulfonyl)amino]-7-oxabicyclo[2.2.1]heptane-2-carboxylic acid as a yellow solid.

Electrospray Mass Spec 467.1 (M−H)−.

Step 5

To a solution of 0.350 g (0.75 mmol) of the product from Step 4 and 0.324 g (2.4 mmol) of 1-hydroxybenzotriazole in 4 mL of N,N-dimethylformamide at 0° C. was added 0.460 g (2.4 mmol) of 1-[3-(dimethylamino)propyl]-3-ethylcarbodiimide hydrochloride. The reaction mixture was stirred at room temperature for 1.5 h. To the reaction mixture at 0° C. was added 0.343 mL of 50% hydroxylamine solution. The resulting reaction mixture was stirred at room temperature for 18 h. The volatile materials were removed under reduced pressure at below 40° C. The residue was partitioned between 50 mL of ethyl acetate and 15 mL of water. The organic layer was washed successively with 15 mL of 0.5 N HCl solution, 15 mL of saturated sodium bicarbonate solution and 15 mL of saturated sodium chloride solution and dried over sodium sulfate. After removal of the ethyl acetate, the residue was crystallized with a mixture of hexane and ethyl acetate to give 0.142 g of exo-N-hydroxy-3-[({4-[(2-methylquinolin-4-yl)methoxy]phenyl}sulfonyl)amino]-7-oxabicyclo[2.2.1]heptane-2-carboxamide as yellow solid.

Electrospray Mass Spec 484.1 (M+H)+.

Example 3 exo-N-Hydroxy-3-[methyl({4-[(2-methylquinolin-4-yl)methoxy]phenyl}sulfonyl)amino]-7-oxabicyclo[2.2.1]heptane-2-carboxamide

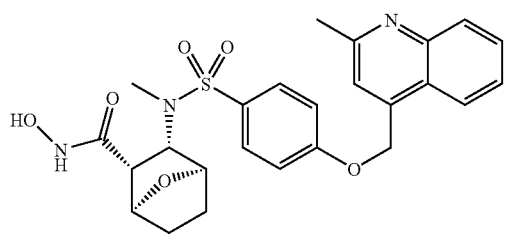

Step 1

To 1.3 g of the product from Example 2, Step 4, was added 12 mL of toluene and 3 mL of N,N-dimethylformamide di-tert-butyl acetal. The resulting mixture was heated at 110° C. for 4.5 h under nitrogen. The volatile materials were removed under reduced pressure. The residue was purified with silica gel column chromatography eluting with ethanol/hexane to give 0.822 g of tert-butyl exo-3-[({4-[(2-methylquinolin-4-yl)methoxy]phenyl}sulfonyl)amino]-7-oxabicyclo[2.2.1]heptane-2-carboxylate as a yellow solid.

Electrospray Mass Spec 525.2 (M+H)+.

Step 2

To a solution of 0.790 g of the product from Example 3, Step 1, in 15 mL of N,N-dimethylformamide was added 0.835 g of potassium carbonate and 0.10 mL of iodomethane. The reaction mixture was stirred at room temperature for 17 h. After filtration and removal of the N,N-dimethylformamide, the residue was dissolved in 100 mL of dichloromethane. The dichoromethane solution was washed with 2×40 mL of water and 2×40 mL of saturated sodium chloride solution and dried over magnesium sulfate. After filtration and removal of the dichloromethane, 0.77 g of tert-butyl exo-3-[methyl({4-[(2-methylquinolin-4-yl)methoxy]phenyl}sulfonyl)amino]-7-oxabicyclo[2.2.1]heptane-2-carboxylate was obtained as yellow foam.

Electrospray Mass Spec 539.2 (M+H)+.

Step 3

A solution of 0.742 g (1.38 mmol) of the product from Example 3, Step 2, in 15 mL of dichloromethane and 6 mL of trifluoroacetice acid was stirred at room temperature for 2 h. After removal of the dichloromethane and trifluoroacetic acid under reduced pressure, 0.787 g of exo-3-[methyl({4-[(2-methylquinolin-4-yl)methoxy]phenyl}sulfonyl)amino]-7-oxabicyclo[2.2.1]heptane-2-carboxylic acid compound with trifluoroacetic acid was obtained as a yellow oil.

Electrospray Mass Spec 483.1 (M+H)+.

Step 4

To a solution of 0.787 g (1.32 mmol) of the product from Example 3, Step 3, and 0.535 g (3.96 mmol) of 1-hydroxybenzotriazole in 8 mL of N,N-dimethylformamide at 0° C. was added 0.759 g (3.96 mmol) of 1-[3-(dimethylamino)propyl]-3-ethylcarbodiimide hydrochloride. The reaction mixture was stirred at room temperature for 1.5 h. To the reaction mixture at 0° C. was added 0.647 mL of 50% hydroxylamine solution. The resulting reaction mixture was stirred at room temperature for 18 h. The volatile materials were removed under reduced pressure at below 40° C. The residue was partitioned between 100 mL of ethyl acetate and 15 mL of water. The organic layer was washed with 4×30 mL of saturated sodium bicarbonate solution and 30 mL of saturated sodium chloride solution and dried over sodium sulfate. After removal of the ethyl acetate, the residue was triturated with a mixture of hexane and ethyl acetate to give 0.397 g of exo-N-hydroxy-3-[methyl({4-[(2-methylquinolin-4-yl)methoxy]phenyl}sulfonyl)amino]-7-oxabicyclo[2.2.1]heptane-2-carboxamide as a yellow solid.

Electrospray Mass Spec 498.1 (M+H)+.

Example 4 exo-N-Hydroxy-3-[({4-[(2-methylquinolin-4-yl)methoxy]phenyl}sulfonyl)amino]bicyclo[2.2.1]heptane-2-carboxamide

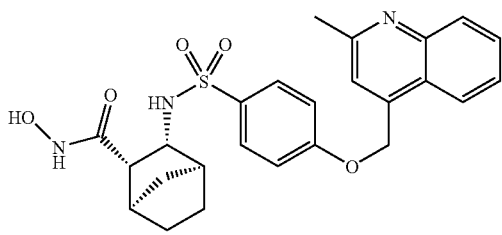

Step 1

To a suspension of 0.466 g (3 mmol) of 3-exo-aminobicyclo[2.2.1]heptane-2-exo-carboxylic acid in 15 mL of dichloromethane under nitrogen was added 1.59 mL (6 mmol) of bis(trimethylsilyl)trifluoroacetamide. The resulting mixture was stirred under nitrogen at reflux temperature for 1 hour and then cooled with an ice-bath. To the stirred reaction mixture was added 0.91 g of 4-(2-methyl-quinolin-4-ylmethoxy)-benzenesulfonyl chloride hydrochloride and 0.990 mL of N-methylmorpholine. The resulting mixture was stirred at room temperature overnight. To the mixture was added 18 mL of 0.5 N HCl solution (pH ~5). The desired product precipitated. The yellow solid was collected by filtration and washed with a small volume of cold water and ethyl acetate/hexane mixture to give 0.423 g of exo-3-[({4-[(2-methylquinolin-4-yl)methoxy]phenyl}sulfonyl)amino]bicyclo[2.2.1]heptane-2-carboxylic acid.

Electrospray Mass Spec 467.1 (M+H)$^+$.

Step 2

To a solution of 0.260 g (0.0.55 mmol) of the product from Example 4, Step 1, and 0.226 g (1.67 mmol) of 1-hydroxybenzotriazole in 4 mL of N,N-dimethylformamide at 0° C. was added 0.320 g (1.67 mmol) of 1-[3-(dimethylamino)propyl]-3-ethylcarbodiimide hydrochloride. The reaction mixture was stirred at room temperature for 1.5 h. To the reaction mixture at 0° C. was added 0.270 mL of 50% hydroxylamine solution. The resulting reaction mixture was stirred at room temperature for 18 h. The volatile materials were removed under reduced pressure at below 40° C. The residue was dissolved between 80 mL of ethyl acetate. The organic layer was washed with a saturated sodium bicarbonate solution (5×30 mL) and a saturated sodium chloride solution (2×30 mL) and dried over sodium sulfate. After removal of the ethyl acetate, the residue was triturated with a 7:3 hexane:ethyl acetate mixture to give 0.183 g of exo-N-hydroxy-3-[({4-[(2-methylquinolin-4-yl)methoxy]phenyl}sulfonyl)amino]bicyclo[2.2.1]heptane-2-carboxamide as a yellow solid.

Electrospray Mass Spec 482.1 (M+H)$^+$.

Example 5 endo-N-Hydroxy-3-[methyl({4-[(2-methylquinolin-4-yl)methoxy]phenyl}sulfonyl)amino]bicyclo[2.2.1]heptane-2-carboxamide

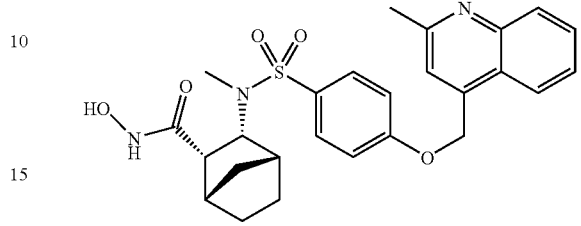

Step 1

According to the procedure of Example 1, Step 2, the reaction of 1.53 g of 3-endo-aminobicyclo[2,2,1]hept-5-ene-2-endo-carboxylic acid with 4-benzyloxybenzene-sulfonyl chloride provided 3.24 g of endo-3-({[4-(benzyloxy)phenyl]sulfonyl}amino)bicyclo[2.2.1]hept-5-ene-2-carboxylic acid in 81% yield. MS: 398.2 (M−H)$^−$

Step 2

According to the procedure of Example 1, Step 3, the reaction of 2.95 g of endo-3-({[4-(benzyloxy)phenyl]sulfonyl}amino)bicyclo[2.2.1]hept-5-ene-2-carboxylic acid with N,N-dimethylformamide di-tert-butyl acetal provided 2.57 g tert-butyl endo-3-({[4-(benzyloxy)phenyl]sulfonyl}amino)bicyclo[2.2.1]hept-5-ene-2-carboxylate in 76% yield. MS: 454.3 (M−H)$^−$

Step 3

According to the procedure of Example 1, Step 4, the reaction of 1.43 g of tert-butyl endo-3-({[4-(benzyloxy)phenyl]sulfonyl}amino)bicyclo[2.2.1]hept-5-ene-2-carboxylate with iodomethane provided 1.46 g of tert-butyl endo -3-[{[4-(benzyloxy)phenyl]sulfonyl}(methyl)amino]bicyclo[2.2.1]hept-5-ene-2-carboxylate in 99% yield. MS: 470.1 (M+H)$^+$

Step 4

According to the procedure of Example 1, Step 5, the reaction of 1.18 g of tert-butyl endo-3-[{[4-(benzyloxy)phenyl]sulfonyl}(methyl)amino]bicyclo[2.2.1]hept-5-ene-2-carboxylate with 1,4-cyclohexadiene provided 0.96 of tert-butyl endo-3-[[(4-hydroxyphenyl)sulfonyl](methyl)amino]bicyclo[2.2.1]heptane-2-carboxylate in 99% yield. MS: 380.2 (M−H)$^−$

Step 5

According to the procedure of Example 1, Step 6, the reaction of 343.3 mg of tert-butyl endo-3-[[(4-hydroxyphenyl)sulfonyl](methyl)amino]bicyclo[2.2.1]heptane-2-carboxylate with 4-chloromethyl-2-methyl-quinoline hydrochloride provided 405.8 mg of the desired product tert-butyl endo-3-[methyl({4-[(2-methylquinolin-4-yl)methoxy]phenyl}sulfonyl)amino]bicyclo[2.2.1]heptane-2-carboxylate in 84% yield. MS: 537.3 (M+H)$^+$

Step 6

According to the procedure of Example 1, Step 7, the reaction of 379 mg of tert-butyl endo-3-[methyl({4-[(2-methylquinolin-4-yl)methoxy]phenyl}sulfonyl)amino]bicyclo[2.2.1]heptane-2-carboxylate with trifluoroacetic acid provided the desired product endo-3-[methyl({4-[(2- methylquinolin-4-yl)methoxy]phenyl}sulfonyl)amino]bicyclo[2.2.1]heptane-2-carboxylic acid in quantitative yield. MS: 481.2 (M+H)⁺

Step 7

According to the procedure of Example 1, Step 8, the reaction of 380 mg of endo-3-[methyl({4-[(2-methylquinolin-4-yl)methoxy]phenyl}sulfonyl)amino]bicyclo[2.2.1]heptane-2-carboxylic acid with hydroxylamine provided 289 mg of the desired product endo-N-hydroxy-3-[methyl({4-[(2-methylquinolin-4-yl)methoxy]phenyl}sulfonyl)amino]bicyclo[2.2.1]heptane-2-carboxamide in 92% yield. MS: 496.3 (M+H)⁺

Example 6 endo-N-Hydroxy-3-[({4-[(2-methylquinolin-4-yl)methoxy]phenyl}sulfonyl)amino]bicyclo[2.2.1]heptane-2-carboxamide

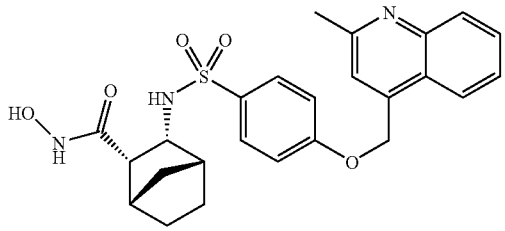

Step 1

According to the procedure of Example 1, Step 5, the reaction of 913 mg of tert-butyl endo-3-({[4-(benzyloxy)phenyl]sulfonyl}amino)bicyclo[2.2.1]hept-5-ene-2-carboxylate (Example 5, Step 2) with 1,4-cyclohexadiene provided 680 mg of tert-butyl endo-3-{[(4-hydroxyphenyl)sulfonyl]amino}bicyclo[2.2.1]heptane-2-carboxylate in 93% yield. MS: 366.2 (M−H)⁻

Step 2

According to the procedure of Example 1, Step 6, the reaction of 367.5 mg of tert-butyl endo-3-{[(4-hydroxyphenyl)sulfonyl]amino}bicyclo[2.2.1]heptane-2-carboxylate with 4-(2-methyl-quinolin-4-ylmethoxy)-benzenesulfonyl chloride hydrochloride provided tert-butyl endo-3-[({4-[(2-methylquinolin-4-yl)methoxy]phenyl}sulfonyl)amino]bicyclo[2.2.1]heptane-2-carboxylate in quantitative yield. MS: 523.3 (M+H)⁺

Step 3

According to the procedure of Example 1, Step 7, the reaction of 490 mg of tert-butyl endo-3-[({4-[(2-methylquinolin-4-yl)methoxy]phenyl}sulfonyl)amino]bicyclo[2.2.1]heptane-2-carboxylate with trifluoroacetic acid provided endo-3-[({4-[(2-methylquinolin-4-yl)methoxy]phenyl}sulfonyl)amino]bicyclo[2.2.1]heptane-2-carboxylic acid in quantitative yield. MS: 467.2 (M+H)⁺

Step 4

According to the procedure of Example 1, Step 8, the reaction of 493 mg of endo-3-[({4-[(2-methylquinolin-4-yl)methoxy]phenyl}sulfonyl)amino]bicyclo[2.2.1]heptane-2-carboxylic acid with hydroxylamine provided 377.1 mg of endo-N-hydroxy-3-[({4-[(2-methylquinolin-4-yl)methoxy]phenyl}sulfonyl)amino]bicyclo[2.2.1]heptane-2-carboxamide in 92% yield. MS: 482.0 (M+H)⁺

Example 7 endo-N-Hydroxy-3-[({4-[(2-methylquinolin-4-yl)methoxy]phenyl}sulfonyl)amino]bicyclo[2.2.1]hept-5-ene-2-carboxamide

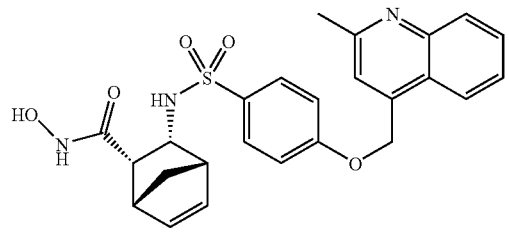

Step 1

According to the procedure of Example 4, Step 1, the reaction of 306 mg of 3-endo-aminobicyclo[2,2,1]hept-5-ene-2-endo-carboxylic acid with 4-(2-methyl-quinolin-4-yl-methoxy)-benzenesulfonyl chloride hydrochloride provided 473 mg of endo-3-[({4-[(2-methylquinolin-4-yl)methoxy]phenyl}sulfonyl)amino]bicyclo[2.2.1]hept-5-ene-2-carboxylic acid in 51% yield. MS: 465.0 (M+H)⁺

Step 2

According to the procedure of Example 4, Step 2, the reaction of 170 mg of endo-3-[({4-[(2-methylquinolin-4-yl)methoxy]phenyl}sulfonyl)amino]bicyclo[2.2.1]hept-5-ene-2-carboxylic acid with hydroxylamine provided 90 mg of endo-N-hydroxy-3-[({4-[(2-methylquinolin-4-yl)methoxy]phenyl}sulfonyl)amino]bicyclo[2.2.1]hept-5-ene-2-carboxamide in 51% yield. MS: 480.0 (M+H)⁺

Example 8 endo-N-Hydroxy-3-[methyl({4-[(2-methylquinolin-4-yl)methoxy]phenyl}sulfonyl)amino]bicyclo[2.2.1]hept-5-ene-2-carboxamide

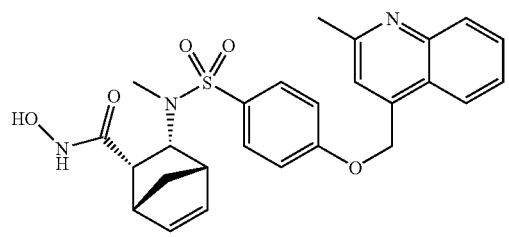

Step 1

According to the procedure of Example 1, Step 4, the reaction of 291.5 mg of endo-3-[({4-[(2-methylquinolin-4-yl)methoxy]phenyl}sulfonyl)amino]bicyclo[2.2.1]hept-5-ene-2-carboxylic acid (Example 7, Step 1) with iodomethane provided 283.1 mg of methyl endo-3-[methyl({4-[(2-methylquinolin-4-yl)methoxy]phenyl}sulfonyl)amino]bicyclo[2.2.1]hept-5-ene-2-carboxylate in 91% yield. MS: 493.0 (M+H)⁺

Step 2

To the stirred solution of 260 mg of methyl endo-3-[methyl({4-[(2-methylquinolin-4-yl)methoxy]phenyl}sulfonyl)

amino]bicyclo[2.2.1]hept-5-ene-2-carboxylate in 6 mL of THF and 3 mL of methanol was added 5 mL of 1N lithium hydroxide solution. The reaction mixture was stirred overnight. The solution was adjusted to pH 6 and the desired product precipitated. The colorless solid was collected by filtration, washed with a small volume of cold water and dried under reduced pressure to give 196.8 mg of endo-3-[methyl({4-[(2-methylquinolin-4-yl)methoxy]phenyl}sulfonyl)amino]bicyclo[2.2.1]hept-5-ene-2-carboxylic acid in 78% yield. MS: 479.1 (M+H)+

Step 3

According to the procedure of Example 1, Step 8, the reaction of 170 mg of endo-3-[methyl({4-[(2-methylquinolin-4-yl)methoxy]phenyl}sulfonyl)amino]bicyclo[2.2.1]hept-5-ene-2-carboxylic acid with hydroxylamine provided 138 mg of endo-N-hydroxy-3-[methyl({4-[(2-methylquinolin-4-yl)methoxy]phenyl}sulfonyl)amino]bicyclo[2.2.1]hept-5-ene-2-carboxamide in 80% yield. MS: 494.1 (M+H)+

Example 9 exo-N-Hydroxy-3-[({4-[(2-methylquinolin-4-yl)methoxy]phenyl}sulfonyl)amino]bicyclo[2.2.1]hept-5-ene-2-carboxamide

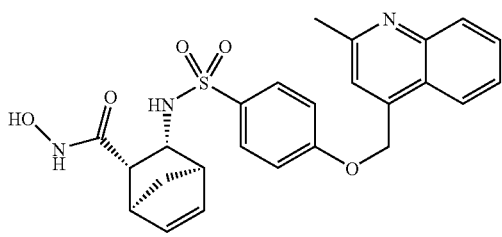

Step 1

According to the procedure of Example 4, Step 1, the reaction of 153 mg of 3-exo-aminobicyclo[2,2,1]hept-5-ene-2-exo-carboxylic acid with 4-(2-methyl-quinolin-4-ylmethoxy)-benzenesulfonyl chloride hydrochloride provided 256 mg of exo-3-[({4-[(2-methylquinolin-4-yl)methoxy]phenyl}sulfonyl)amino]bicyclo[2.2.1]hept-5-ene-2-carboxylic acid in 55% yield. MS: 465.0 (M+H)+

Step 2

According to the procedure of Example 4, Step 2, the reaction of 93 mg of exo-3-[({4-[(2-methylquinolin-4-yl)methoxy]phenyl}sulfonyl)amino]bicyclo[2.2.1]hept-5-ene-2-carboxylic acid with hydroxylamine provided 55 mg of exo-N-hydroxy-3-[({4-[(2-methylquinolin-4-yl)methoxy]phenyl}sulfonyl)amino]bicyclo[2.2.1]hept-5-ene-2-carboxamide with 60% yield. MS: 480.1 (M+H)+

Example 10 cis-N-hydroxy-6-[({4-[(2-methylquinolin-4-yl)methoxy]phenyl}sulfonyl)amino]cyclohex-3-ene-1-carboxamide

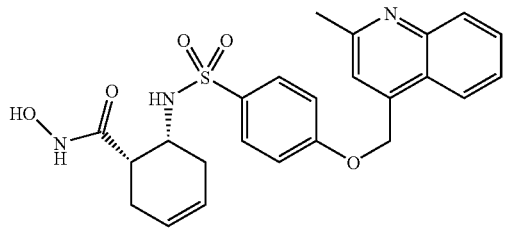

Step 1

To a stirred solution of 423.5 mg (3 mmol) of cis-2-amino-4-cyclohexene-1-carboxylic acid in 8 mL of dioxane and 8 mL of water was added 2.1 mL of triethylamine, followed by 1.13 g (3 mmol) of 4-(2-methyl-quinolin-4-ylmethoxy)-benzenesulfonyl chloride hydrochloride in one portion as a solid. The solution was stirred at room temperature overnight. After removal of the volatile material, 10 mL of dichloromethane and 10 mL of water were added to the residue. The mixture was adjusted pH to 5 with 1N HCl solution. The solid was collected by filtration, washed with a small volume of water, followed by dichloromethane to provide 1.05 g of cis-6-[({4-[(2-methylquinolin-4-yl)methoxy]phenyl}sulfonyl)amino]cyclohex-3-ene-1-carboxylic acid in 77% yield. MS: 453.1 (M+H)+

Step 2

To a solution of 181.0 mg (0.4 mmol) of cis-6-[({4-[(2-methylquinolin-4-yl)methoxy]phenyl}sulfonyl)amino]cyclohex-3-ene-1-carboxylic acid and 162.2 mg (1.2 mmol) of 1-hydroxybenzotriazole in 3 mL of N,N-dimethylformamide at 0° C. was added 230.0 mg (1.2 mmol) of 1-[3-(dimethylamino)propyl]-3-ethylcarbodiimide hydrochloride. The reaction mixture was stirred at room temperature for 1.5 h. To the reaction mixture at 0° C. was added 0.2 mL of 50% hydroxylamine solution. The resulting reaction mixture was stirred at room temperature for 18 h. The volatile materials were removed under reduced pressure, below 40° C. The residue was dissolved in 80 mL of ethyl acetate. The organic layer was washed with a saturated sodium bicarbonate solution (5×30 mL) and a saturated sodium chloride solution (2×30 mL) and dried over sodium sulfate. After removal of the ethyl acetate, the residue was triturated with a 7:3 mixture of hexane:ethyl acetate to give 71.9 mg of cis-N-hydroxy-6-[({4-[(2-methylquinolin-4-yl)methoxy]phenyl}sulfonyl)amino]cyclohex-3-ene-1-carboxamide as a solid in 38% yield. MS: 468.1 (M+H)+

Example 11 cis-N-Hydroxy-2-[({4-[(2-methylquinolin-4-yl)
methoxy]phenyl}sulfonyl)amino]cyclopentanecarboxamide

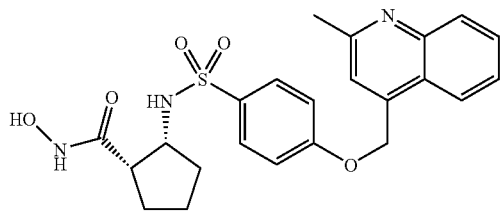

Step 1

According to the procedure of Example 10, Step 1, the reaction of 322.9 mg (2.5 mmol) of cis-2-amino-1-cyclopentane-carboxylic acid with 960.7 mg of 4-(2-methyl-quinolin-4-ylmethoxy)-benzenesulfonyl chloride hydrochloride provided 927.7 mg of cis-2-[({4-[(2-methylquinolin-4-yl)methoxy]phenyl}sulfonyl)amino]cyclopentanecarboxylic acid in 84% yield. MS: 441.1 (M+H)$^+$

Step 2

According to the procedure of Example 10, Step 2, the reaction of 220.3 mg (0.5 mmol) of cis-2-[({4-[(2-methylquinolin-4-yl)methoxy]phenyl}sulfonyl)amino]cyclopentanecarboxylic acid with hydroxylamine provided 156.1 mg of cis-N-hydroxy-2-[({4-[(2-methylquinolin-4-yl)methoxy]phenyl}sulfonyl)amino]cyclopentanecarboxamide in 69% yield. MS: 456.1 (M+H)$^+$

Example 12 cis-N-hydroxy-2-[({4-[(2-methylquinolin-4-yl)methoxy]phenyl}sulfonyl)amino]cyclohexanecarboxamide

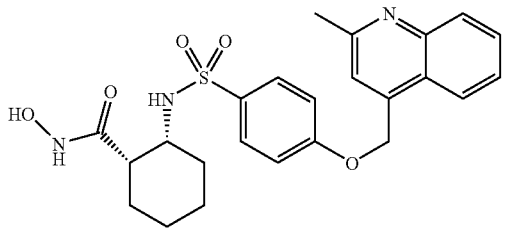

Step 1

According to the procedure of Example 10, Step 1, the reaction of 429.6 mg (3 mmol) of cis-2-amino-1-cyclohexane-carboxylic acid with 1.15 g of 4-(2-methyl-quinolin-4-ylmethoxy)-benzenesulfonyl chloride hydrochloride provided 387.9 mg of cis-2-[({4-[(2-methylquinolin-4-yl)methoxy]phenyl}sulfonyl)amino]cyclohexanecarboxylic acid in 28% yield. MS: 455.1 (M+H)$^+$

Step 2

According to the procedure of Example 10, Step 2, the reaction of 113.6 mg (0.5 mmol) of cis-2-[({4-[(2-methylquinolin-4-yl)methoxy]phenyl}sulfonyl)amino]cyclohexanecarboxylic acid with hydroxylamine provided 53.7 mg of the title compound in 46% yield. MS: 470.1 (M+H)$^+$

Example 13

(1S,2R)-N-Hydroxy-2-[({4-[(2-methylquinolin-4-yl)
methoxy]phenyl}sulfonyl)amino]cyclopentanecarboxamide

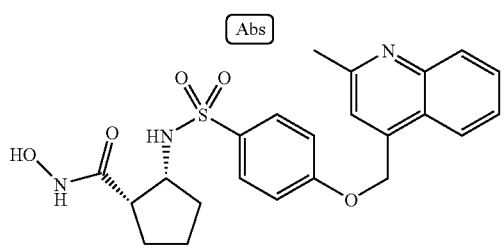

Step 1

According to the procedure of Example 10, Step 1, the reaction of 141 mg (0.85 mmol) of (+)-(1S,2R)-2-amino-1-cyclopentane-carboxylic acid hydrochloride with 400 mg (1.04 mmol) of 4-(2-methyl-quinolin-4-ylmethoxy)-benzenesulfonyl chloride hydrochloride provided 327.9 mg of (1S,2R)-2-[({4-[(2-methylquinolin-4-yl)methoxy]phenyl}sulfonyl)amino]cyclopentanecarboxylic acid in 86% yield. MS: 441.1 (M+H)$^+$

Step 2

According to the procedure of Example 10, Step 2, the reaction of 321.4 mg (0.73 mmol) of (1S,2R)-2-[({4-[(2-methylquinolin-4-yl)methoxy]phenyl}sulfonyl)amino]cyclopentanecarboxylic acid with hydroxylamine provided 139.5 mg of (1S,2R)-N-hydroxy-2-[({4-[(2-methylquinolin-4-yl)methoxy]phenyl}sulfonyl)amino]cyclopentanecarboxamide with 43% yield. MS: 456.1 (M+H)$^+$

Example 14 trans-N-Hydroxy-2-[({4-[(2-methylquinolin-4-yl)
methoxy]phenyl}sulfonyl)amino]cyclohexanecarboxamide

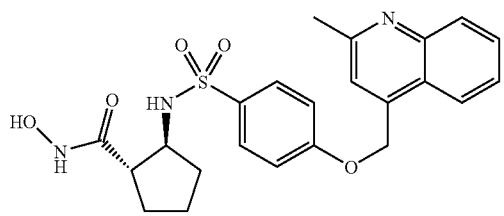

Step 1

According to the procedure of Example 10, Step 1, the reaction of 486.8 mg (3.4 mmol) of trans-2-amino-1-cyclohexane-carboxylic acid with 1.31 g of 4-(2-methyl-quinolin-4-ylmethoxy)-benzenesufonyl chloride hydrochloride provided 382.7 mg of trans-2-[({4-[(2-methylquinolin-4-yl)methoxy]phenyl}sulfonyl)amino]cyclohexanecarboxylic acid in 25% yield. MS: 455.1 (M+H)$^+$ Step 2

According to the procedure of Example 10, Step 2, the reaction of 186.8 mg (0.4 mmol) of trans-2-[({4-[(2-methylquinolin-4-yl)methoxy]phenyl}sulfonyl)amino]cyclohexanecarboxylic acid with hydroxylamine provided 31.8 mg of trans-N-hydroxy-2-[({4-[(2-methylquinolin-4-yl)methoxy]phenyl}sulfonyl)amino]cyclohexanecarboxamide in 16% yield. MS: 470.1 (M+H)+

Example 15 cis-N-Hydroxy-6-[methyl({4-[(2-methylquinolin-4-yl)methoxy]phenyl}sulfonyl)amino]cyclohex-3-ene-1-carboxamide

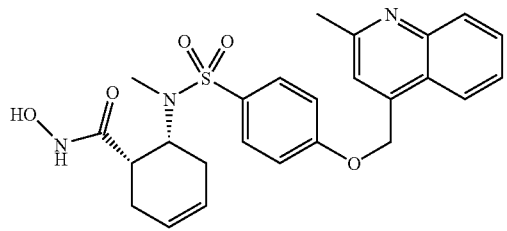

Step 1

To a solution of 456.5 mg of cis-6-[({4-[(2-methylquinolin-4-yl)methoxy]phenyl}sulfonyl)amino]cyclohex-3-ene-1-carboxylic acid (Example 10, Step 1) in 4 mL of toluene was added 1.1 mL of N,N-dimethylformamide di-tert-butyl acetal. The solution was refluxed for 4 hr. After removal of the volatile material, 352 mg of tert-butyl cis-6-[({4-[(2-methylquinolin-4-yl)methoxy]phenyl}sulfonyl)amino]cyclohex-3-ene-1-carboxylate was obtained by flash column chromatography, eluting with ethyl acetate/hexane (3:7), in 68% yield. MS: 509.2 (M+H)+

Step 2

To a stirred solution of 325.5 mg (0.64 mmol) of tert-butyl cis-6-[({4-[(2-methylquinolin-4-yl)methoxy]phenyl}sulfonyl)amino]cyclohex-3-ene-1-carboxylate in 4 mL of N,N-dimethylformamide was added 353.8 mg of potassium carbonate, followed by 184.9 mg (1.28 mmol) of iodomethane. The suspension was stirred at room temperature overnight. After removal of the volatile material, 80 mL of ethyl acetate was added. The organic phase was washed with water and saturated sodium chloride solution, and dried over magnesium sulfate. The residue was chromatographed on silica gel eluting with ethyl acetate/hexane (3:7) to give 292.1 mg of tert-butyl cis-6-[methyl({4-[(2-methylquinolin-4-yl)methoxy]phenyl}sulfonyl)amino]cyclohex-3-ene-1-carboxylate in 87% yield. MS: 523.1 (M+H)+

Step 3

To a stirred solution of 267.1 mg of tert-butyl cis-6-[methyl({4-[(2-methylquinolin-4-yl)methoxy]phenyl}sulfonyl)amino]cyclohex-3-ene-1-carboxylate in 6 mL of dichloromethane was slowly added 2 mL of trifluoroacetic acid. The solution was stirred at room temperature for 3 hr. After removal of the volatile material cis-6-[methyl({4-[(2-methylquinolin-4-yl)methoxy]phenyl}sulfonyl)amino]cyclohex-3-ene-1-carboxylic acid was obtained in quantitative yield. MS: 467.1 (M+H)+

Step 4

According to the procedure of Example 10, Step 2, the reaction of 255.5 mg (0.4 mmol) of cis-6-[methyl({4-[(2-methylquinolin-4-yl)methoxy]phenyl}sulfonyl)amino]cyclohex-3-ene-1-carboxylic acid with hydroxylamine provided 200.1 mg of cis-N-hydroxy-6-[methyl({4-[(2-methylquinolin-4-yl)methoxy]phenyl}sulfonyl)amino]cyclohex-3-ene-1-carboxamide in 94% yield. MS: 482.1 (M+H)+

Example 16 cis-N-Hydroxy-2-[methyl({4-[(2-methylquinolin-4-yl)methoxy]phenyl}sulfonyl)amino]cyclopentanecarboxamide

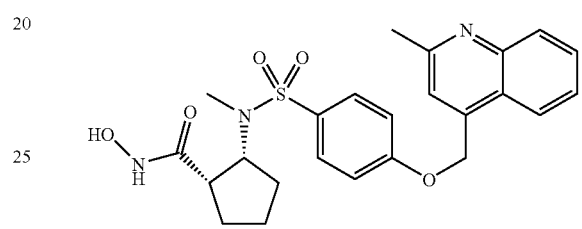

Step 1

According to the procedure of Example 15, Step 1, the reaction of 327.2 mg (0.74 mmol) of cis-2-[({4-[(2-methylquinolin-4-yl)methoxy]phenyl}sulfonyl)amino]cyclopentanecarboxylic acid (Example 11, Step 1) with N,N-dimethylformamide di-tert-butyl acetal provided 274.0 mg of tert-butyl cis-2-[({4-[(2-methylquinolin-4-yl)methoxy]phenyl}sulfonyl)amino]cyclopentanecarboxylate in 67% yield. MS: 497.1 (M+H)+

Step 2

According to the procedure of Example 15, Step 2, the reaction of 250.0 mg (0.5 mmol) of tert-butyl cis-2-[({4-[(2-methylquinolin-4-yl)methoxy]phenyl}sulfonyl)amino]cyclopentanecarboxylate with iodomethane provided 238.0 mg of tert-butyl cis-2-[methyl({4-[(2-methylquinolin-4-yl)methoxy]phenyl}sulfonyl)amino]cyclopentanecarboxylate in 93% yield. MS: 511.2 (M+H)+

Step 3

According to the procedure of Example 15, Step 3, the reaction of 215 mg (0.42 mmol) of tert-butyl cis-2-[methyl({4-[(2-methylquinolin-4-yl)methoxy]phenyl}sulfonyl)amino]cyclopentanecarboxylate with trifluoroacetic acid provided cis-2-[methyl({4-[(2-methylquinolin-4-yl)methoxy]phenyl}sulfonyl)amino]cyclopentanecarboxylic acid in quantitative yield. MS: 455.1 (M+H)+

Step 4

According to the procedure of Example 10, Step 2, the reaction of 222 mg (0.39 mmol) of cis-2-[methyl({4-[(2-methylquinolin-4-yl)methoxy]phenyl}sulfonyl)amino]cyclopentanecarboxylic acid with hydroxylamine provided 183 mg of cis-N-hydroxy-2-[methyl({4-[(2-methylquinolin-4-yl)methoxy]phenyl}sulfonyl)amino]cyclopentanecarboxamide in 97% yield. MS: 470.1 (M+H)+

Example 17 cis-N-Hydroxy-4-[({4-[(2-methylquinolin-4-yl)methoxy]phenyl}sulfonyl)amino]-1-(methylsulfonyl)pyrrolidine-3-carboxamide

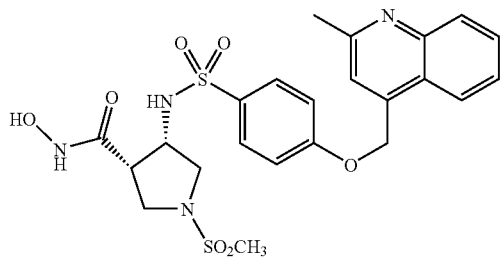

Step 1

To the stirred solution of 687 mg (2.4 mol) of di-tert-butyl cis-4-aminopyrrolidine-1,3-dicarboxylate (prepared according to J. Med. Chem. 2001, 44, 1192-1201) was added 2.1 mL of Hunig's base in 10 mL of N,N-dimethylformamide and 922 mg of 4-(2-methyl-quinolin-4-ylmethoxy)-benzenesulfonyl chloride hydrochloride. The solution was stirred at room temperature overnight. The N,N-dimethylformamide was removed in vacuo, and the residue was dissolved in 100 mL of chloroform. The chloroform solution was washed with water and saturated sodium chloride solution, dried over magnesium sulfate, filtered and concentrated in vacuo. The residue was purified using flash chromatography on silica gel eluting with ethyl acetate/hexane to provide 929 mg (65% yield) of di-tert-butyl cis-4-[({4-[(2-methylquinolin-4-yl)methoxy]phenyl}sulfonyl)amino]pyrrolidine-1,3-dicarboxylate. MS: 598.4 (M+H)$^+$

Step 2

Hydrogen chloride (gas) was passed through a solution of 1.19 g of di-tert-butyl cis-4-[({4-[(2-methylquinolin-4-yl)methoxy]phenyl}sulfonyl)amino]pyrrolidine-1,3-dicarboxylate in 80 mL of dichloromethane for 30 min. After removal of the volatile material 1.03 g of tert-butyl cis-4-[({4-[(2-methylquinolin-4-yl)methoxy]phenyl}sulfonyl)amino]pyrrolidine-3-carboxylate hydrochloride was obtained. MS: 498.3 (M+H)$^+$

Step 3

To the stirred solution of 373 mg of tert-butyl cis-4-[({4-[(2-methylquinolin-4-yl)methoxy]phenyl}sulfonyl)amino]pyrrolidine-3-carboxylate hydrochloride in 8 mL of N,N-dimethylformamide and 0.5 mL of Hunig's base was slowly added 104 mg of methanesulfonyl chloride. The solution was stirred at room temperature overnight. After removal of the N,N-dimethylformamide in vacuo, the residue was dissolved in 80 mL of ethyl acetate. The ethyl acetate solution was washed with water and saturated sodium chloride solution, dried over magnesium sulfate, filtered and concentrated in vacuo. The residue was chromatographed on silica gel eluting with ethyl acetate/hexane to provide 233 mg of tert-butyl cis-4-[({4-[(2-methylquinolin-4-yl)methoxy]phenyl}sulfonyl)amino]-1-(methylsulfonyl)pyrrolidine-3-carboxylate in 58% yield. MS: 576.1 (M+H)$^+$

Step 4

To a stirred solution of 153 mg of tert-butyl cis-4-[({4-[(2-methylquinolin-4-yl)methoxy]phenyl}sulfonyl)amino]-1-(methylsulfonyl)pyrrolidine-3-carboxylate in 4 mL of dichloromethane was slowly added 2 mL of trifluoroacetic acid. The solution was stirred at room temperature for 3 h. After removal of the volatile material cis-4-[({4-[(2-methylquinolin-4-yl)methoxy]phenyl}sulfonyl)amino]-1-(methylsulfonyl) pyrrolidine-3-carboxylic acid was obtained in quantitative yield without further purification. MS: 520.1 (M+H)$^+$

Step 5

To a solution of 152 mg (0.24 mmol) of cis-4-[({4-[(2-methylquinolin-4-yl)methoxy]phenyl}sulfonyl)amino]-1-(methylsulfonyl)pyrrolidine-3-carboxylic acid and 97.3 mg (0.72 mmol) of 1-hydroxybenzotriazole in 3 mL of N,N-dimethylformamide at 0° C. was added 138 mg (0.72 mmol) of 1-[3-(dimethylamino)propyl]-3-ethylcarbodiimide hydrochloride. The reaction mixture was stirred at room temperature for 1.5 h. To the 0° C. reaction mixture was added 0.12 mL of 50% hydroxylamine solution. The resulting reaction mixture was stirred at room temperature for 18 h. The volatile materials were removed under reduced pressure below 40° C. The residue was dissolved in 80 mL of ethyl acetate. The organic layer was washed with a saturated sodium bicarbonate solution (5×30 mL) and a saturated sodium chloride solution (2×30 mL), dried over sodium sulfate and filtered. After removal of the ethyl acetate, the residue was triturated with a 7:3 hexane:ethyl acetate mixture to give 114.1 mg of cis-N-hydroxy-4-[({4-[(2-methylquinolin-4-yl)methoxy]phenyl}sulfonyl)amino]-1-(methylsulfonyl)pyrrolidine-3-carboxamide as a yellow solid in 89% yield. MS: 535.2 (M+H)$^+$

Example 18 cis-N-Hydroxy-4-[({4-[(2-methylquinolin-4-yl)methoxy]phenyl}sulfonyl)amino]-1-prop-2-yn-1-ylpyrrolidine-3-carboxamide

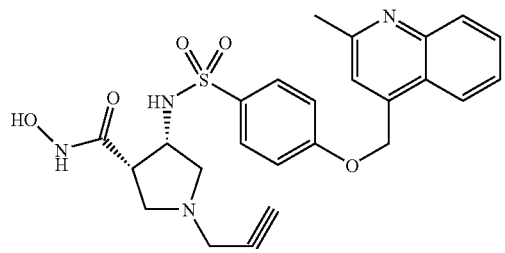

Step 1

According to the procedure of Example 17, Step 3, 228.2 mg of tert-butyl cis-4-[({4-[(2-methylquinolin-4-yl)methoxy]phenyl}sulfonyl)amino]pyrrolidine-3-carboxylate hydrochloride was reacted with 51 mg of propargyl bromide to provide 126 mg of tert-butyl cis-4-[({4-[(2-methylquinolin-4-yl)methoxy]phenyl}sulfonyl)amino]-1-prop-2-yn-1-ylpyrrolidine-3-carboxylate in 55% yield. MS: 536.3(M+H)$^+$

Step 2

According to the procedure of Example 17, Steps 4 and 5, 117 mg of tert-butyl cis-4-[({4-[(2-methylquinolin-4-yl)methoxy]phenyl}sulfonyl)amino]-1-prop-2-yn-1-ylpyrrolidine-3-carboxylate, was treated with trifluoroacetic acid, followed by the reaction with hydroxylamine to give 56 mg of cis-N-hydroxy-4-[({4-[(2-methylquinolin-4-yl)methoxy]phenyl}sulfonyl)amino]-1-prop-2-yn-1-ylpyrrolidine-3-carboxamide in 54% yield. MS: 495 2(M+H)+

Example 19 cis-1-acetyl-N-Hydroxy-4-[({4-[(2-methylquinolin-4-yl)methoxy]phenyl}sulfonyl)amino]pyrrolidine-3-carboxamide

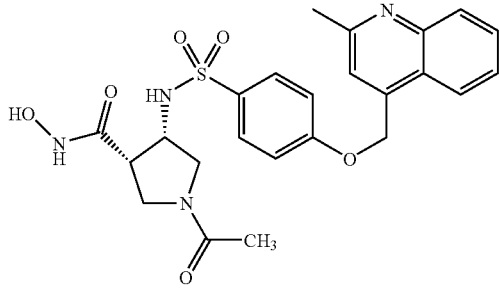

Step 1

According to the procedure of Example 17, Step 3, the reaction of 320.4 mg of tert-butyl cis-4-[({4-[(2-methylquinolin-4-yl)methoxy]phenyl}sulfonyl)amino]pyrrolidine-3-carboxylate hydrochloride with 57 mg of acetyl chloride provided 127 mg (39% yield) of tert-butyl cis-1-acetyl-4-[({4-[(2-methylquinolin-4-yl)methoxy]phenyl}sulfonyl)amino]pyrrolidine-3-carboxylate. MS: 540.1(M+H)+

Step 2

According to the procedure of Example 17, Step 4, the reaction of 115 mg of tert-butyl cis-1-acetyl-4-[({4-[(2-methylquinolin-4-yl)methoxy]phenyl}sulfonyl)amino]pyrrolidine-3-carboxylate with trifluoroacetic acid provided cis-1-acetyl-4-[({4-[(2-methylquinolin-4-yl)methoxy]phenyl}sulfonyl)amino]pyrrolidine-3-carboxylic acid in quantitative yield. MS: 484.1 (M+H)+

Step 3

According to the procedure of example 17, Step 5, the reaction of 113.5 mg of cis-1-acetyl-4-[({4-[(2-methylquinolin-4-yl)methoxy]phenyl}sulfonyl)amino]pyrrolidine-3-carboxylic acid with hydroxylamine provided 39 mg (41% yield) of cis-1-acetyl-N-hydroxy-4-[({4-[(2-methylquinolin-4-yl)methoxy]phenyl}sulfonyl)amino]pyrrolidine-3-carboxamide. MS: 499.2 (M+H)+

Example 20 cis-1-Formyl-N-hydroxy-4-[({4-[(2-methylquinolin-4-yl)methoxy]phenyl}sulfonyl)amino]pyrrolidine-3-carboxamide

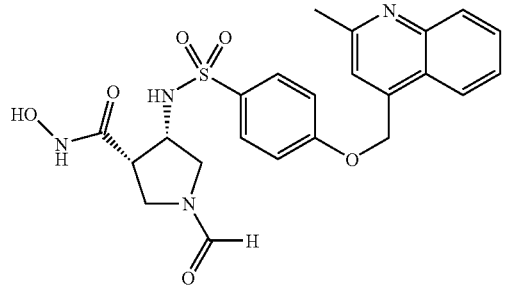

Step 1

According to the procedure of Example 17, Step 3, the reaction of 320.4 mg of tert-butyl cis-4-[({4-[(2-methylquinolin-4-yl)methoxy]phenyl}sulfonyl)amino]pyrrolidine-3-carboxylate hydrochloride with ethyl formate provided 191 mg (61% yield) of tert-butyl cis-1-formyl-4-[({4-[(2-methylquinolin-4-yl)methoxy]phenyl}sulfonyl)amino]pyrrolidine-3-carboxylate. MS: 526.2(M+H)+

Step 2

According to the procedure of Example 17, Step 4, the reaction of 168 mg of tert-butyl cis-1-formyl-4-[({4-[(2-methylquinolin-4-yl)methoxy]phenyl}sulfonyl)amino]pyrrolidine-3-carboxylate with trifluoroacetic acid provided cis-1-formyl-4-[({4-[(2-methylquinolin-4-yl)methoxy]phenyl}sulfonyl)amino]pyrrolidine-3-carboxylic acid in quantitative yield. MS: 470.1 (M+H)+

Step 3

According to the procedure of Example 17, Step 5, the reaction of 175 mg of cis-1-formyl-4-[({4-[(2-methylquinolin-4-yl)methoxy]phenyl}sulfonyl)amino]pyrrolidine-3-carboxylic acid with hydroxylamine provided 76 mg (52% yield) of cis-1-formyl-N-hydroxy-4-[({4-[(2-methylquinolin-4-yl)methoxy]phenyl}sulfonyl)amino]pyrrolidine-3-carboxamide. MS: 485.2 (M+H)+

Example 21 tert-Butyl cis-3-[(hydroxyamino)carbonyl]-4-[({4-[(2-methylquinolin-4-yl)methoxy]phenyl}sulfonyl)amino]pyrrolidine-1-carboxylate

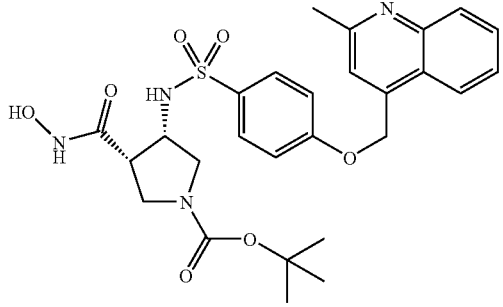

Step 1

To the stirred solution of 299 mg of di-tert-butyl cis-4-[({4-[(2-methylquinolin-4-yl)methoxy]phenyl}sulfonyl)amino]pyrrolidine-1,3-dicarboxylate (Example 17, Step 1) in 4 mL of dichloromethane was slowly added 3 mL of trifluoroacetic acid. The solution was stirred at room temperature for 3 hr. After removal of the volatile material, cis-4-[({4-[(2-methylquinolin-4-yl)methoxy]phenyl}sulfonyl)amino]pyrrolidine-3-carboxylic acid was obtained in quantitative yield without further purification. MS: 442.3 (M+H)$^+$

Step 2

According to the procedure of Example 17, Step 3, the reaction of 278 mg of cis-4-[({4-[(2-methylquinolin-4-yl)methoxy]phenyl}sulfonyl)amino]pyrrolidine-3-carboxylic acid with 218 mg of di-tert-butyl dicarbonate provided 148.1 mg (55% yield) of cis-1-(tert-butoxycarbonyl)-4-[({4-[(2-methylquinolin-4-yl)methoxy]phenyl}sulfonyl)amino]pyrrolidine-3-carboxylic acid. MS: 542.1 (M+H)$^+$

Step 3

According to the procedure of Example 17, Step 5, the reaction of 122 mg of cis-1-(tert-butoxycarbonyl)-4-[({4-[(2-methylquinolin-4-yl)methoxy]phenyl}sulfonyl)amino]pyrrolidine-3-carboxylic acid with hydroxylamine provided 104 mg (81% yield) of tert-butyl cis-3-[(hydroxyamino)carbonyl]-4-[({4-[(2-methylquinolin-4-yl)methoxy]phenyl}sulfonyl)amino]pyrrolidine-1-carboxylate. MS: 557.3 (M+H)$^+$

Example 22 cis-N-Hydroxy4-[({4-[(2-methylquinolin-4-yl)methoxy]phenyl}sulfonyl)amino]pyrrolidine-3-carboxamide

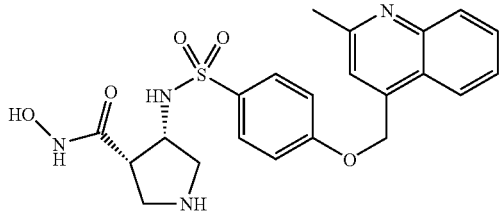

To the stirred solution of 74 mg of tert-butyl cis-3-[(hydroxyamino)carbonyl]-4-[({4-[(2-methylquinolin-4-yl)methoxy]phenyl}sulfonyl)amino]pyrrolidine-1-carboxylate in 4 mL of dichloromethane was slowly added 2 mL of trifluoroacetic acid. The solution was stirred at room temperature for 3 hr. After removal of the volatile material in vacuo cis-N-hydroxy-4-[({4-[(2-methylquinolin-4-yl)methoxy]phenyl}sulfonyl)amino]pyrrolidine-3-carboxamide was obtained in quantitative yield. MS: 457.0 (M+H)$^+$

Example 23 cis-1-Ethyl-N-hydroxy-4-[({4-[(2-methylquinolin-4-yl)methoxy]phenyl}sulfonyl)amino]pyrrolidine-1,3-dicarboxamide

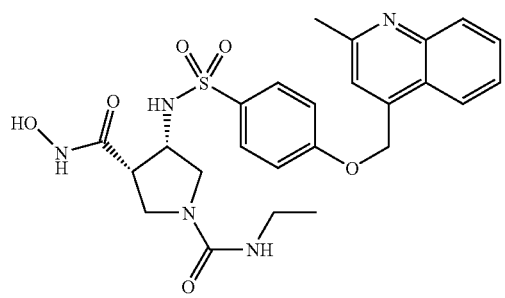

Step 1

According to the procedure of Example 17, Step 3, the reaction of 178 mg of cis-4-[({4-[(2-methylquinolin-4-yl)methoxy]phenyl}sulfonyl)amino]pyrrolidine-3-carboxylic acid (Example 21, Step 1) and 44 mg of ethyl isocyanate provided 175 mg of cis-1-[(ethylamino)carbonyl]-4-[({4-[(2-methylquinolin-4-yl)methoxy]phenyl}sulfonyl)amino]pyrrolidine-3-carboxylic acid in quantitative yield. MS: 513.2 (M+H)$^+$

Step 2

According to the procedure of Example 17, Step 5, the reaction of 120 mg of cis-1-[(ethylamino)carbonyl]-4-[({4-[(2-methylquinolin-4-yl)methoxy]phenyl}sulfonyl)amino]pyrrolidine-3-carboxylic acid and hydroxylamine provided 31 mg (31% yield) of cis-1-ethyl-N-hydroxy-4-[({4-[(2-methylquinolin-4-yl)methoxy]phenyl}sulfonyl)amino]pyrrolidine-1,3-dicarboxamide. MS: 528.2 (M+H)$^+$

Example 24

(3S,4R)-4-[4-(2-Methyl-quinolin-4-ylmethoxy)-benzenesulfonylamino]-tetrahydro-pyran-3-carboxylic acid hydroxyamide

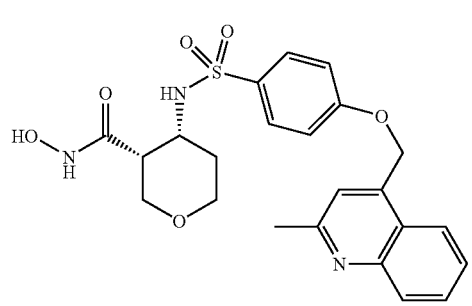

49

Step 1

To a mixture of 0.5 g (2.79 mmol) of 4-amino-tetrahydro-pyran-3-carboxylic acid methyl ester [WO 01/70673, Example 207] and 4-(2-methyl-quinolin-4-ylmethoxy)-benzenesulfonyl chloride hydrochloride (1.0 g, 2.94 mmol) in N,N-dimethylformamide (10 mL) was added N,N-diisopropylethylamine (1.02 mL, 5.88 mmol) at 0° C. The solution was allowed to warm to 25° C. over 19 h. The DMF was removed in vacuo and the resulting solid was partitioned between ethyl acetate (100 mL) and water (30 mL). The aqueous layer was washed with ethyl acetate (2×50 mL). ). The organic layer was dried over $MgSO_4$, filtered and concentrated to obtain a crude oil (1.48 g). The crude product was purified by Biotage Flash 40M chromatography, eluting with 1:4 ethyl acetate-hexanes, to afford 4-[4-(2-methyl-quinolin-4-ylmethoxy)-benzenesulfonylamino]-tetrahydro-pyran-3-carboxylic acid methyl ester as a white solid (1.08 g, 78%). MS: 471 $(M+H)^+$ Step 2

A solution of 4-[4-(2-methyl-quinolin-4-ylmethoxy)-benzenesulfonylamino]-tetrahydro-pyran-3-carboxylic acid methyl ester (0.3 g, 0.64 mmol) and lithium hydroxide (0.153 g, 6.38 mmol) in THF:methanol:$H_2O$ (2.5: 1.5:1.5 mL) was stirred at 25° C. for 19 h. The solution was diluted with ethyl acetate (2×30 mL) and the aqueous layer was acidified with 2N HCl to pH ~2. The aqueous layer was washed with ethyl acetate (3×40 mL). The combined organic layers were dried over $MgSO_4$, filtered and concentrated to provide 4-[4-(2-methyl-quinolin-4-ylmethoxy)-benzenesulfonylamino]-tetrahydro-pyran-3-carboxylic acid as a crude solid (0.280 g, 97%). MS: 457 $(M+H)^+$.

Step 3

To a solution of 4-[4-(2-methyl-quinolin-4-ylmethoxy)-benzenesulfonylamino]-tetrahydro-pyran-3-carboxylic acid (0.280 g, 0.658 mmol) and 1-hydroxybenzotriazole (HOBT, 0.177 g, 1.32 mmol) in DMF (10 mL) was added 1-(3-dimethylamino)propyl)-3-ethylcarbodiimide hydrochloride (0.253 g, 1.32 mmol) at 0° C. The reaction mixture stirred at 0° C. for 10 min, then warmed to 25° C. over 1 h. After recooling the reaction to 0° C. hydroxylamine (50% by wt in water, 0.6 mL, 6.6 mmol) was added. The reaction was allowed to warm to 25° C. over 19 h. The DMF was removed in vacuo and the resulting oil was diluted with ethyl acetate (100 mL) and this mixture was then washed with saturated aqueous sodium bicarbonate (3×30 mL) and brine (30 mL). The organic layer was dried over $MgSO_4$, filtered and concentrated to obtain a crude solid (0.170 g) which was purified by Biotage Flash 40S chromatography, eluting with 4% methanol in ethyl acetate, to afford (3S,4R)-4-[4-(2-methyl-quinolin-4-ylmethoxy)-benzenesulfonylamino]-tetrahydro-pyran-3-carboxylic acid hydroxyamide as an amorphous white solid (0.02 g, 6.6%) that was a 75.7:24.3 mixture of enantiomers, as determined by analytical chiral HPLC (Chiralpak IA column, 7:3 n-propanol/heptane, 1 mL/min, 254 nm). MS: 472 $(M+H)^+$

50

Example 25

(3S,4R)-4-{Methyl-[4-(2-methyl-quinolin-4-ylmethoxy)-benzenesulfonyl]-amino}-tetrahydro-pyran-3-carboxylic acid hydroxyamide

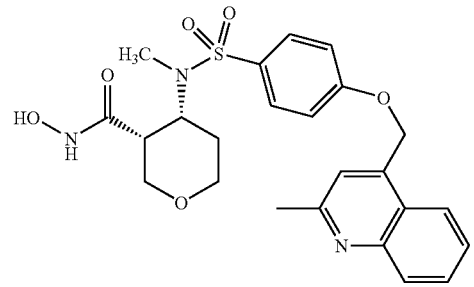

Step 1

To a slurry of 0.3 g (0.634 mmol) of 4-[4-(2-methyl-quinolin-4-ylmethoxy)-benzenesulfonylamino]-tetrahydro-pyran-3-carboxylic acid methyl ester (Example 24, Step 1) and potassium carbonate (0.176 g, 1.27 mmol) in DMF (10 mL) was added iodomethane (0.109 g, 0.765 mmol). The reaction was heated at 40° C. for 2 h and then the reaction was allowed to cool to 25° C. over 19 h. The DMF was removed in vacuo and the resulting oil was diluted with ethyl acetate (100 mL) and then washed with water (2×30 mL) and saturated aqueous sodium chloride (30 mL). The organic layer was dried over $MgSO_4$, filtered and concentrated to obtain a crude oil (0.170 g,). The crude product was purified by Biotage Flash 40S chromatography, eluting with 1:1 ethyl acetate:hexanes, to afford 4-{methyl-[4-(2-methyl-quinolin-4-ylmethoxy)-benzenesulfonyl]-amino}-tetrahydro-pyran-3-carboxylic acid methyl ester as an amorphous white solid (0.210 g, 68%). MS: 485 $(M+H)^+$.

Step 2

A solution of 4-{methyl-[4-(2-methyl-quinolin-4-ylmethoxy)-benzenesulfonyl]-amino}-tetrahydro-pyran-3-carboxylic acid methyl ester (0.2 g, 0.41 mmol) and lithium hydroxide (0.148 g, 4.1 mmol) in THF:methanol:$H_2O$ (2.5: 1.5:1.5 mL) was stirred at 25° C. for 19 h. The solution was then diluted with ethyl acetate (2×30 mL) and the aqueous layer was acidified with 2N HCl to pH ~2. The aqueous layer was washed with ethyl acetate (3×40 mL). The combined organic layers were dried over $MgSO_4$, filtered and concentrated to produce 4-{methyl-[4-(2-methyl-quinolin-4-ylmethoxy)-benzenesulfonyl]-amino}-tetrahydro-pyran-3-carboxylic acid as a crude solid (0.120 g, 63%). MS: 457 $(M+H)^+$.

Step 3

According to the procedure of Example 24, Step 3, 4-{methyl-[4-(2-methyl-quinolin-4-ylmethoxy)-benzenesulfonyl]-amino}-tetrahydro-pyran-3-carboxylic acid (0.120 g, 0.255 mmol) and hydroxylamine provided (3S,4R)-4-{methyl-[4-(2-methyl-quinolin-4-ylmethoxy)-benzenesulfonyl]-amino}-tetrahydro-pyran-3-carboxylic acid hydroxyamide as an amorphous white solid (0.050 g, 40%) after purification by Biotage Flash 40S chromatography, eluting with 4% methanol in ethyl acetate. MS: 486 $(M+H)^+$.

Example 26

(3S,4R)-4-[4-(2-Methyl-quinolin-4-ylmethoxy)-benzenesulfonylamino]-tetrahydro-furan-3-carboxylic acid hydroxyamide

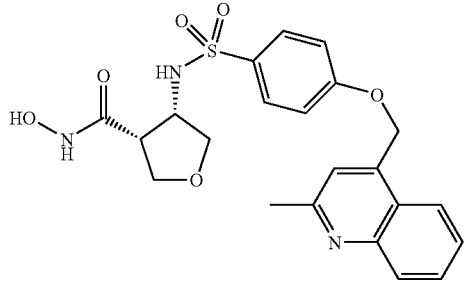

Step 1

To a slurry of 2.0 g (13.77 mmol) of 4-amino-tetrahydro-furan-3-carboxylic acid methyl ester [WO 01/70673, Examples 46, 58] and 4-(2-methyl-quinolin-4-ylmethoxy)-benzenesulfonyl chloride hydrochloride (5.13 g, 15.15 mmol) in $CH_2Cl_2$ (20 mL) was added saturated aqueous $NaHCO_3$ (20 mL) at 0° C. The solution was allowed to warm to 25° C. over 19 h. The reaction was then diluted with $CH_2Cl_2$ (100 mL) and water (30 mL). The organic layer was washed with water (2×50 mL) and then dried over $MgSO_4$, filtered and concentrated to obtain a crude oil (5.13 g). The crude product was purified by Biotage Flash 40M chromatography, eluting with 1:1 ethyl acetate-hexanes, to afford 4-[4-(2-methyl-quinolin-4-ylmethoxy)-benzenesulfonylamino]-tetrahydro-furan-3-carboxylic acid methyl ester as a white solid (2.3 g, 38%). MS: 457 $(M+H)^+$

Step 2

To a solution of 4-[4-(2-methyl-quinolin-4-ylmethoxy)-benzenesulfonylamino]-tetrahydro-furan-3-carboxylic acid methyl ester (0.9 g, 1.97 mmol) in 1,4-dioxane (4 mL) was added concentrated HCl (4 mL). The reaction was heated to 60° C. for 19 h. The solvent was removed in vacuo to provide 4-[4-(2-methyl-quinolin-4-ylmethoxy)-benzenesulfonylamino]-tetrahydro-furan-3-carboxylic acid as a crude solid (0.6 g, 69%). MS: 443 $(M+H)^+$

Step 3

According to the procedure of Example 24, Step 3, 4-[4-(2-methyl-quinolin-4-ylmethoxy)-benzenesulfonylamino]-tetrahydro-furan-3-carboxylic acid (0.6 g, 1.35 mmol) and hydroxylamine afforded (3S,4R)-4-[4-(2-methyl-quinolin-4-ylmethoxy)-benzenesulfonylamino]-tetrahydro-furan-3-carboxylic acid hydroxyamide as an amorphous white solid (0.07 g, 11%) after HPLC purification, eluting with acetonitrile:water. MS: 458 $(M+H)^+$

Example 27

(3S,4R)-4-{Methyl-[4-(2-methyl-quinolin-4-ylmethoxy)-benzenesulfonyl]-amino}-tetrahydro-furan-3-carboxylic acid hydroxyamide

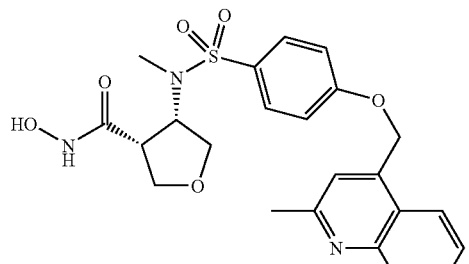

Step 1

To a slurry of 0.3 g (0.658 mmol) of 4-[4-(2-methyl-quinolin-4-ylmethoxy)-benzenesulfonylamino]-tetrahydro-furan-3-carboxylic acid methyl ester (Example 26, Step 1) and potassium carbonate (0.182 g, 1.32 mmol) in DMF (10 mL) was added iodomethane (0.103 g, 0.723 mmol). The reaction was stirred at 25° C. for 19 h. The DMF was removed in vacuo and the resulting oil was diluted with ethyl acetate (100 mL). The organics were washed with water (2×30 mL) and saturated aqueous sodium chloride (30 mL). The organic layer was dried over $MgSO_4$, filtered and concentrated to provide a crude oil (0.42 g) that was purified by Biotage Flash 40S chromatography, eluting with 2:1 ethyl acetate:hexanes, to afford 4-{methyl-[4-(2-methyl-quinolin-4-ylmethoxy)-benzenesulfonyl]-amino}-tetrahydro-furan-3-carboxylic acid methyl ester as an amorphous white solid (0.270 g, 87%). MS: 471 $(M+H)^+$.

Step 2

A solution of 4-{methyl-[4-(2-methyl-quinolin-4-ylmethoxy)-benzenesulfonyl]-amino}-tetrahydro-furan-3-carboxylic acid methyl ester (0.160 g, 0.3 mmol) and lithium hydroxide (0.082 g,. 3.4 mmol) in THF:methanol:water (3:2:2 mL) was stirred at 25° C. for 19 h. The solution was then washed with ethyl acetate (2×30 mL) and the aqueous layer was acidified with 2N HCl to pH ~2. The aqueous layer was washed with ethyl acetate (3×40 mL). The combined organic layers were dried over $MgSO_4$, filtered and concentrated to produce 4-{methyl-[4-(2-methyl-quinolin-4-ylmethoxy)-benzenesulfonyl]-amino}-tetrahydro-furan-3-carboxylic acid as a crude solid (0.160 g, 100%). MS: 457 $(M+H)^+$

Step 3

According to the procedure of Example 24, Step 3, 4-{methyl-[4-(2-methyl-quinolin-4-ylmethoxy)-benzenesulfonyl]-amino}-tetrahydro-furan-3-carboxylic acid (0.160 g, 0.35 mmol) and hydroxylamine gave (3S,4R)-4-{methyl-[4-(2-methyl-quinolin-4-ylmethoxy)-benzenesulfonyl]-amino}-tetrahydro-furan-3-carboxylic acid hydroxyamide as an amorphous white solid (0.035 g, 21%) after purification using Biotage Flash 40S chromatography, eluting with 5% methanol in ethyl acetate. MS: 472 $(M+H)^+$

Example 28 tert-Butyl (3S,4R)-3-[(hydroxyamino)carbonyl]-4-[({4-[(2-methylquinolin-4-yl)methoxy]phenyl}sulfonyl)amino]piperidine-1-carboxylate

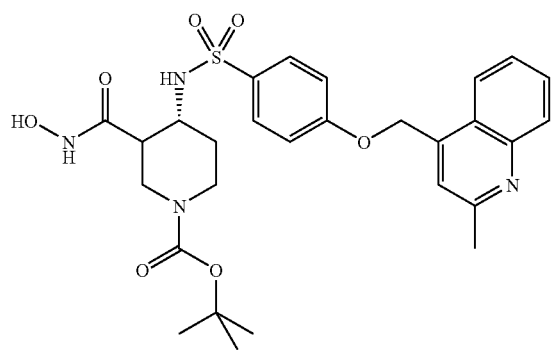

Step 1

To a solution of 1-benzyl-4-oxo-piperidine-3-carboxylic acid methyl ester (15.0 g, 52.86 mmol) in benzene (150 mL) was added R-alpha-methylbenzylamine (7.18 mL, 58.15 mL) and ytterbium (III) triflate (1 g) and the resulting mixture was heated to reflux under Dean-Stark conditions for 3 h. Then an additional 0.5 mL of R-alpha-methylbenzylamine was added and the reaction was heated for 1 h further. The reaction was cooled to 25° C. and the crude product was purified by Biotage Flash 40M chromatography, eluting with 1:9 ethyl acetate-hexanes, to afford 4-(1-phenyl-ethyl amino)-1-(2-vinyl-but-2-enyl)-1,2,5,6-tetrahydro-pyridine-3-carboxylic acid methyl ester as an orange amorphous solid (18 g, 100%). MS: 351 (M+H)$^+$

Step 2

A mixture of 4-(1-phenyl-ethyl amino)-1-(2-vinyl-but-2-enyl)-1,2,5,6-tetrahydro-pyridine-3-carboxylic acid methyl ester (6.0 g, 17.02 mmol) and 20% palladium hydroxide on carbon (2 g) in methanol (20 mL) was stirred under a hydrogen balloon for 19 h. The mixture was then filtered through a thin pad of celite and concentrated to provide 4-(1-phenyl-ethylamino)-1,2,5,6-tetrahydro-pyridine-3-carboxylic acid methyl ester as a colorless oil (4.5 g, 90%). MS: 261 (M+H)$^+$.

Step 3

To a 0° C. solution of 4-(1-phenyl-ethylamino)-1,2,5,6-tetrahydro-pyridine-3-carboxylic acid methyl ester (4.5 g, 17.28 mmol) in THF (50 mL) was added Hunig's base and di-tert-butyl dicarbonate (4.5 g, 20.79 mmol), as a solution in THF (5 mL). The reaction was allowed to warm to 25° C. over 19 h and then saturated aqueous sodium bicarbonate (20 mL) was added. The mixture was washed with water (2×30 mL) and brine (30 mL). The organic layer was dried over MgSO$_4$, filtered and concentrated in vacuo. The crude product was purified by Biotage Flash 40M chromatography, eluting with ethyl acetate-hexanes (1:2), to afford 4-(1-phenyl-ethylamino)-5,6-dihydro-2H-pyridine-1,3-dicarboxylic acid 1-tert-butyl ester 3-methyl ester as an amorphous off white solid (4.1 g, 66%). MS: 361 (M+H)$^+$

Step 4

A solution of 4-(1-phenyl-ethyl amino)-5,6-dihydro-2H-pyridine-1,3-dicarboxylic acid 1-tert-butyl ester 3-methyl ester (4 g, 11.1 mmol) in acetic acid-acetonitrile (1:1, 80 mL) was treated with sodium triacetoxyborohydride (2.59 g, 12.2 mmol), and stirred for 5 h at 0° C. The reaction was cooled to 0° C. and neutralized with saturated aqueous sodium bicarbonate (5 mL). The organic layer was washed with brine (3×20 mL), then dried over MgSO$_4$, filtered and concentrated to obtain a crude oil (3.6 g). The crude product was purified by Biotage Flash 40S chromatography, eluting with 1:1 ethyl acetate-hexanes, to provide 4-(1-phenyl-ethylamino)-piperidine-1,3-dicarboxylic acid 1-tert-butyl ester 3-methyl ester as a white solid (2.5 g, 62.5%). MS: 363 (M+H)$^+$

Step 5

A mixture of 4-(1-phenyl-ethylamino)-piperidine-1,3-dicarboxylic acid 1-tert-butyl ester 3-methyl ester (2.4 g, 6.62 mmol) and 20% palladium hydroxide on carbon (1 g) in methanol (20 mL) was stirred under a hydrogen balloon for 19 h. The mixture was then filtered through a thin pad of celite and concentrated to provide 4-amino-piperidine-1,3-dicarboxylic acid 1-tert-butyl ester 3-methyl ester as a colorless oil (1.3 g, 81.2%) MS: 259 (M+H)$^+$.

Step 6

To a mixture of 4-amino-piperidine-1,3-dicarboxylic acid 1-tert-butyl ester 3-methyl ester (1.3 g, 5 mmol] and 4-(2-methyl-quinolin-4-ylmethoxy)-benzenesulfonyl chloride hydrochloride (1.9 g, 5.50 mmol) in CH$_2$Cl$_2$ (20 mL) was added saturated aqueous NaHCO$_3$ (20 mL) at 0° C. The solution was allowed to warm to 25° C. over 19 h. The reaction was then further diluted in CH$_2$Cl$_2$ (100 mL) and water (30 mL). The organic layer was washed with water (2×50 mL). The organic layer was dried over MgSO$_4$, filtered and concentrated to provide a crude oil (2.6 g). The crude product was purified by Biotage Flash 40M chromatography, eluting with 1:1 ethyl acetate-hexanes, to afford 4-[4-(2-methyl-quinolin-4-ylmethoxy)-benzenesulfonylamino]-piperidine-1,3-dicarboxylic acid 1-tert-butyl ester 3-methyl ester as a white solid (1.6 g, 55%). MS: 570 (M+H)$^+$

Step 7

A solution of 4-[4-(2-methyl-quinolin-4-ylmethoxy)-benzenesulfonylamino]-piperidine-1,3-dicarboxylic acid 1-tert-butyl ester 3-methyl ester (0.3 g, 0.525 mmol) and lithium hydroxide (0.1 g, 4.2 mmol) in THF:methanol:water (2.5:1.5:1.5 mL) was stirred at 25° C. for 19 h. The solution was concentrated in vacuo to provide 4-[4-(2-methyl-quinolin-4-ylmethoxy)-benzenesulfonylamino]-piperidine-1,3-dicarboxylic acid 1-tert-butyl ester as a crude solid (0.170 g, 58%). MS: 557 (M+H)$^+$

Step 8

According to the procedure of Example 24, Step 3, 4-[4-(2-methyl-quinolin-4-ylmethoxy)-benzenesulfonylamino]-piperidine-1,3-dicarboxylic acid 1-tert-butyl ester (0.17 g, 0.30 mmol) and hydroxylamine gave a 7:1 mixture of cis- and trans-tert-Butyl (3S,4R)-3-[(hydroxyamino)carbonyl]-4-[({4-[(2-methylquinolin-4-yl)methoxy]phenyl}sulfonyl)amino]piperidine-1-carboxylate as an amorphous white solid (0.025 g, 14.6%) after purification using Biotage Flash 40S chromatography, eluting with 5% methanol in ethyl acetate. Mass Spectrum Found: 571 (M+H)$^+$

Example 29

(3S,4R)-1-Formyl-4-[4-(2-methyl-quinolin-4-yl-methoxy)-benzenesulfonylamino]-piperidine-3-carboxylic acid hydroxyamide

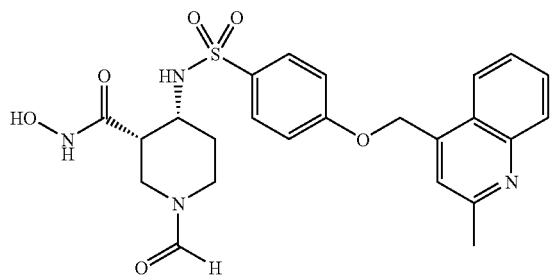

Step 1
To a solution of 0.3 g (0.525 mmol) of 4-[4-(2-methyl-quinolin-4-ylmethoxy)-benzenesulfonylamino]-piperidine-1,3-dicarboxylic acid 1-tert-butyl ester 3-methyl ester (Example 28, Step 6) in 1,4-dioxane (4 mL) was added concentrated HCl (4 mL). The reaction was heated to 60° C. for 19 h. The solvent was then removed in vacuo to give (3S,4R)-4-[4-(2-methyl-quinolin-4-ylmethoxy)-benzenesulfonylamino]-piperidine-3-carboxylic acid as the hydrochloride salt (0.210 g, 72.4%). MS: 457 (M+H)$^+$

Step 2
To a solution of 4-[4-(2-methyl-quinolin-4-ylmethoxy)-benzenesulfonylamino]-piperidine-3-carboxylic acid (0.210 g, 0.459 mmol) and 1-hydroxybenzotriazole (HOBT, 0.186 g, 1.38 mmol) in DMF (10 mL) was added 1-[3-(dimethylamino)propyl]-3-ethylcarbodiimide hydrochloride (0.264 g, 1.38 mmol) at 0° C. The reaction mixture stirred at 0° C. for 10 min, then warmed to 25° C. over 1.0 h. After re-cooling the reaction to 0° C., hydroxylamine (50% by wt in water solution, 0.5 mL, 4.6 mmol) was added. The reaction was allowed to warm to 25° C. over 19 h and then formic acid (0.151 g, 3.2 mmol) added. The reaction was stirred for 10 min at 25° C. and 40° C. for 30 min and then allowed to warm to 25° C. over 19 h. The DMF was removed in vacuo and the resulting oil was diluted in ethyl acetate (100 mL) and then washed with saturated aqueous sodium bicarbonate (3×30 mL) and brine (30 mL). The organic layer was dried over MgSO$_4$, filtered and concentrated to obtain a crude solid (0.195 g). The crude product was purified by reverse phase HPLC (Gilson) on a Phenomex C-18 semi-prep column eluting with an acetonitrile:water gradient, to afford (3S,4R)-1-formyl-4-[4-(2-methyl-quinolin-4-ylmethoxy)-benzenesulfonyl amino]-piperidine-3-carboxylic acid hydroxyamide as an amorphous white solid (0.025 g, 11.6%). MS: 499 (M+H)$^+$

Example 30

(3S,4R)-4-[4-(2-Methyl-quinolin-4-ylmethoxy)-benzenesulfonylamino]-piperidine-1,3-dicarboxylic acid 1-tert-butylamide 3-hydroxyamide

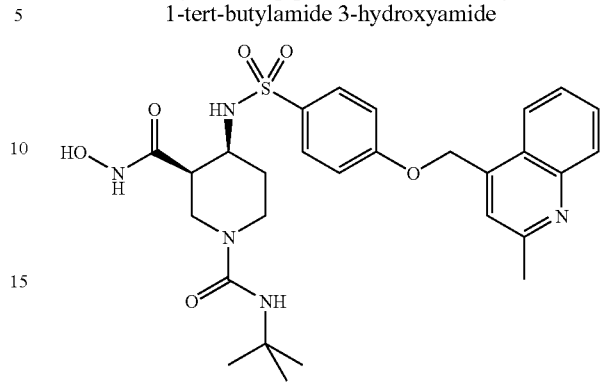

Step 1
To a solution of 0.5 g (1.1 mmol) of 4-[4-(2-methyl-quinolin-4-ylmethoxy)-benzenesulfonylamino]-piperidine-3-carboxylic acid (Example 29, Step 1) and triethylamine (0.3 mL, 2.197 mmol) in THF (10 mL) at 0° C. was added tert-butyl-isocyanate (0.130 g, 1.32 mmol). The reaction mixture was allowed to warm to 25° C. and then stirred for 19 h. The THF was removed in vacuo and the resulting oil was diluted with ethyl acetate (100 mL). The organics were washed with saturated aqueous sodium chloride (2×30 mL), dried over MgSO$_4$, filtered and concentrated to obtain a crude solid (0.580 g). The crude product was purified by reverse phase HPLC (Gilson) on a Phenomex C-18 semi-prep column eluting an acetonitrile:water gradient, to afford (3S,4R)-1-tert-butylcarbamoyl-4-[4-(2-methyl-quinolin-4-yl methoxy)-benzenesulfonylamino]-piperidine-3-carboxylic acid as an amorphous white solid (0.5 g, 88.5%). MS: 555 (M+H)$^+$.

Step 2
According to the procedure of Example 24, Step 3, 0.5 g (0.9 mmol) of 1-tert-butylcarbamoyl-4-[4-(2-methyl-quinolin-4-yl methoxy)-benzenesulfonylamino]-piperidine-3-carboxylic acid and hydroxylamine provided (3S,4R)-4-[4-(2-methyl-quinolin -4-ylmethoxy)-benzenesulfonyl amino]-piperidine-1,3-dicarboxylic acid 1-tert-butylamide-3-hydroxyamide as an amorphous white solid (0.025 g, 11.6%) after reverse phase HPLC (Gilson) on a Phenomex C-18 semi-prep column eluting with an acetonitrile:water gradient.MS: 570 (M+H)$^+$.

Example 31

1-Acetyl-4-[4-(2-methyl-quinolin-4-ylmethoxy)-benzenesulfonylamino]-piperidine-3-carboxylic acid hydroxyamide

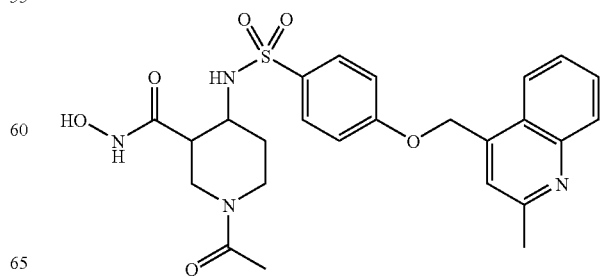

Step 1

4-[4-(2-Methyl-quinolin-4-ylmethoxy)-benzenesulfonylamino]-piperidine-1,3-dicarboxylic acid 1-tert-butyl ester 3-ethyl ester was prepared analogously to the methyl ester (Example 28, Step 6) starting from 1-benzyl-4-oxo-piperidine-3-carboxylic acid ethyl ester. To a solution of 0.9 g (1.54 mmol) of 4-[4-(2-methyl-quinolin-4-ylmethoxy)-benzenesulfonylamino]-piperidine-1,3-dicarboxylic acid 1-tert-butyl ester 3-ethyl ester in $CH_2Cl_2$ (1 mL) at 0° C. was added $CH_2Cl_2$:TFA (1:1, 10 mL). The reaction mixture was stirred at 25° C. for 3 h. The solvent was removed in vacuo to give the trifluoroacetic acid salt of 4-[4-(2-methyl-quinolin-4-ylmethoxy)-benzenesulfonylamino]-piperidine-3-carboxylic acid ethyl ester as an amorphous white solid (0.6 g, 80.3%). MS: 484 $(M+H)^+$.

Step 2

To a solution of 4-[4-(2-methyl-quinolin-4-ylmethoxy)-benzenesulfonylamino]-piperidine-3-carboxylic acid ethyl ester (0.6 g, 1.24 mmol) in $CH_2Cl_2$ (10 mL) and TEA (0.378 mL, 2.73 mmol) at 0° C. was added acetyl chloride (0.1 mL, 1.36 mmol). The reaction was allowed to warm to 25° C. over 19 h. The reaction was then taken up in $CH_2Cl_2$ (50 mL) and washed with 1N HCl (5 mL) and water (5 mL). The organics were washed with saturated aqueous sodium chloride (30 mL), dried over $MgSO_4$, filtered and concentrated. The residue was purified with Biotage Flash 40S chromatography, eluting with 1:1 ethyl acetate-hexanes, to provide 1-acetyl-4-[4-(2-methyl-quinolin-4-ylmethoxy)-benzenesulfonylamino]-piperidine-3-carboxylic acid ethyl ester as a white solid (0.6 g, 92%). MS: 526 $(M+H)^+$.

Step 3

To a solution of 1-acetyl-4-[4-(2-methyl-quinolin-4-ylmethoxy)-benzenesulfonylamino]-piperidine-3-carboxylic acid ethyl ester (0.6 g, 1.14 mmol) in 1,4-dioxane (10 mL) was added concentrated HCl (10 mL). The reaction was heated at 60° C. for 19 h. The solvent was removed in vacuo and the residue was diluted with $CH_2Cl_2$. The organics were dried over $MgSO_4$, filtered and concentrated. The residue was purified by reverse phase HPLC (Gilson) on a Phenomex C-18 semi-prep column eluting an acetonitrile:water gradient, to afford 1-acetyl-4-[4-(2-methyl-quinolin-4-ylmethoxy)-benzenesulfonylamino]-piperidine-3-carboxylic acid as an amorphous white solid (0.4 g, 70.1%). MS: 498 $(M+H)^+$.

Step 4

According to the procedure of Example 24, Step 3, 0.4 g (0.8 mmol) of 4-[4-(2-methyl-quinolin-4-ylmethoxy)-benzenesulfonylamino]-piperidine-3-carboxylic acid and hydroxylamine afforded an ~1:1 mixture of cis- and trans-1-acetyl-4-[4-(2-methyl-quinolin-4-ylmethoxy)-benzene sulfonyl amino]-piperidine-3-carboxylic acid hydroxyamide as an amorphous white solid (0.030 g, 7.3%) after purification by reverse phase HPLC (Gilson) on a Phenomex C-18 semi-prep column eluting an acetonitrile:water gradient. MS: 513 $(M+H)^+$.

Example 32

1-(2-Hydroxy-ethyl)-4-[4-(2-methyl-quinolin-4-ylmethoxy)-benzenesulfonylamino]-piperidine-3-carboxylic acid hydroxyamide

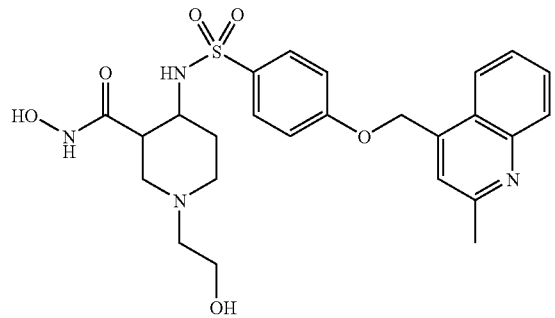

Step 1

To a solution of 0.6 g (1.24 mmol) of 4-[4-(2-methyl-quinolin-4-ylmethoxy)-benzenesulfonylamino]-piperidine-3-carboxylic acid ethyl ester (see Example 31, Step 1) in $CH_2Cl_2$ (10 mL) and TEA (0.313 mL, 3.1 mmol) at 0° C. was added 2-bromoethanol (0.1 mL, 1.36 mmol). The resulting reaction mixture was allowed to warm to 25° C. over 19 h. The reaction was then diluted with $CH_2Cl_2$ (50 mL) and washed with 1N HCl (5 mL) and saturated aqueous sodium chloride (30 mL). The organic layer was dried over $MgSO_4$, filtered and concentrated in vacuo. The residue was purified by Biotage Flash 40S chromatography, eluting with 2:1 ethyl acetate-hexanes, to provide 1-(2-hydroxy-ethyl)-4-[4-(2-methyl-quinolin-4-ylmethoxy)-benzenesulfonylamino]-piperidine-3-carboxylic acid ethyl ester as a white solid (0.6 g, 92%). MS: 528 $(M+H)^+$

Step 2

To a solution of 1-(2-hydroxy-ethyl)-4-[4-(2-methyl-quinolin-4-ylmethoxy)-benzenesulfonylamino]-piperidine-3-carboxylic acid ethyl ester (0.6 g, 1.14 mmol) in 1,4-dioxane (10 mL) was added concentrated HCl (10 mL). The reaction was heated to 60° C. for 19 h and the solvent was then removed in vacuo. The residue was purified by reverse phase HPLC (Gilson) on a Phenomex C-18 semi-prep column eluting with an acetonitrile:water gradient to afford 1-(2-hydroxy-ethyl)-4-[4-(2-methyl-quinolin-4-ylmethoxy)-benzenesulfonylamino]-piperidine-3-carboxylic acid as an amorphous white solid (0.4 g, 71.4%). MS: 500 $(M+H)^+$.

Step 3

According to the procedure of Example 24, Step 3, 0.4 g (0.8 mmol) of 1-(2-hydroxy-ethyl)-4-[4-(2-methyl-quinolin-4-ylmethoxy)-benzenesulfonylamino]-piperidine-3-carboxylic acid and hydroxylamine afforded a ~2:1 mixture of cis- and trans-1-(2-hydroxy-ethyl)-4-[4-(2-methyl-quinolin-4-ylmethoxy)-benzenesulfonylamino]-piperidine-3-carboxylic acid hydroxyamide as an amorphous white solid (0.040 g, 9.7%) after purification using reverse phase HPLC (Gilson) on a Phenomex C-18 semi-prep column eluting an acetonitrile:water gradient. MS: 515 $(M+H)^+$.

Example 33

(3S,4R)-4-Hydroxycarbamoyl-3-[4-(2-methyl-quinolin-4-ylmethoxy)-benzenesulfonylamino]-piperidine-1-carboxylic acid tert-butyl ester

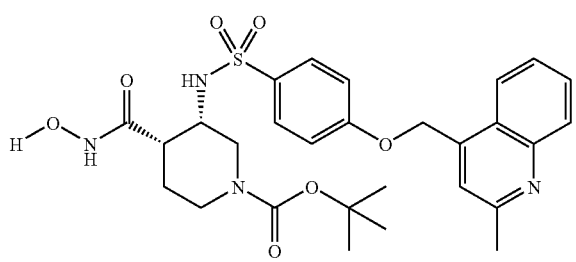

Step 1

To a mixture of 2.89 g (10.62 mmol) of 3-amino-piperidine-1,4-dicarboxylic acid 1-tert-butyl ester 4-ethyl ester [WO 01/70673, Example 134] and 4-(2-methyl-quinolin-4-ylmethoxy)-benzenesulfonyl chloride hydrochloride (4.0 g, 11.8 mmol) in CH₂Cl₂ (40 mL) at 0° C. was added saturated aqueous NaHCO₃ (40 mL). The solution was allowed to warm to 25° C. over 19 h. The reaction was then diluted with CH₂Cl₂ (100 mL) and water (30 mL), the organic layer was washed with water (2×50 mL), dried over MgSO₄, filtered and concentrated in vacuo. The residue was purified by Biotage Flash 40M chromatography, eluting with 1:2 ethyl acetate-hexanes, to afford 3-[4-(2-methyl-quinolin-4-ylmethoxy)-benzenesulfonylamino]-piperidine-1,4-dicarboxylic acid 1-tert-butyl ester 4-ethyl ester as a white solid (1.6 g, 25.8%). MS: 584 (M+H)⁺.

Step 2

A solution of 3-[4-(2-methyl-quinolin-4-ylmethoxy)-benzenesulfonylamino]-piperidine-1,4-dicarboxylic acid 1-tert-butyl ester 4-ethyl ester (0.6 g, 1.03 mmol) and lithium hydroxide (0.148 g, 6.18 mmol) in THF:methanol:water (3:2:2 mL) was stirred at 25° C. for 19 h. The solution was then concentrated in vacuo to provide 3-[4-(2-methyl-quinolin-4-ylmethoxy)-benzenesulfonylamino]-piperidine-1,4-dicarboxylic acid 1-tert-butyl ester as a crude solid (0.55 g, 96%). MS: 556 (M+H)⁺.

Step 3

According to the procedure of Example 24, Step 3, 0.55 g (0.99 mmol) of 3-[4-(2-methyl-quinolin-4-ylmethoxy)-benzenesulfonylamino]-piperidine-1,4-dicarboxylic acid 1-tert-butyl ester and hydroxylamine afforded 4-hydroxycarbamoyl-3-[4-(2-methyl-quinolin-4-yl methoxy)-benzenesulfonylamino]-piperidine-1-carboxylic acid tert-butyl ester as an amorphous white solid (0.030 g, 5.3%) after purification using reverse phase HPLC (Gilson) on a Phenomex C-18 semi-prep column, eluting an acetonitrile:water gradient. MS: 571 (M+H)⁺

Example 34

1-Formyl-3-[4-(2-methyl-quinolin-4-ylmethoxy)-benzenesulfonylamino]-piperidine-4-carboxylic acid hydroxyamide

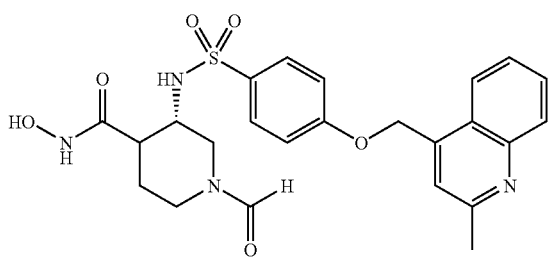

Step 1

To a solution of 0.6 g (1.02 mmol) of 4-[4-(2-methyl-quinolin-4-ylmethoxy)-benzenesulfonylamino]-piperidine-1,4-dicarboxylic acid 1-tert-butyl ester 4-methyl ester (prepared analogously to WO 01/70673, Example 134) in 1,4-dioxane (4 mL) was added concentrated HCl (4 mL). The reaction was heated to 60° C. for 19 h. The solvent was then removed in vacuo to give 3-[4-(2-methyl-quinolin-4-ylmethoxy)-benzenesulfonylamino]-piperidine-4-carboxylic acid as the hydrochloride salt (0.431 g, 93%). MS: 456 (M+H)⁺.

Step 2

According to the procedure of Example 29, Step 2, 0.4 g (0.878 mmol) of 4-[4-(2-methyl-quinolin-4-ylmethoxy)-benzenesulfonylamino]-piperidine-3-carboxylic acid hydroxylamine and formic acid gave a mixture of cis- and trans-1-formyl-3-[4-(2-methyl-quinolin-4-ylmethoxy)-benzenesulfonylamino]-piperidine-4-carboxylic acid hydroxyamide as an amorphous white solid (0.035 g, 8%) after reverse phase HPLC (Gilson) on a Phenomex C-18 semi-prep column, eluting with an acetonitrile:water gradient. MS: 499 (M+H)⁺

Example 35

3-[4-(2-Methyl-quinolin4-ylmethoxy)-benzenesulfonylamino]-piperidine-1,4-dicarboxylic acid 1-tert-butylamide 4-hydroxyamide

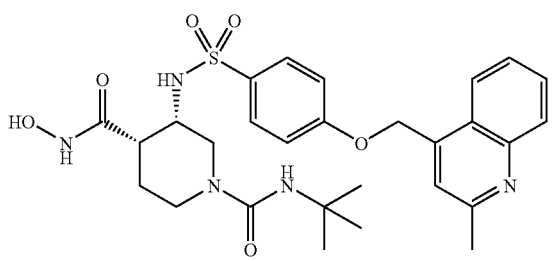

Step 1

To a solution of 0.2 g (0.44 mmol) of 3-[4-(2-methyl-quinolin-4-ylmethoxy)-benzenesulfonylamino]-piperidine-1,4-dicarboxylic acid 1-tert-butyl ester 4-ethyl ester [WO 01/70673, Example 134] in THF (10 mL) at 0° C. was added tert-butylisocyanate (0.130 g, 0.9 mmol). The reaction mixture stirred at 25° C. for 19 h and then the THF was removed in vacuo. The resulting oil was diluted with ethyl acetate (100 mL) and the organics were washed with saturated aqueous sodium chloride (2×30 mL), dried over MgSO₄, filtered and concentrated in vacuo. The residue was purified by reverse phase HPLC (Gilson) on a Phenomex C-18 semi-prep column, eluting with an acetonitrile:water gradient, to afford 3-[4-(2-methyl-quinolin-4-ylmethoxy)-benzenesulfonylamino]-piperidine-4-carboxylic acid as an amorphous white solid (0.23 g, 96%). MS: 556 (M+H)⁺.

Step 2

According to the procedure of Example 24, Step 3, 0.23 g (0.4 mmol) of 3-[4-(2-methyl-quinolin-4-ylmethoxy)-benzenesulfonylamino]-piperidine-4-carboxylic acid and hydroxylamine afforded 3-[4-(2-methyl-quinolin-4-ylmethoxy)-benzenesulfonylamino]-piperidine-1,4-dicarboxylic acid 1-tert-butylamide 4-hydroxyamide as an amorphous white solid (0.040 g, 17.6%) after reverse phase HPLC (Gilson) on a Phenomex C-18 semi-prep column eluting an acetonitrile:water gradient. MS: 570 (M+H)⁺

Example 36

1-Acetyl-3-[4-(2-methyl-quinolin-4-ylmethoxy)-benzenesulfonylamino]-piperidine-4-carboxylic acid hydroxyamide

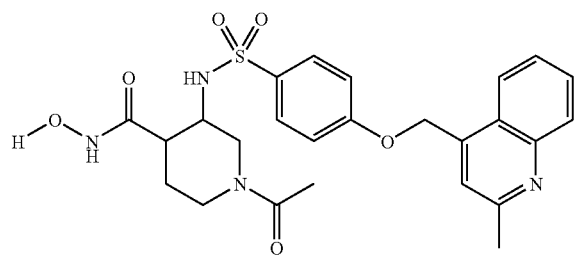

Step 1

To a solution of 0.98 g (1.67 mmol) of 3-[4-(2-methyl-quinolin-4-ylmethoxy)-benzenesulfonylamino]-piperidine-1,4-dicarboxylic acid 1-tert-butyl ester 4-ethyl ester [WO 01/70673, Example 134] in CH₂Cl₂ (10 mL) at 0° C. was added CH₂Cl₂:TFA (1:1, 10 mL). The reaction mixture was stirred at 25° C. for 3 h. The solvent was then removed in vacuo, to give the TFA salt of 3-[4-(2-methyl-quinolin-4-ylmethoxy)-benzenesulfonyl amino]-piperidine-4-carboxylic acid ethyl ester as an amorphous white solid (0.7 g, 86.7%). MS: 484 (M+H)⁺.

Step 2

To a solution of 4-[4-(2-methyl-quinolin-4-ylmethoxy)-benzenesulfonylamino]-piperidine-4-carboxylic acid ethyl ester (0.7 g, 1.44 mmol) in CH₂Cl₂ (10 mL) and TEA (0.4 mL, 2.89 mmol) at 0° C. was added acetyl chloride (0.113 mL, 1.59 mmol). The reaction was allowed to warm to 25° C. over 19 h. The reaction was then taken up in CH₂Cl₂ (50 mL) and washed with 1N HCl (5 mL) and water (5 mL). The organics were washed with saturated aqueous sodium chloride (30 mL), dried over MgSO₄, filtered and concentrated. The residue was purified by Biotage Flash 40S chromatography, eluting with 2:1 ethyl acetate-hexanes, to provide 1-acetyl-4-[4-(2-methyl-quinolin-4-ylmethoxy)-benzenesulfonylamino]-piperidine-4-carboxylic acid ethyl ester as a white solid (0.4 g, 53%). MS: 526 (M+H)⁺

Step 3

To a solution of 1-acetyl-4-[4-(2-methyl-quinolin-4-ylmethoxy)-benzenesulfonylamino]-piperidine-4-carboxylic acid ethyl ester (0.4 g, 7.6 mmol) in 1,4-dioxane (4 mL) was added concentrated HCl (4 mL). The reaction was heated to 60° C. for 19 h. The solvent was then removed in vacuo and the residue was purified by reverse phase HPLC (Gilson) on a Phenomex C-18 semi-prep column eluting an acetonitrile:water gradient, to afford 1-acetyl-4-[4-(2-methyl-quinolin-4-ylmethoxy)-benzenesulfonyl amino]-piperidine-4-carboxylic acid as an amorphous white solid (0.2 g, 63.1%). MS: 498 (M+H)⁺.

Step 4

According to the procedure of Example 24, Step 3, 0.2 g (0.4 mmol) of 4-[4-(2-methyl-quinolin-4-ylmethoxy)-benzenesulfonylamino]-piperidine-4-carboxylic acid and hydroxylamine afforded an ~1:1 mixture of cis- and trans-1-acetyl-4-[4-(2-methyl-quinolin-4-ylmethoxy)-benzene sulfonyl amino]-piperidine-4-carboxylic acid hydroxyamide as an amorphous white solid (0.035 g, 16.9%) after reverse phase HPLC (Gilson) on a Phenomex C-18 semi-prep column, eluting with an acetonitrile:water gradient. MS: 513 (M+H)⁺

Example 37 tert-Butyl 2-[(hydroxyamino)carbonyl]-3-[({4-[(2-methylquinolin-4-yl)methoxy]phenyl}sulfonyl)amino]-7-azabicyclo[2.2.1]heptane-7-carboxylate

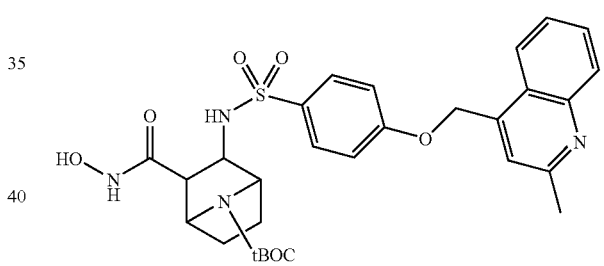

Step 1

To a solution of 7.0 g (25.89 mmol) of 3-oxo-7-aza-bicyclo[2.2.1]heptane-2,7-dicarboxylic acid 7-tert-butyl ester 2-methyl ester [J. Org. Chem. 61, 7189-7191 (1996)] in benzene (100 mL) was added R-alpha-methylbenzylamine (3.5 mL, 28.48 mL) and ytterbium (III) triflate (0.2 g). The resulting mixture was heated to reflux under Dean-Stark conditions for 3 h, and then treated with 0.5 mL of additional R-alpha-methylbenzylamine (0.5 mL) and heated 1 h further. The solution was then cooled to 25° C. and concentrated in vacuo. The residue was purified by Biotage Flash 40M chromatography, eluting with 1:6 ethyl acetate-hexanes, to afford 3-(1-phenyl-ethylamino)-7-aza-bicyclo[2.2.1]hept-2-ene-2,7-dicarboxylic acid 7-tert-butyl ester 2-methyl ester as a colorless oil (1.62 g, 10.4%). MS: 374 (M+H)⁺.

Step 2

A solution of 3-(1-phenyl-ethylamino)-7-aza-bicyclo[2.2.1]hept-2-ene-2,7-dicarboxylic acid 7-tert-butyl ester 2-methyl ester (0.3 g, 0.81 mmol) in acetic acid-acetonitrile (1:1, 20 mL) was treated with sodium triacetoxyborohydride (0.19 g, 0.89 mmol), stirred for 5 h at 0° C. and then neutralized with saturated aqueous sodium bicarbonate (5 mL). The organic layer was washed with brine (3×20 mL), then dried over MgSO₄, filtered and concentrated in vacuo. The residue was purified by Biotage Flash 40S chromatography, eluting with 2:1 ethyl acetate-hexanes, to provide 3-(1-phenyl-ethylamino)-7-aza-bicyclo[2.2.1]heptane-2,7-dicarboxylic acid 7-tert-butyl ester 2-methyl ester as a 3:1 mixture of diastereomers (0.28 g, 93%). MS: 375 (M+H)⁺.

Step 3

A mixture of 3-(1-phenyl-ethylamino)-7-aza-bicyclo [2.2.1]heptane-2,7-dicarboxylic acid 7-tert-butyl ester 2-methyl ester (0.28 g, 0.8 mmol) and 20% palladium hydroxide on carbon (0.2 g) in methanol (5 mL) was stirred under a hydrogen atmosphere (1 atm) for 19 h. The mixture was then filtered through a thin pad of celite and concentrated to provide 3-amino-7-aza-bicyclo[2.2.1]heptane-2,7-dicarboxylic acid 7-tert-butyl ester 2-methyl ester as a colorless oil (0.2 g, 71.4%). MS: 269 (M+H)⁺.

Step 4

To a mixture of 3-amino-7-aza-bicyclo[2.2.1]heptane-2,7-dicarboxylic acid 7-tert-butyl ester 2-methyl ester (0.2 g, 0.87 mmol] and 4-(2-methyl-quinolin-4-ylmethoxy)-benzenesulfonyl chloride hydrochloride (0.4 g, 1.0 mmol) in N,N-dimethylformamide (DMF, 10 mL) at 0° C. was added N,N-diisopropylethylamine (0.4 mL, 2.23 mmol). The solution was allowed to warm up to 25° C. over 19 h. The DMF was removed in vacuo and the solid was partitioned between ethyl acetate (100 mL) and water (30 mL). The aqueous layer was washed with ethyl acetate (2×50 mL). The organic layer was dried over MgSO₄, filtered and concentrated in vacuo. The residue was purified on a Biotage Flash 40S chromatography, eluting with 1:4 ethyl acetate-hexanes, to afford 3-[4-(2-methyl-quinolin-4-ylmethoxy)-benzene sulfonylamino]-7-aza-bicyclo [2.2.1]heptane-2,7-dicarboxylic acid 7-tert-butyl ester-2-methyl ester as a white solid (0.150 g, 23.5%). MS: 582 (M+H)⁺.

Step 5

A solution of 3-[4-(2-methyl-quinolin-4-ylmethoxy)-benzenesulfonylamino]-7-aza-bicyclo [2.2.1] heptane-2,7-dicarboxylic acid 7-tert-butyl ester 2-methyl ester (0.15 g, 2.58 mmol) and lithium hydroxide (0.062 g, 2.57 mmol) in THF:methanol:water (2.5: 1.5:1.5 mL) was stirred at 25° C. for 19 h. The solution was then concentrated in vacuo to give 3-[4-(2-methyl-quinolin-4-ylmethoxy)-benzenesulfonylamino]-7-aza-bicyclo[2.2.1] heptane-2,7-dicarboxylic acid 7-tert-butyl ester as a crude solid (0.150 g, 100%). MS: 568 (M+H)⁺.

Step 6

According to the procedure of Example 24, Step 3, 0.15 g (0.26 mmol) of 3-[4-(2-methyl-quinolin-4-ylmethoxy)-benzenesulfonylamino]-7-aza-bicyclo[2.2.1]heptane-2,7-dicarboxylic acid 7-tert-butyl ester and hydroxylamine gave tert-butyl 2-[(hydroxyamino)carbonyl]-3-[({4-[(2-methylquinolin-4-yl)methoxy]phenyl}sulfonyl)amino]-7-azabicyclo[2.2.1]heptane-7-carboxylate as an amorphous off yellow solid (0.0162 g, 14.7%) after Biotage Flash 40S chromatography, eluting with 5% methanol in ethyl acetate. MS: 583 (M+H)⁺

Example 38

3-[4-(2-Methyl-quinolin-4-ylmethoxy)-benzenesulfonylamino]-7-aza-bicyclo[2.2.1]heptane-2-carboxylic acid hydroxyamide

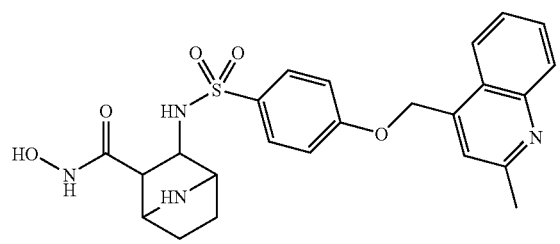

According to the procedure of Example 24, Step 3, 0.05 g (0.088 mmol) of 3-[4-(2-methyl-quinolin-4-ylmethoxy)-benzenesulfonylamino]-7-aza-bicyclo[2.2.1]heptane-2,7-dicarboxylic acid 7-tert-butyl ester (Example 37, Step 5) and hydroxylamine, followed by treatment with TFA:CH₂Cl₂ (1:1, 0.2 mL) for 15 min, gave 3-[4-(2-methyl-quinolin-4-ylmethoxy)-benzenesulfonylamino]-7-aza-bicyclo[2.2.1] heptane-2-carboxylic acid hydroxyamide as a hygroscopic solid (0.0189 g, 37.2%). MS: 483 (M+H)⁺

Example 39

(1R,2S,3R,4S)-N-hydroxy-3-(methyl{[4-(2-naphthylmethoxy)phenyl]sulfonyl}amino)bicyclo[2.2.1]heptane-2-carboxamide

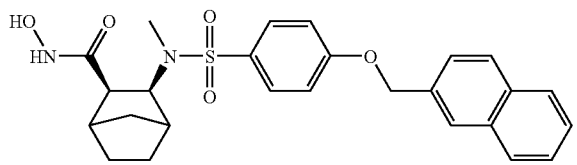

Step 1

To a solution of 3-exo-aminobicyclo[2.2.1]hept-5-ene-2-exo-carboxylic acid (4.60 g, 0.03 mol) and 4-benzyloxy-benzenesulfonyl chloride (8.49 g, 0.03 mol) in water-dioxane (30 mL–30 mL) was added triethylamine (8.38 mL, 0.06 mol) at room temperature. The mixture was stirred for 12 h. The solution was concentrated and the residue was dissolved in water (30 mL). The aqueous solution was extracted with ether (50 mL) and the aqueous layer was acidified with 1 N HCl. The white precipitate was collected and dried to give 3-(4-benzyloxy-benzenesulfonylamino)-bicyclo[2.2.1]hept-5-ene-2-carboxylic acid (98% yield). Mp=201-203° C. (white solid).

Step 2

To a solution of 3-(4-benzyloxy-benzenesulfonylamino)-bicyclo[2.2.1]hept-5-ene-2-carboxylic acid (2.5 g, 6.26 mmol) in DMF (40 mL) were added potassium carbonate (4.33 g, 31.3 mmol) and iodomethane (1.56 mL, 25.0 mmol) at room temperature. The mixture was stirred for 12 h, and then diluted with ethyl acetate (150 mL), and washed with water (5×100 mL) and brine (100 mL). The organic solution was dried over Na₂SO₄, and concentrated to give 3-[(4-benzyloxy-benzenesulfonyl)-methyl-amino]-bicyclo[2.2.1]hept-5-ene-2-carboxylic acid methyl ester (96% yield). Mp=103-104° C. (white solid).

Step 3

To a solution of 3-[(4-benzyloxy-benzenesulfonyl)-methyl-amino]-bicyclo[2.2.1]hept-5-ene-2-carboxylic acid methyl ester (1.5 g, 3.51 mmol) in ethanol-CH$_2$Cl$_2$ (45 mL-5 mL) were added 10% Pd—C (1.12 g, 1.05 mmol) and 1,4-cycloexadiene (3.32 mL, 35.1 mmol) at room temperature. The mixture was stirred for 12 h and then filtered through celite. The organic solution was concentrated and the residue was purified by flash chromatography eluting with 40% ethyl acetate/hexanes to give 3-[(4-hydroxy-benzenesulfonyl)-methyl-amino]-bicyclo[2.2.1]heptane-2-carboxylic acid methyl ester (97% yield). Mp=163-164° C. (white solid).

Step 4

To a solution of 3-[(4-hydroxy-benzenesulfonyl)-methyl-amino]-bicyclo[2.2.1]heptane-2-carboxylic acid methyl ester (130 mg, 0.383 mmol) in DMF (1 mL) were added K$_2$CO$_3$ (159 mg, 1.15 mmol) and (2-bromomethyl)naphthalene (102 mg, 0.46 mmol) at room temperature. The mixture was stirred for 10 h. The mixture was extracted with ethyl acetate (3×3 mL) and the organic layer was concentrated. The residue was purified by RP-HPLC to give the 3-{methyl-[4-(naphthalen-2-ylmethoxy)-benzenesulfonyl]-amino}-bicyclo[2.2.1]heptane-2-carboxylic acid methyl ester. The methyl ester was dissolved in MeOH-THF (1 mL-1 mL) and 1N NaOH (1.15 mL, 1.15 mmol) was added to the mixture. After stirring for 10 h, the mixture was acidified with HCl. The resulting mixture was extracted with ethyl acetate (3×3 mL) and the organic layer was concentrated. The residue was purified by RP-HPLC to give 3-{methyl-[4-(naphthalen-2-ylmethoxy)-benzenesulfonyl]-amino}-bicyclo[2.2.1]heptane-2-carboxylic acid (70% yield for two steps).

Step 5:

To a solution of 3-{methyl-[4-(naphthalen-2-ylmethoxy)-benzenesulfonyl]-amino}-bicyclo[2.2.1]heptane-2-carboxylic acid (125 mg, 0.268 mmol) in DMF (1 mL) were added 1-(3-dimethylaminopropyl)-3-ethylcarbodimide hydrochloride (103 mg, 0.536 mmol), 1-hydroxybenzotriazole (72.5 mg, 0.536 mmol) and hydroxylamine (50% in water, 82 µL, 1.34 mmol) at room temperature. The mixture was stirred for 20 h, diluted with ethyl acetate (5 mL), and washed with water (3×3 mL) and brine (3 mL). The organic layer was concentrated and the residue was purified by RP-HPLC to give (1R,2S,3R,4S)-N-hydroxy-3-(methyl{[4-(2-naphthylmethoxy)phenyl]sulfonyl}amino)bicyclo[2.2.1]heptane-2-carboxamide (50% yield). MS (ESI) [M+H] 481.2

Example 40

(1R,2S,3R,4S)-3-[{[4-(2,1,3-benzoxadiazol-5-ylmethoxy)phenyl]sulfonyl}(methyl)amino]-N-hydroxybicyclo[2.2.1]heptane-2-carboxamide

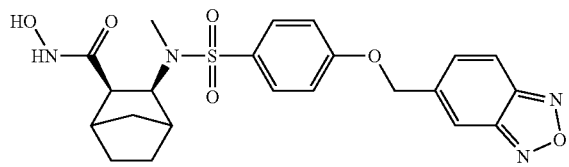

(1R,2S,3R,4S)-3-[{[4-(2,1,3-Benzoxadiazol-5-ylmethoxy)phenyl]sulfonyl}(methyl)amino]-N-hydroxybicyclo[2.2.1]heptane-2-carboxamide was prepared by using same procedure as described for the synthesis of Example 39, except 5-bromomethyl-benzo[1,2,5]oxadiazole was used in Step 4 instead of (2-bromomethyl)naphthalene. MS (ESI) [M+H] 473.1

Example 41

(1R,2S,3R,4S)-N-hydroxy-3-(methyl{[4-(quinolin-2-ylmethoxy)phenyl]sulfonyl}amino)bicyclo[2.2.1]heptane-2-carboxamide

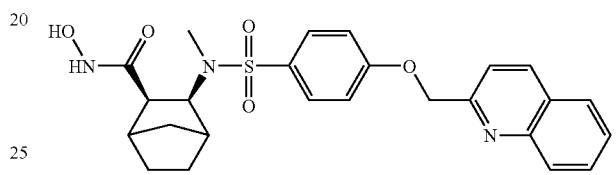

Step 1

To a solution of 130 mg (0.383 mmol) of 3-[(4-hydroxy-benzenesulfonyl)-methyl-amino]-bicyclo[2.2.1]heptane-2-carboxylic acid methyl ester (Example 39, Step 3) in DMF (1 mL) were added K$_2$CO$_3$ (159 mg, 1.15 mmol) and (2-chloromethyl)quinoline hydrochloride (98.5 mg, 0.46 mmol) at room temperature. The mixture was stirred for 10 h. The mixture was extracted with ethyl acetate (3×3 mL) and the organic layer was concentrated. The residue was purified by RP-HPLC to give the 3-{methyl-[4-(quinolin-2-ylmethoxy)-benzenesulfonyl]-amino}-bicyclo[2.2.1]heptane-2-carboxylic acid methyl ester. The methyl ester was dissolved in MeOH-THF (1 mL-1 mL) and 1N NaOH (1.15 mL, 1.15 mmol) was added to the mixture. After stirring for 10 h, the mixture was acidified with HCl. The resulting mixture was extracted with ethyl acetate (3×3 mL) and the organic layer was concentrated. The residue was purified by RP-HPLC to give the 3-{methyl-[4-(quinolin-2-ylmethoxy)-benzenesulfonyl]-amino}-bicyclo[2.2.1]heptane-2-carboxylic acid (70% yield for two steps).

Step 2

To a solution of 3-{methyl-[4-(quinolin-2-ylmethoxy)-benzenesulfonyl]-amino}-bicyclo[2.2.1]heptane-2-carboxylic acid (125 mg, 0.268 mmol) in DMF (1 mL) were added EDCI (103 mg, 0.536 mmol), HOBT (72.5 mg, 0.536 mmol) and hydroxylamine (50% in water, 82 µL, 1.34 mmol) at room temperature. The mixture was stirred for 20 h, diluted with ethyl acetate (5 mL), and washed with water (3×3 mL) and brine (3 mL). The organic layer was concentrated and the residue was purified by RP-HPLC to give (1R,2S,3R,4S)-N-hydroxy-3-(methyl{[4-(quinolin-2-ylmethoxy)phenyl]sulfonyl}amino)bicyclo[2.2.1]heptane-2-carboxamide (50% yield). MS (ESI) [M+H] 482.2

Example 42

(1R,2S,3R,4S)-3-[{[4-(1H-benzimidazol-2-yl-methoxy)phenyl]sulfonyl}(methyl)amino]-N-hydroxybicyclo[2.2.1]heptane-2-carboxamide

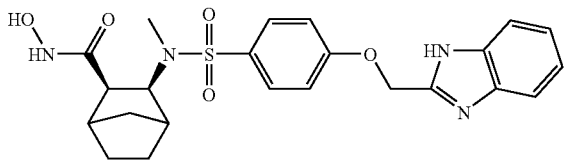

(1R,2S,3R,4S)-3-[{[4-(1H-Benzimidazol-2-ylmethoxy)phenyl]sulfonyl}(methyl)amino]-N-hydroxybicyclo[2.2.1]heptane-2-carboxamide was prepared following the same procedure as described in Example 41 except 2-chloromethyl-1H-1,3-benzimidazole was used instead of (2-chloromethyl)quinoline hydrochloride in Step 4. MS (ESI) [M+H] 471.2

Example 43

(1R,2S,3R,4S)-3-[{[4-(1H-1,2,3-benzotriazol-1-yl-methoxy)phenyl]sulfonyl}(methyl)amino]-N-hydroxybicyclo[2.2.1]heptane-2-carboxamide

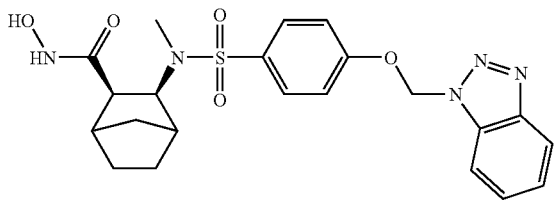

(1R,2S,3R,4S)-3-[{[4-(1H-1,2,3-Benzotriazol-1-yl-methoxy)phenyl]sulfonyl}(methyl)amino]-N-hydroxybicyclo[2.2.1]heptane-2-carboxamide was prepared following the same procedure as described in Example 41 except 1-chloromethyl-1H-benzotriazole was used instead of (2-chloromethyl)quinoline hydrochloride in Step 4. MS (ESI) [M+H] 472.2

Example 44

(3R,4R)-N-hydroxy-3-methyl-4-[({4-[(2-methylquinolin-4-yl)methoxy]phenyl}sulfonyl)amino]tetrahydro-2H-pyran-3-carboxamide

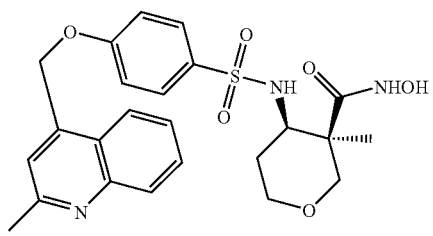

Step 1

Lithium hexamethyldisilazide (1.0 M in THF, 263 mL, 1.05 eq) was added dropwise to a −78° C. solution of tetrahydro-4H-pyran-one (25 g, 250 mmol) in THF (800 mL). The resulting solution was stirred for 1.5 h. To this mixture was added methyl cyanoformate (24 mL, 1.2 eq) dropwise at −78° C. Ten minutes after completion of the addition, the reaction was quenched with semi-saturated $NH_4Cl$ (1 L) and extracted with ether (1 L). The organic layer was washed with brine, dried over $MgSO_4$, and concentrated. Silica gel column chromatography (20-40% ethyl acetate/hexane) yielded an oil containing methyl 4-oxo-tetrahydro-2H-pyran-3-carboxylate and methyl 4-hydroxy-5,6-dihydro-2H-pyran-3-carboxylate (15 g).

Step 2

Methyl 4-oxo-tetrahydro-2H-pyran-3-carboxylate and methyl 4-hydroxy-5,6-dihydro-2H-pyran-3-carboxylate (13.5 g, 85.5 mmol) were dissolved in DMF (70 mL). Sodium hydride (60%, 3.6 g, 1.05 eq) was added at 0° C. After 10 min, iodomethane (6.7 mL, 1.25 eq) was added. The reaction was stirred overnight, diluted with ethyl acetate (200 mL), and washed with water (5×100 mL). The aqueous layer was re-extracted with ethyl acetate. The combined organic layers were washed with brine, dried over $MgSO_4$, and concentrated. The residue was purified by chromatography on silica gel eluting with 20% ethyl acetate/hexane to yield 8.2 g (61%) of methyl 3-methyl-4-oxo-tetrahydro-2H-pyran-3-carboxylate.

Step 3

Methyl 3-methyl-4-oxo-tetrahydro-2H-pyran-3-carboxylate (2.33 g, 13.53 mmol) was dissolved in toluene (150 mL) and treated with R-(+)-α-methylbenzylamine (3.96 mL, 2.3 eq) and ytterbium (III) trifluoromethanesulfonate (252 mg, 0.03 eq). The mixture was heated to reflux under Dean-Stark conditions overnight, and then concentrated to provide crude methyl 3-methyl-4-((R)-1-phenylethylimino)-tetrahydro-2H-pyran-3-carboxylate that was used in the next step without further purification.

Step 4

Methyl 3-methyl-4-((R)-1-phenylethylimino)-tetrahydro-2H-pyran-3-carboxylate (crude, 13.53 mmol) in acetonitrile-acetic acid (1:1, 80 mL) was treated with $NaBH(OAc)_3$ and stirred for 2.5 h at 0° C. Following concentration in vacuo, the residue was dissolved in ethyl acetate (200 mL), washed with saturated $NaHCO_3$ until the aqueous phase was basic, dried over $MgSO_4$, and purified by chromatography with 20% ethyl acetate/hexane to yield 1.37 g (37% in 2 steps) of (4R)-methyl 3-methyl-4-((R)-1-phenylethylamino)-tetrahydro-2H-pyran-3-carboxylate. MS: $(M+H)^+$=278.1.

Step 5

(4R)-Methyl 3-methyl-4-((R)-1-phenylethylamino)-tetrahydro-2H-pyran-3-carboxylate (1.37 g, 4.94 mmol) in methanol (70 mL) was treated with 10% palladium hydroxide on carbon (0.42 g, 3.5% mol) and aqueous 1N HCl (7 mL, 1.4 eq) and stirred under a hydrogen balloon for 72 h. The catalyst was removed by filtration. Removal of solvent provided crude methyl 4-amino-3-methyl-tetrahydro-2H-pyran-3-carboxylate hydrochloride that was used in the next step without further purification. MS: $(M+H)^+$=174.1.

Step 6

Crude methyl 4-amino-3-methyl-tetrahydro-2H-pyran-3-carboxylate hydrochloride (8.65 mmol), 4-benzyloxy-benzenesulfonyl chloride (1.2 eq), $CH_2Cl_2$ (175 mL) and saturated $NaHCO_3$ (90 mL) were combined and stirred at room temperature overnight. The organic phase was then washed with water (100 mL) and brine (100 mL), dried over $MgSO_4$, and concentrated. The residue was purified by chromatography with 20-35% ethyl acetate/hexane to provide two diastereomers, (3R,4R)-methyl 4-(4-(benzyloxy)phenylsulfonamido)-3-methyl-tetrahydro-2H-pyran-3-carboxylate and (3S,4R)-methyl 4-(4-(benzyloxy)phenylsulfonamido)-3-methyl-tetrahydro-2H-pyran-3-carboxylate. MS: $(M+H)^+$ =420.0.

Step 7

(3R,4R)-Methyl 4-(4-(benzyloxy)phenylsulfonamido)-3-methyl-tetrahydro-2H-pyran-3-carboxylate (856 mg, 2.04 mmol) was stirred with 15% NaOH (5 mL) in THF (5 mL) and MeOH (5 mL) at 45° C. overnight. The mixture was then cooled to 0° C. and acidified with 2N HCl to pH ~3. After extraction with ethyl acetate the organics were washed with brine, dried over $MgSO_4$, and concentrated. The residue was triturated with ether to yield 726 mg (88%) of (3R,4R)-4-(4-(benzyloxy)phenylsulfonamido)-3-methyl-tetrahydro-2H-pyran-3-carboxylic acid as a white solid. MS: $(M+Na)^+$ =428.0; $(M-H)^-$=404.1.

Step 8

(3R,4R)-4-(4-(Benzyloxy)phenylsulfonamido)-3-methyl-tetrahydro-2H-pyran-3-carboxylic acid (715 mg, 1.76 mmol) was dissolved in DMF (8 mL), and BOP reagent (1.01 g, 2.29 mmol, 1.3 eq), N,N-diisopropylethylamine (1.2 mL, 7.04 mmol, 4.0 eq) and O-(tert-butyl)hydroxylamine hydrochloride (332 mg, 2.64 mmol, 1.5 eq) were sequentially added. The reaction was stirred at room temperature overnight and then diluted with ethyl acetate (200 mL), and washed with water (3×50 mL). The aqueous layer was re-extracted with ethyl acetate. The combined organic layers were washed with brine, dried over $MgSO_4$, and concentrated affording (3R,4R)-4-(4-(benzyloxy)phenylsulfonamido)-N-tert-butoxy-3-methyl-tetrahydro-2H-pyran-3-carboxamide as white fluffy powder that was used in the next step without purification. MS: $(M+Na)^+$=499.0; $(M-H)^-$=475.2.

Step 9

(3R,4R)-4-(4-(Benzyloxy)phenylsulfonamido)-N-tert-butoxy-3-methyl-tetrahydro-2H-pyran-3-carboxamide was dissolved in ethyl acetate (25 mL), 10% palladium on carbon (90 mg) was added, and the resulting reaction mixture was stirred under a hydrogen balloon overnight. The reaction mixture was then filtered and concentrated to provide (3R,4R)-N-tert-butoxy-4-(4-hydroxyphenylsulfonamido)-3-methyl-tetrahydro-2H-pyran-3-carboxamide as a white solid that was used in the next step without purification. MS: $(M+Na)^+$=409.0; $(M-H)^-$=385.2.

Step 10

The crude (3R,4R)-N-tert-butoxy-4-(4-hydroxyphenylsulfonamido)-3-methyl-tetrahydro-2H-pyran-3-carboxamide (1.76 mmol) from Step 9 was dissolved in DMF (20 mL) and cesium carbonate (2.9 g, 8.80 mmol, 5.0 eq) and 4-chloromethyl-2-methylquinoline (602 mg, 2.64 mmol, 1.5 eq) were added. The mixture was stirred at room temperature overnight and then diluted with ethyl acetate (200 mL) and washed with water (100 mL×3). The aqueous layer was re-extracted with ethyl acetate. The combined organic layers were washed with brine, dried over $MgSO_4$ and concentrated. The residue was purified by chromatography on silica eluting with 75% ethyl acetate/hexane to yield 0.53 g (56% for three steps) of (3R,4R)-N-tert-butoxy-3-methyl-4-(4-((2-methylquinolin-4-yl)methoxy)phenylsulfonamido)-tetrahydro-2H-pyran-3-carboxamide as white solid. MS: $(M+H)^+$=542.0

Step 11

The (3R,4R)-N-tert-butoxy-3-methyl-4-(4-((2-methylquinolin-4-yl)methoxy)phenylsulfonamido)-tetrahydro-2H-pyran-3-carboxamide (0.52 g, 0.96 mmol) from Step 10 was stirred in neat trifluoroacetic acid (3 mL) at 40° C. for 3.5 h. The reaction mixture was then concentrated in vacuo and chased with methanol. The residue was then stirred in ethyl acetate (100 mL) and saturated $NaHCO_3$ (50 mL) for 15 min. The organic layer was washed with water (50 mL), then with brine (50 mL), dried over $MgSO_4$, and concentrated. The residue was purified by chromatography on silica eluting with 5-8% $MeOH/CH_2Cl_2$ to yield 140 mg (30%) of (3R,4R)-N-hydroxy-3-methyl-4-(4-((2-methylquinolin-4-yl)methoxy)phenylsulfonamido)-tetrahydro-2H-pyran-3-carboxamide as an off-white solid. In addition, 35% of the starting material was recovered. HRMS: calcd for $C_{24}H_{27}N_3O_6S+H^+$, 486.16933; found (ESI-FT-MS, $[M+H]^{+1}$), 486.1695

Example 45

(3S,4R)-N-hydroxy-3-methyl-4-[({4-[(2-methylquinolin-4-yl)methoxy]phenyl}sulfonyl)amino]tetrahydro-2H-pyran-3-carboxamide

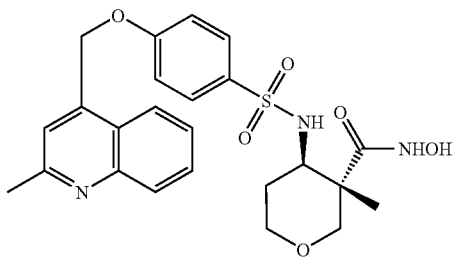

(3S,4R)-Methyl 4-(4-(benzyloxy)phenylsulfonamido)-3-methyl-tetrahydro-2H-pyran-3-carboxylate from Example 44, Step 6, was converted into(3S,4R)-N-hydroxy-3-methyl-4-[({4-[(2-methylquinolin-4-yl)methoxy]phenyl}sulfonyl)amino]tetrahydro-2H-pyran-3-carboxamide according to the procedures of Steps 7 to 11 in Example 44. The product was purified by preparative HPLC (10-30% acetonitrile with folic acid in 10 min). An off-white solid was obtained (31%). HRMS: calcd for $C_{24}H_{27}N_3O_6S+H^+$, 486.16933; found (ESI-FTMS, $[M+H]^{1+}$), 486.1704

Example 46

4-({4-[({(3R,4R)-1-Formyl-3-hydroxy-3-[(hydroxyamino)carbonyl]piperidin-4-yl}amino)sulfonyl]phenoxy}methyl)-2-methylquinolinium trifluoroacetic acid salt

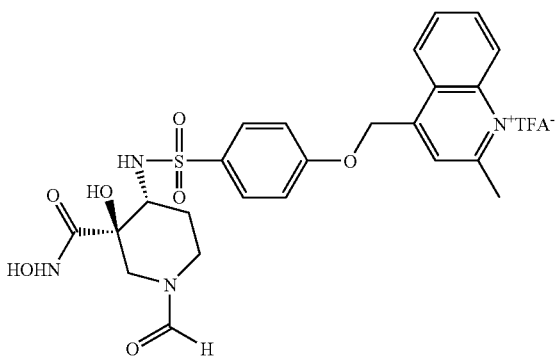

Step 1

Arecoline hydrobromide (25 g, 106 mmol) was neutralized with sodium carbonate (12.8 g, 120 mmol, 1.1 eq) in water (200 mL) for 30 min. The neutralized product was dissolved in toluene (50 mL) and added dropwise to a solution of triphosgene (16.3 g, 54.9 mmol, 0.52 eq) in toluene (100 mL) at 0° C. The resulting mixture was heated at 55-60° C. overnight. The reaction mixture was then concentrated in vacuo and the residue was dissolved in water (300 mL) and heated at 80° C. for 3 h. The water was evaporated and chased with toluene 3 times. The crude methyl 1,2,5,6-tetrahydropyridine-3-carboxylate hydrochloride, obtained as a thick brown oil, was used as is in the next reaction.

Step 2

A mixture of methyl 1,2,5,6-tetrahydropyridine-3-carboxylate hydrochloride (crude, 150 mmol), 5-chlorodibenzosuberane (41 g, 180 mmol, 1.2 eq), sodium iodide (2.2 g, 15 mmol, 0.1 eq) and triethylamine (63 mL, 450 mmol, 3.0 eq) in dioxane (300 mL) was stirred at 90° C. overnight. The reaction mixture was concentrated in vacuo and the residue was partitioned between ethyl acetate and water. The organic phase was washed with brine, dried over $MgSO_4$, and concentrated. The crude product was passed through a silica gel plug, eluting with $CH_2Cl_2$. After concentration, the resulting solid was triturated with ether to yield 27 g (55%) of methyl 1-(10,11-dihydro5H-dibenzo[a,d][7]annulen-5-yl)-1,2,5,6-tetrahydropyridine-3-carboxylate.

Step 3 n-Butyllithium (9.6 mL, 24 mmol, 1.6 eq) was added dropwise to a solution of R-(+)-N-benzyl-α-methylbenzylamine (6.2 mL, 30 mmol, 2.0 eq) in THF (200 mL) at −78° C. After 50 min, methyl 1-(10,11-dihydro-5H-dibenzo[a,d][7]annulen-5-yl)-1,2,5,6-tetrahydropyridine -3-carboxylate (5 g, 15 mmol) in THF (30 mL) was added dropwise. After 2.5 h, (1R)-(−)-(10-camphorsulfonyl)oxaziridine (6.8 g, 30 mmol, 2.0 eq) in THF (50 mL) was added and the reaction was stirred for 15 min at −78° C. before warming to room temperature. After 12 h, saturated ammonium chloride (~2 mL) was added and the resulting mixture was then concentrated in vacuo. The residue was extracted with ethyl acetate and the combined organic layers were washed sequentially with 10% citric acid, saturated sodium bicarbonate and brine, dried over $MgSO_4$, and concentrated. The residue was purified by chromatography on silica gel eluting with 10% ethyl acetate/hexane to yield 3.89 g (46%) of methyl (3R,4R)-4-{benzyl[(1S)-1-phenylethyl]amino}-1-(10,11-dihydro-5H-dibenzo[a,d][7]annulen-5-yl)-3-hydroxypiperidine-3-carboxylate as white fluffy powder. MS: $(M+H)^+=561.2$.

Step 4

To a solution of methyl (3R,4R)-4-{benzyl[(1S)-1-phenylethyl]amino}-1-(10,11-dihydro-5H-dibenzo[a,d][7]annulen-5-yl)-3-hydroxypiperidine-3-carboxylate (4.14 g, 6.94 mmol) in $CH_2Cl_2$ (10 mL) was added triethylsilane (1.6 mL, 10.2 mmol, 1.3 eq), followed by trifluoroacetic acid (10 mL). The reaction was stirred at room temperature for 30 min. The reaction was then concentrated in vacuo and residual trifluoroacetic acid was chased 3 times with methanol to yield an off-white solid. The solid was combined with THF (40 mL), triethylamine (5.5 mL, 39.15 mmol, 5.0 eq) and di-tert-butyldicarbonate (1.88 g, 8.61 mmol, 1.1 eq) and stirred at rt overnight. The solvent was concentrated in vacuo and the residue was extracted with ethyl acetate. The organic layer was washed with water and brine, dried over $MgSO_4$, and concentrated. The crude product was purified by chromatography on silica gel eluting with 20% ethyl acetate/hexane to yield 2.89 g (89%) of 1-tert-butyl 3-methyl (3R,4R)-4-{benzyl[(1S)-1-phenylethyl]amino}-3-hydroxypiperidine-1,3-dicarboxylate as white fluffy powder. MS: $(M+H)^+=469.1$.

Step 5

To a solution of 1-tert-butyl 3-methyl (3R,4R)-4-{benzyl[(1S)-1-phenylethyl]amino}-3-hydroxypiperidine-1,3-dicarboxylate in methanol was added 10% Pd/C (50% weight of starting material), followed by ammonium formate (10 eq). The reaction was stirred for 1.5 h, filtered through celite, and concentrated in vacuo. The residue was extracted with ethyl acetate. The organic phase was washed with brine, dried over $MgSO_4$, and concentrated. The residue, 1-tert-butyl 3-methyl (3R,4R)-4-amino-3-hydroxypiperidine-1,3-dicarboxylate, was used as is in the next step.

Step 6

A suspension of 1-tert-butyl 3-methyl (3R,4R)-4-amino-3-hydroxypiperidine-1,3-dicarboxylate (1.63 g, 5.96 mmol), 4-((2-methylquinolin-4-yl)methoxy)benzene-1-sulfonyl chloride hydrochloride (4.6 g, 11.92 mmol, 2.0 eq), $CH_2Cl_2$ (100 mL) and saturated $NaHCO_3$ (50 mL) was stirred at room temperature overnight, and then diluted with $CH_2Cl_2$. The organic phase was washed with water, then brine, dried over $MgSO_4$, and concentrated. The residue was purified by chromatography on silica gel eluting with 50-70% ethyl acetate/hexane to yield 1.65 g (47%) of 1-tert-butyl 3-methyl (3R,4R)-3-hydroxy-4-[({4-[(2-methylquinolin-4-yl)methoxy]phenyl}sulfonyl)amino]piperidine-1,3-dicarboxylate as white solid. MS: $(M+H)^+=586.1$.

Step 7

A mixture of 1-tert-butyl 3-methyl (3R,4R)-3-hydroxy-4-[({4-[(2-methylquinolin-4-yl)methoxy]phenyl}sulfonyl)amino]piperidine-1,3-dicarboxylate (1.59 g, 2.72 mmol), methanol (10 mL), THF (10 mL) and 1N sodium hydroxide (10.9 mL, 4 eq) was stirred overnight. Triethylamine hydrochloride (2.25 g, 16.32 mmol, 6 eq) was added and the resulting mixture was stirred for awhile and then concentrated in vacuo. The residue was dried by azeotropic evaporation with toluene and then dried under high vacuum for 5 h. This crude carboxylic acid was dissolved in DMF (30 mL) and diisopropylethylamine (1.9 mL, 10.88 mmol, 4.0 eq), BOP reagent (1.56 g, 3.54 mmol, 1.3 eq) and O-tert-butylhydroxylamine hydrochloride (512 mg, 4.08 mmol, 1.5 eq) were added. The reaction was stirred overnight, and then diluted with ethyl acetate and water. The organic phase was washed with water three times. The aqueous layer was re-extracted with ethyl acetate. The combined organic layers were washed with brine, dried over $MgSO_4$, and concentrated. The residue was purified by chromatography with 65-70% ethyl acetate/hexane to yield 740 mg (42% in two steps) of tert-butyl (3R,4R)-3-[(tert-butoxyamino)carbonyl]-3-hydroxy-4-[({4-[(2-methylquinolin-4-yl)methoxy]phenyl}sulfonyl)amino]piperidine-1-carboxylate as white solid. MS: $(M+H)^+=643.1$.

Step 8

To a solution of tert-butyl (3R,4R)-3-[(tert-butoxyamino)carbonyl]-3-hydroxy-4-[({4-[(2-methylquinolin-4-yl)methoxy]phenyl}sulfonyl)amino]piperidine-1-carboxylate (740 mg, 1.15 mmol) in $CH_2Cl_2$ (10 mL) was added trifluoroacetic acid (2.5 mL). The reaction was stirred at room temperature for 1.5 h. The solvent was concentrated in vacuo and methanol was used to chase residual trifluoroacetic acid. The residue was precipitated from ether as a white solid to yield 856 mg (97%) of (3R,4R)-N-tert-butoxy-3-hydroxy-4-(4-((2-methylquinolin-4-yl) methoxy)phenylsulfonamido)piperidine-3-carboxamide as the trifluoroacetic acid salt. MS: $(M+H)^+=543.1$.

Step 9

(3R,4R)-N-tert-Butoxy-3-hydroxy-4-(4-((2-methylquinolin-4-yl)methoxy)phenylsulfonamido)piperidine-3-carboxamide trifluoroacetic acid salt (250 mg, 0.32 mmol) was dissolved in methanol (1 mL) and diisopropylethylamine (0.23 mL, 1.3 mmol, 4 eq) was added, followed by ethyl formate (5 mL, excess). The reaction was heated at 46° C. for 5 h, and then concentrated in vacuo. The residue was triturated with ether to yield 112 mg (62%) of (3R,4R)-N-tert-butoxy-1-formyl-3-hydroxy-4-(4-((2-methylquinolin-4-yl)methoxy)phenylsulfonamido)piperidine-3-carboxamide as white waxy solid. MS: (M+H)$^+$=571.1.

Step 10

(3R,4R)-N-tert-Butoxy-1-formyl-3-hydroxy-4-(4-((2-methylquinolin-4-yl)methoxy)phenylsulfonamido)piperidine-3-carboxamide (112 mg, 0.2 mmol) was stirred in neat trifluoroacetic acid (5 mL) at 45° C. for 5 days. After removal of the trifluoroacetic acid, the residue was purified using preparative HPLC (5-20% of acetonitrile with folic acid in 10 min) to yield 29 mg (23%) of 4-({4-[({(3R,4R)-1-formyl-3-hydroxy-3-[(hydroxyamino)carbonyl]piperidin-4-yl}amino) sulfonyl]phenoxy}methyl)-2-methylquinolinium trifluoroacetic acid salt as white, fluffy powder. HRMS: calcd for $C_{24}H_{27}N_4O_7S$, 515.16005; found (ESI-FTMS, M$^+$), 515.1604

Example 47

(3S,4R)-1-acetyl-N-hydroxy-3-methyl-4-[({4-[(2-methylquinolin-4-yl)methoxy]phenyl}sulfonyl)amino]piperidine-3-carboxamide

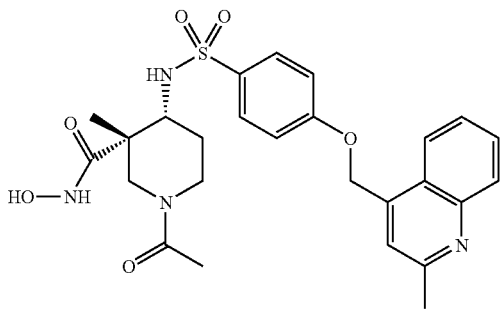

Step 1

To 7.338 g (41.31 mol) of guvacoline hydrochloride (*Arzneim. Forsch.* 1989, 39(5), 539. ) in dioxane (100 ml) was added 5-chloro-dibenzosuberane (14.933 g, 65.39 mmol), NaI (catalytic, ~1 g), and triethylamine (17 mL, 122.0 mmol) to give a brown heterogeneous slurry that was heated at 90° C. overnight. The solvent was then concentrated and the resultant sludge was taken up in ethyl acetate and sequentially washed with $Na_2HPO_4$ buffer (pH 4), $Na_2CO_3$ (saturated aqueous), and brine. The organics were then dried over $Na_2SO_4$ and concentrated, resulting in a brown solid which was purified by chromatography on silica gel eluting with 1-5% ethyl acetate/hexanes to give 1-(10,11-dihydro-5H-dibenzo[a,d]cyclohepten-5-yl)-1,2,5,6-tetrahydro-pyridine-3-carboxylic acid methyl ester as a white solid (9.584 g, 28.74 mmol, 67%). $^1$H NMR (400 MHz, CHLOROFORM-D) δ ppm 2.22 (dt, J=9.28, 2.68 Hz, 2H) 2.41 (t, J=5.56 Hz, 2H) 2.73-2.83 (m, 2H) 2.99-3.05 (m, 2H) 3.65 (s, 3 H) 3.90-4.00 (m, 2H) 4.11 (s, 1H) 6.94-6.99 (m, J=3.98, 3.98, 1.89, 1.77 Hz, 1 H) 7.05-7.11 (m, 4H) 7.13-7.21 (m, 4H).

Step 2

In a dry flask R-(+)-N-benzyl-N-a-methylbenzylamine (9.148 g, 43.29 mmol) and THF (40 mL) were cooled to −78° C. n-Butyllithium (22 ml, 2.2 M, 48.4 mmol) was added dropwise, resulting in a fuchsia colored solution which was stirred for 1 h. The 1-(10,11 -dihydro-5H-dibenzo[a,d]cyclohepten-5-yl)-1,2,5,6-tetrahydro-pyridine-3-carboxylic acid methyl ester (9.584 g, 28.74 mmol) in THF (30 mL) was added dropwise and the resulting orange solution was stirred at −78° C. for 3 h. Iodomethane (3 mL, 48.2 mmol) was added slowly and the reaction was allowed to warm to room temperature overnight. The reaction was quenched with $NH_4Cl$ (saturated aqueous) and subsequent solvent removal gave a heterogeneous slurry that was taken up in ethyl acetate, washed with $Na_2CO_3$ (saturated aqueous), brine, then dried over $Na_2SO_4$, and concentrated to give an orange oil. Column chromatography on silica gel eluting with 1-3% ethyl acetate/hexanes gave (3S,4R)-4-[benzyl-((R)-1-phenyl-ethyl)-amino]-1-(10,11-dihydro-5H-dibenzo[a,d]cyclohepten-5-yl)-3-methyl-piperidine-3-carboxylic acid methyl ester as a mixture of products that was carried on with out further purification. $^1$H NMR (400 MHz, CHLOROFORM-D) δ ppm 1.74-1.82 (m, 11 H) 2.90-2.99 (m, 3H) 3.41-3.49 (m, 5H) 3.82-3.88 (m, J=4.17, 2.27, 2.27, 2.27, 2.15 Hz, 2H) 4.57-4.66 (m, J=7.45, 3.73, 3.73, 3.54 Hz, 2H) 5.22-5.32 (m, 6H) 6.44 (dd, J=8.21, 5.18 Hz, 1H) 7.13-7.21 (m, 1H) 7.22-7.28 (m, 2H) 7.55 (d, J=1.52 Hz, 1H) 7.63 (dd, J=8.72, 1.89 Hz, 1H) 8.09 (d, J=8.59 Hz, 1H).

Step 3

Crude (3S,4R)-4-[benzyl-((R)-1-phenyl-ethyl)-amino]-1-(10,11-dihydro-5H-dibenzo[a,d]cyclohepten-5-yl)-3-methyl-piperidine-3-carboxylic acid methyl ester and triethylsilane (6 mL, 37.6 mmol) were taken up in 50 mL trifluoroacetic acid /$CH_2Cl_2$ (1:1, v/v), with vigorous gas evolution being observed. This homogeneous solution was stirred for 0.5 h at room temperature and then concentrated. The resultant oil was triturated with ether to remove excess trifluoroacetic acid. The orange oil was combined with THF (50 mL), $Et_3N$ (12 mL, 86 mmol), and di-tert-butyl-dicarbonate (7.652 g, 35.06 mmol) and stirred at room temperature overnight. Concentration of the solvent resulted in a brown oil that was purified by chromatography on silica gel eluting with 5-15% ethyl acetate/hexanes to give (3S,4R)-1-tert-butyl 3-methyl 4-(benzyl((R)-1-phenylethyl)amino)-3-methylpiperidine-1,3-dicarboxylate as a colorless solid (4.777 g, 10.24 mol). $^1$H NMR (400 MHz, CHLOROFORM-D) δ ppm 0.43-0.50 (m, 3H) 1.35 (d, J=6.82 Hz, 3H) 1.38-1.47 (m, 8H) 1.70 (s, 1H) 2.41-2.52 (m, J=12.51, 12.51, 12.38, 4.55 Hz, 1H) 2.54-2.62 (m, 1H) 3.48-3.54 (m, 3H) 3.59 (d, J=13.89 Hz, 1H) 3.82-3.88 (m, 1H) 3.90 (d, J=7.07 Hz, 1H) 7.17-7.21 (m, 3H) 7.23-7.28 (m, 4H) 7.36 (ddd, J=12.06, 7.33, 7.14 Hz, 4H).

Step 4

(3S,4R)-1-tert-Butyl 3-methyl 4-(benzyl((R)-1-phenylethyl)amino)-3-methylpiperidine-1,3-dicarboxylate (4.777 g, 10.24 mmol) was taken up in 100 mL of 4.4% formic acid in methanol. Palladium on Carbon (10%, 1.059 g) was added and the reaction mixture was stirred under a nitrogen atmosphere for 2 h at room temperature. Filtration through celite gave a colorless solution that was concentrated to give a colorless oil. The oil was combined with 4-(benzyloxy)benzene-1-sulfonyl chloride (4.377 g, 15.48 mmol) and equivalent volumes of $CH_2Cl_2$ and saturated sodium bicarbonate, and the resultant biphasic mixture was stirred vigorously overnight. The organic layer was separated and the remaining aqueous phase was washed with $CH_2Cl_2$ (3×). the organic extracts were combined, dried over Na$_2$SO$_4$ and concentrated to give a beige solid that was purified by chromatography on silica gel eluting with 30% ethyl acetate/hexanes to give (3S,4R)-1-tert-butyl 3-methyl 4-(4-(benzyloxy)phenylsulfonamido)-3-methylpiperidine-1,3-dicarboxylate as a white solid (4.523 g, 8.72 mmol, 85%). $^1$H NMR (400 MHz, CHLOROFORM-D) δ ppm 1.14 (s, 3H) 1.37-1.48 (m, 11H) 1.78 (s, 1H) 2.02-2.05 (m, 3H) 2.51 (s, 1H) 3.08-3.16 (m, 1H) 3.65 (s, 3H) 4.48 (s, 1H) 5.11 (s, 2H) 5.65 (d, J=9.60 Hz, 1H) 7.01-7.06 (m, 2H) 7.31-7.43 (m, 6H) 7.78-7.82 (m, 2H).

Step 5

To a mixture of (3S,4R)-1-tert-butyl 3-methyl 4-(4-(benzyloxy)phenylsulfonamido)-3-methylpiperidine-1,3-dicarboxylate (4.494 g, 8.67 mmol), 5 M NaOH (10 mL), and THF (20 mL) was added methanol until the reaction became homogeneous. The solution was stirred at 45° C. overnight, then diluted with pH 4 NaH$_2$PO$_4$ (aq) and extracted with ethyl acetate (3×). Combined organic extracts were dried over Na$_2$SO$_4$ and concentrated to give an orange solid. The solid was then combined with benzotriazol-1-yloxy-tris(dimethylamino)phosphonium hexafluorophosphate (BOP) (4.766 g, 10.78 mmol), O-tert-butylhydroxylamine hydrochloride (2.442 g, 19.28 mmol), triethylamine (5.4 mL), and DMF (10 mL) and the reaction mixture was stirred overnight at room temperature. The mixture was then diluted with brine and extracted with ethyl acetate (3×). The combined organic extracts were dried over Na$_2$SO$_4$ and purified via column chromatography on silica gel eluting with 30% ethyl acetate/hexanes to give (3S,4R)-tert-butyl 4-(4-(benzyloxy)phenylsulfonamido)-3-(tert-butoxycarbamoyl)-3-methylpiperidine-1-carboxylate (4.659 g, 8.09 mmol, 93%) as a colorless solid. $^1$H NMR (400 MHz, CHLOROFORM-D) δ ppm 1.09 (s, 3H) 1.23-1.25 (m, 9H) 1.40-1.51 (m, 10H) 1.57-1.60 (m, 3H) 1.65-1.72 (m, 1H) 2.49 (d, J=15.16 Hz, 1H) 2.72-2.83 (m, 1H) 3.16 (ddd, J=12.38, 8.72, 3.92 Hz, 1H) 3.98 (dt, J=13.58, 2.31 Hz, 1H) 4.31 (d, J=14.65 Hz, 1H) 5.11 (s, 2H) 7.01 (ddd, J=9.41, 2.78, 2.46 Hz, 2H) 7.33-7.44 (m, 5H) 7.78-7.82 (m, 2H).

Step 6

(3S,4R)-1-tert-Butyl 3-methyl 4-(4-(benzyloxy)phenylsulfonamido)-3-methylpiperidine-1,3-dicarboxylate (4.659 g, 8.09 mmol) was taken up in methanol (30 mL) and combined with Pearlman's catalyst (501 mg). The heterogeneous mixture was stirred under a hydrogen atmosphere for 0.5 h, and then filtered through celite and concentrated to give (3S,4R)-1-tert-butyl 3-methyl 4-(4-hydroxyphenylsulfonamido)-3-methylpiperidine-1,3-dicarboxylate (3.754 g, 7.73 mmol, 96%) as a colorless solid. $^1$H NMR (400 MHz, CHLOROFORM-D) δ ppm 1.16 (s, 3H) 1.24 (s, 9H) 1.37-1.48 (m, 10H) 1.68-1.77 (m, 2H) 2.54 (d, J=15.41 Hz, 1 H) 2.82 (td, J=13.20, 2.65 Hz, 1H) 3.27 (ddd, J=12.25, 8.59, 3.92 Hz, 1H) 4.00 (ddd, J=13.58, 2.53, 2.34 Hz, 1H) 4.33 (d, J=13.89 Hz, 1H) 6.85-6.89 (m, 2H) 7.67-7.72 (m, 2H).

Step 7

(3S,4R)-1-tert-Butyl 3-methyl 4-(4-hydroxyphenylsulfonamido)-3-methylpiperidine-1,3-dicarboxylate (3.754 g, 7.73 mol) was taken up in DMF (50 mL) and combined with cesium carbonate (6.162 g, 13.94 mmol), 4-(chloromethyl)-2-methylquinoline (3.115 g, 13.66 mmol) and catalytic sodium iodide. The reaction mixture was stirred at room temperature under a N$_2$ atmosphere for 3 days and then diluted with ethyl acetate. The aqueous layer was separated and extracted with ethyl acetate a second time. The combined organic extracts were washed with brine (2×), saturated aqueous Na$_2$CO$_3$ (2×), and brine (2×), then dried over Na$_2$SO$_4$ and concentrated to give a brown oil. This oil was purified via column chromatography on silica gel eluting with 50% ethyl acetate/hexanes to give (3S,4R)-tert-butyl 4-(4-(benzyloxy)phenylsulfonamido)-3-(tert-butoxycarbamoyl)-3-methylpiperidine-1-carboxylate (1.838 g, 2.87 mmol, 37%) as a yellow oil. $^1$H NMR (400 MHz, CHLOROFORM-D) δ ppm 1.09 (s, 3H) 1.25 (s, 9H) 1.43 (s, 9H) 1.47-1.56 (m, 1 H) 1.66-1.75 (m, 1H) 2.51 (d, J=15.16 Hz, 1H) 2.73 (s, 3H) 2.74-2.85 (m, 1H) 3.18 (ddd, J=12.19, 8.53, 3.79 Hz, 1H) 3.97-4.05 (m, 1H) 4.34 (d, J=14.91 Hz, 1 H) 5.51 (s, 2H) 7.06-7.11 (m, 2H) 7.39-7.43 (m, 1H) 7.53 (td, J=7.64, 1.14 Hz, 1H) 7.67-7.72 (m, 1H) 7.81-7.87 (m, 2H) 7.90 (d, J=8.34 Hz, 1H) 8.07 (d, J=7.83 Hz, 1H).

Step 8

(3S,4R)-tert-Butyl 4-(4-(benzyloxy)phenylsulfonamido)-3-(tert-butoxycarbamoyl)-3-methylpiperidine-1-carboxylate (1.790 g, 2.79 mmol) was dissolved in 50 mL of trifluoroacetic acid/CH$_2$Cl$_2$ (1:1, v:v) and stirred for 0.5 h at room temperature. The reaction mixture was concentrated, and the resultant yellow oil was treated with saturated aqueous Na$_2$CO$_3$ and then extracted with ethyl acetate (3×). The combined organic extracts were dried over Na$_2$SO$_4$ and concentrated to give (3S,4R)-N-tert-butoxy-3-methyl-4-(4-((2-methylquinolin-4-yl)methoxy)phenylsulfonamido)piperidine-3-carboxamide (1.492 g, 2.76 mmol, quant.) as a colorless solid. $^1$H NMR (400 MHz, DMSO-D6) δ ppm 0.94 (s, 3H) 1.17 (s, 9H) 1.47-1.58 (m, 1H) 2.31 (d, J=12.63 Hz, 1H) 2.50 (ddd, J=3.66, 2.02, 1.89 Hz, 4H) 2.65-2.67 (m, 3H) 2.80 (s, 2H) 3.09 (d, J=12.63 Hz, 1H) 3.33 (s, 2H) 5.72 (s, 2H) 7.28-7.33 (m, 2H) 7.54 (s, 1H) 7.59 (td, J=7.64, 1.14 Hz, 1H) 7.72-7.78 (m, 1H) 7.82-7.87 (m, 2H) 7.98 (d, J=7.83 Hz, 1H) 8.11 (d, J=7.58 Hz, 1H).

Step 9

(3S,4R)-N-tert-butoxy-3-methyl-4-(4-((2-methylquinolin-4-yl)methoxy)phenylsulfonamido)piperidine-3-carboxamide (323 mg, 0.597 mmol) was dissolved in CH$_2$Cl$_2$ (5 mL). The solution was cooled to 0° C., then triethylamine (100 µL) and acetylchloride (50 µL) were added. The reaction was stirred for 1 h, then diluted with ethyl acetate and washed with saturated aqueous Na$_2$CO$_3$ (2×) and brine (2×). The organic layer was isolated, dried over Na$_2$SO$_4$, concentrated, and then purified via column chromatography on silica gel eluting with 5% MeOH/CH$_2$Cl$_2$ to give (3S,4R)-1-acetyl-N-tert-butoxy-3-methyl-4-(4-((2-methylquinolin-4-yl)methoxy)phenylsulfonamido)piperidine-3-carboxamide (341 mg, 0.585 mmol, quant) as a colorless solid. $^1$H NMR (400 MHz, CHLOROFORM-D) δ ppm 1.09 (s, 3H) 1.22-1.28 (m, 9H) 1.55 (qd, J=12.93, 4.67 Hz, 1H) 1.88 (ddd, J=13.52, 2.78, 2.65 Hz, 1H) 2.07-2.10 (m, 3H) 2.33-2.39 (m, 1H) 2.75 (s, 3H) 3.09-3.18 (m, 1H) 3.24 (ddd, J=12.19, 8.53, 3.79 Hz, 1H) 3.78 (dt, J=13.58, 2.18 Hz, 1H) 4.76 (dd, J=14.91, 2.53 Hz, 1H) 5.55 (s, 2H) 7.08-7.14 (m, 2H) 7.42 (s, 1H) 7.53-7.58 (m, 1H) 7.70-7.75 (m, 1H) 7.83-7.87 (m, 2H) 7.89-7.93 (m, 1H) 8.07-8.11 (m, 1H) 9.93 (s, 1H).

Step 10

(3S,4R)-1-Acetyl-N-tert-butoxy-3-methyl-4-(4-((2-methylquinolin-4-yl)methoxy)phenylsulfonamido)piperidine-3-carboxamide (326 mg, 0.559 mmol) was dissolved in trifluoroacetic acid (5 mL) and heated at 40° C. overnight. The solvent was concentrated and the residual oil was treated with saturated aqueous NaHCO$_3$ and extracted with ethyl acetate (3×). The combined organic extracts were dried over Na$_2$SO$_4$, then purified via column chromatography on silica gel eluting with 5% MeOH/CH$_2$Cl$_2$ to give (3S,4R)-1-acetyl-N-hydroxy-3-methyl-4-[({4-[(2-methylquinolin-4-yl)methoxy]

phenyl}sulfonyl)amino]piperidine-3-carboxamide (70 mg, 0.133 mmol, 24%) as a colorless solid. LCMS (M−H): 1.58 min, 525.4; $^1$H NMR (400 MHz, MeOD) δ ppm 0.97 (s, 2H) 1.09-1.20 (m, 4H) 1.44 (d, J=13.14 Hz, 1H) 1.65-1.75 (m, 1H) 1.90-1.97 (m, 5H) 2.55 (d, J=14.40 Hz, 2H) 2.60-2.64 (m, 4H) 2.93-3.03 (m, 1H) 3.05-3.16 (m, 2H) 3.67 (s, 1H) 5.58 (s, 3H) 7.16 (d, J=9.09 Hz, 3H) 7.46-7.54 (m, 3H) 7.62-7.69 (m, 2H) 7.78 (dd, J=8.97, 2.15 Hz, 3H) 7.90 (d, J=8.59 Hz, 2H) 7.99 (d, J=8.08 Hz, 2H).

Example 48

(3S,4R)-N-hydroxy-1-isopropyl-3-methyl-4-[({4-[(2-methylquinolin-4-yl)methoxy]phenyl}sulfonyl)amino]piperidine-3-carboxamide

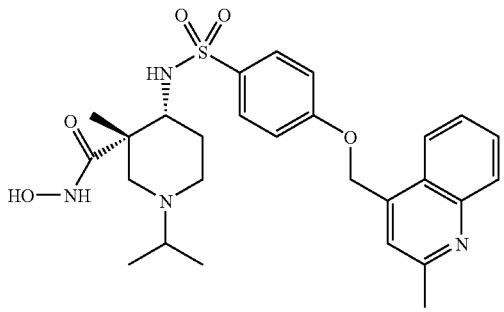

Step 1

To 324 mg (0.599 mmol) of (3S,4R)-N-tert-butoxy-3-methyl-4-(4-((2-methylquinolin-4-yl)methoxy)phenylsulfonamido)piperidine-3-carboxamide (Example 47, Step 8) was added methanol (5 mL), acetic acid (300 μL), acetone (135 μL), and sodium cyanoborohydride (61 mg, 0.971 mmol) and the resulting reaction was stirred at room temperature overnight. The reaction mixture was then concentrated and the residue was taken up in saturated aqueous sodium carbonate and extracted with ethyl acetate (3×). the combined organic extracts were dried over $Na_2SO_4$ and purified using column chromatography on silica gel eluting with 1% methanol/$CH_2Cl_2$ to give (3S,4R)-N-tert-butoxy-1-isopropyl-3-methyl-4-(4-((2-methylquinolin-4-yl)methoxy)phenylsulfonamido)piperidine-3-carboxamide (205 mg, 0.352 mmol, 59%) as a colorless solid. $^1$H NMR (400 MHz, CHLOROFORM-D) δ ppm 0.91 (s, 3H) 1.05 (dd, J=6.57, 1.26 Hz, 5H) 1.23-1.26 (m, 8H) 1.55-1.64 (m, 4H) 1.95 (dd, J=13.64, 4.04 Hz, 1H) 2.09 (d, J=12.38 Hz, 1H) 2.27 (td, J=12.13, 3.03 Hz, 1H) 2.73-2.81 (m, 4H) 2.85 (d, J=4.29 Hz, 1H) 2.91-3.01 (m, 2H) 5.57 (d, J=1.01 Hz, 2H) 6.01 (d, J=7.33 Hz, 1H) 7.09 (ddd, J=9.41, 2.78, 2.46 Hz, 2H) 7.42 (s, 1H) 7.56 (ddd, J=8.34, 7.07, 1.26 Hz, 1H) 7.74 (ddd, J=8.46, 6.95, 1.26 Hz, 1H) 7.83-7.87 (m, 2H) 7.89-7.94 (m, 1H) 8.09 (d, J=7.83 Hz, 1H).

Step 2

According to the procedure of Example 47, Step 10, (3S,4R)-N-tert-butoxy-1-isopropyl-3-methyl-4-(4-((2-methylquinolin-4-yl)methoxy)phenylsulfonamido)piperidine-3-carboxamide (167 mg, 0.287 mmol) was hydrolyzed and then purified via column chromatography on silica gel eluting with10% methanol/$CH_2Cl_2$ to give (3S,4R)-N-hydroxy-1-isopropyl-3-methyl-4-[({4-[(2-methylquinolin-4-yl)methoxy]phenyl}sulfonyl)amino]piperidine-3-carboxamide (90 mg, 0.171 mmol, 60%) as a colorless solid. LCMS (M−H): 2.03 min, 525.3; $^1$H NMR (400 MHz, CHLOROFORM-D) δ ppm 0.88-0.93 (m, 3H) 1.00-1.07 (m, 5H) 1.54-1.66 (m, J=12.88, 12.88, 12.76, 4.17 Hz, 1H) 1.83-1.93 (m, 1H) 2.00-2.08 (m, 1H) 2.25 (td, J=12.13, 2.78 Hz, 1H) 2.74-2.77 (m, 3H) 2.78-2.87 (m, 2H) 2.88-2.96 (m, 2H) 3.46-3.50 (m, 3H) 5.57 (s, 2H) 7.08-7.15 (m, 2H) 7.43 (s, 1H) 7.53-7.59 (m, 1H) 7.73 (ddd, J=8.46, 6.95, 1.26 Hz, 1H) 7.85-7.93 (m, 3H) 8.10 (d, J=8.59 Hz, 1H).

Example 49

(3S,4R)-N-hydroxy-3-methyl-4-[({4-[(2-methylquinolin-4-yl)methoxy]phenyl}sulfonyl)amino]-1-prop-2-yn-1-ylpiperidine-3-carboxamide

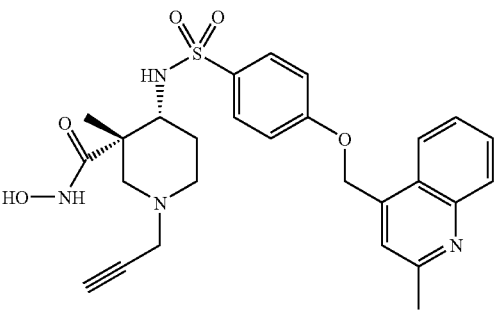

Step 1

To 364 mg (0.673 mmol) of (3S,4R)-N-tert-butoxy-3-methyl-4-(4-((2-methylquinolin-4-yl)methoxy)phenylsulfonamido)piperidine-3-carboxamide (Example 47, Step 8) was added ethanol (6 mL), catalytic sodium iodide, potassium carbonate (112 mg, 0.812 mmol), and propargyl chloride (52 μL) and the resulting mixture was heated to reflux overnight. The solvent was then concentrated and the residue was dissolved in ethyl acetate. The organics were washed with saturated aqueous $Na_2CO_3$ (3×), dried over $Na_2SO_4$, concentrated, and then purified via column chromatography on silica gel eluting with 50% ethyl acetate/hexanes to give (3S,4R)-N-tert-butoxy-3-methyl-4-(4-((2-methylquinolin-4-yl)methoxy)phenylsulfonamido)-1-(prop-2-ynyl)piperidine-3-carboxamide (235 mg, 0.406 mmol, 60%) as a colorless solid. $^1$H NMR (400 MHz, CHLOROFORM-D) δ ppm 0.92-0.96 (m, 3H) 1.23-1.30 (m, 11H) 1.60-1.71 (m, 1H) 1.89-1.97 (m, 1H) 2.05-2.12 (m, 1H) 2.27-2.36 (m, 2H) 2.74 (s, 3H) 2.84-2.91 (m, 1H) 3.00 (ddd, J=12.06, 7.52, 4.17 Hz, 1H) 3.14 (dd, J=10.74, 2.15 Hz, 1H) 3.16-3.20 (m, 1H) 3.34 (dd, J=16.67, 2.53 Hz, 1H) 5.54 (s, 2H) 6.16 (d, J=7.58 Hz, 1H) 7.07-7.12 (m, 2H) 7.41 (s, 1H) 7.52-7.57 (m, 1H) 7.71 (ddd, J=8.46, 6.95, 1.26 Hz, 1H) 7.81-7.86 (m, 2H) 7.90 (d, J=7.58 Hz, 1H) 8.08 (d, J=8.59 Hz, 1H) 10.71 (s, 1H).

Step 2

According to the procedure of Example 47, Step 10, (3S,4R)-N-tert-butoxy-3-methyl-4-(4-((2-methylquinolin-4-yl)methoxy)phenylsulfonamido)-1-(prop-2-ynyl)piperidine-3-carboxamide (205 mg, 0.354 mmol) was hydrolyzed and then purified via HPLC (15-100% acetonitrile/water, 10 min) to give (3S,4R)-N-hydroxy-3-methyl-4-[({4-[(2-methylquinolin-4-yl)methoxy]phenyl}sulfonyl)amino]-1-prop-2-yn-1-ylpiperidine-3-carboxamide (126 mg, 0.241 mmol, 68%) as a colorless solid. LCMS (M−H): 0.44 min, 521.4; $^1$H NMR (400 MHz, ACETONITRILE-D3) δ ppm 0.94 (s, 3H) 1.70 (td, J=12.95, 4.42 Hz, 1H) 1.76-1.82 (m, 1H) 2.21-2.28 (m, 7H) 2.39 (td, J=11.81, 3.16 Hz, 1H) 2.79 (s, 3H) 2.86-2.94 (m, 1H) 2.98-3.06 (m, 2H) 3.40 (td, J=16.67, 2.53 Hz, 2H) 5.76 (s, 2H) 6.09 (d, J=8.08 Hz, 1H) 7.31-7.36 (m, 2H) 7.63 (s, 1H) 7.69 (ddd, J=8.34, 7.07, 1.26 Hz, 1H) 7.85 (ddd, J=8.34, 6.95, 1.39Hz, 1H) 7.94-7.98 (m, 2H) 8.10 (d, J=8.59 Hz, 1H) 8.16 (d, J=8.34 Hz, 1H).

Example 50

(3S,4R)-N-3-Hydroxy-N-1-,3-dimethyl-4-[({4-[(2-methylquinolin-4-yl)methoxy]phenyl}sulfonyl)amino]piperidine-1,3-dicarboxamide)

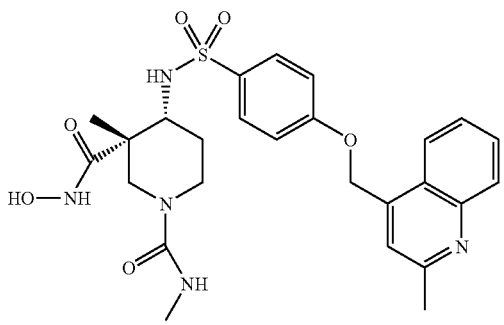

Step 1

To 366 mg (0.677 mmol) of (3S,4R)-N-tert-butoxy-3-methyl-4-(4-((2-methylquinolin -4-yl)methoxy)phenylsulfonamido)piperidine-3-carboxamide (Example 47, Step 8) in THF (6 mL) was added methyl isocyanate (129 mg, 2.26 mmol). The solution was stirred for 1 h and then concentrated, and the residue was purified via preparative TLC (5% MeOH/CH$_2$Cl$_2$) to give (3S,4R)-N-3-(tert-butoxy)-N-1-,3-dimethyl-4-[({4-[(2-methylquinolin-4-yl)methoxy]phenyl}sulfonyl)amino]piperidine-1,3-dicarboxamide (309 mg, 0.517 mmol, 76%) as a colorless solid. $^1$H NMR (400 MHz, CHLOROFORM-D) δ ppm 0.98-1.02 (m, 3H) 1.22-1.28 (m, 11H) 1.45-1.56 (m, J=12.76, 12.76, 12.51, 4.42 Hz, 1H) 1.83 (dd, J=13.26, 2.40 Hz, 1H) 2.40 (d, J=14.91 Hz, 1H) 2.75 (td, J=10.48, 4.29 Hz, 6H) 2.97 (td, J=12.88, 2.78 Hz, 1H) 3.14 (ddd, J=12.13, 8.21, 3.92 Hz, 1H) 3.53 (dd, J=10.74, 2.15 Hz, 1H) 4.50 (dd, J=14.91, 2.02 Hz, 1H) 4.87 (q, J=4.21 Hz, 1H) 5.55 (s, 2H) 7.09 (ddd, J=9.47, 2.78, 2.40 Hz, 2H) 7.42 (s, 1H) 7.45-7.49 (m, 1H) 7.52-7.58 (m, 1H) 7.72 (ddd, J=8.34, 6.95, 1.39 Hz, 1H) 7.84 (ddd, J=9.41, 2.78, 2.46 Hz, 2H) 7.88-7.93 (m, 1H) 8.07 (d, J=8.59 Hz, 1H).

Step 2

According to the procedure of Example 47, Step 10, (3S, 4R)-N-3-(tert-butoxy)-N-1,3-dimethyl-4-[({4-[(2-methylquinolin-4-yl)methoxy]phenyl}sulfonyl)amino]piperidine-1,3-dicarboxamide (288 mg; 0.482 mmol) was hydrolyzed and then purified via preparative TLC (10% MeOH/CH$_2$Cl$_2$) to give (3S,4R)-N-3-hydroxy-N-1-,3-dimethyl-4-[({4-[(2-methylquinolin-4-yl)methoxy]phenyl}sulfonyl)amino]piperidine-1,3-dicarboxamide (58 mg, 0.107 mmol, 22%) as a colorless solid. LCMS (M–H): 1.60 min, 540.4; $^1$H NMR (400 MHz, CHLOROFORM-D) δ ppm 0.93-0.96 (m, 2H) 1.44-1.56 (m, 2H) 1.93 (d, J=14.65 Hz, 1H) 2.42 (d, J=15.16 Hz, 1H) 2.75 (s, 3H) 2.83 (d, J=4.55 Hz, 3H) 2.98-3.07 (m, 1H) 3.17 (ddd, J=12.13, 8.21, 3.66 Hz, 1H) 3.49-3.57 (m, 1H) 4.43 (dd, J=15.16, 2.53 Hz, 1H) 5.57 (s, 2H) 7.08-7.14 (m, 2H) 7.42 (s, 1H) 7.56 (ddd, J=8.27, 6.88, 1.26 Hz, 1H) 7.74 (ddd, J=8.46, 6.95, 1.26 Hz, 1H) 7.84-7.93 (m, 3H) 8.10 (d, J=8.59 Hz, 1H).

Example 51

(3S,4R)-1-formyl-N-hydroxy-3-methyl-4-[({4-[(2-methylquinolin-4-yl)methoxy]phenyl}sulfonyl)amino]piperidine-3-carboxamide

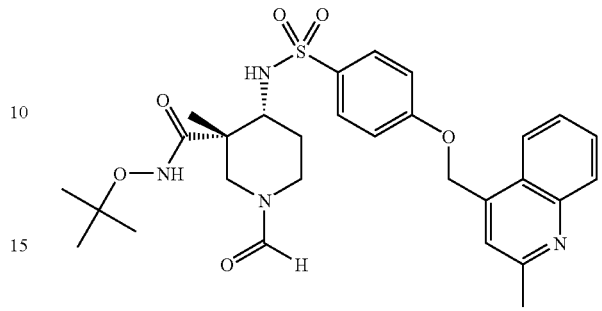

Step 1

To a solution of 0.15 g (0.28 mmol) of (3S,4R)-N-tert-butoxy-3-methyl-4-(4-((2-methylquinolin-4-yl)methoxy)phenylsulfonamido)piperidine-3-carboxamide (Example 47, Step 8) in methanol (0.5 mL) was added ethyl formate (3 mL) followed by diisopropylethylamine (0.2 mL, 1.1 mmol). The reaction mixture was stirred at 48° C. for 18 h and concentrated. The residue was purified using silica chromatography, eluting with a gradient of 1-5% MeOH/CH$_2$Cl$_2$ to afford (3S,4R)-N-tert-butoxy-1-formyl -3-methyl-4-(4-((2-methylquinolin-4-yl)methoxy)phenylsulfonamido)piperidine-3-carboxamide (0.092 g, 58%). MS: 569.1 (M+H)$^+$ Step 2

To 0.092 g of (3S,4R)-N-tert-butoxy-1-formyl-3-methyl-4-(4-((2-methylquinolin-4-yl)methoxy)phenylsulfonamido) piperidine-3-carboxamide was added 3 mL of trifluoroacetic acid, and the resulting mixture was stirred at 45° C. for 8 h, and then concentrated. The residue was purified by silica chromatography (silica pre-washed with MeOH), eluting with a gradient of 5-20% MeOH/CH$_2$Cl$_2$ to afford (3S,4R)-1-formyl -N-hydroxy-3-methyl-4-[({4-[(2-methylquinolin-4-yl)methoxy]phenyl}sulfonyl)amino]piperidine-3-carboxamide (0.05 g, 60%) as a colorless solid. MS: 513.2 (M+H)$^+$

Example 52

(3S,4R)-N-hydroxy-1-(isopropylsulfonyl)-3-methyl-4-[({4-[(2-methylquinolin-4-yl)methoxy]phenyl}sulfonyl)amino]piperidine-3-carboxamide

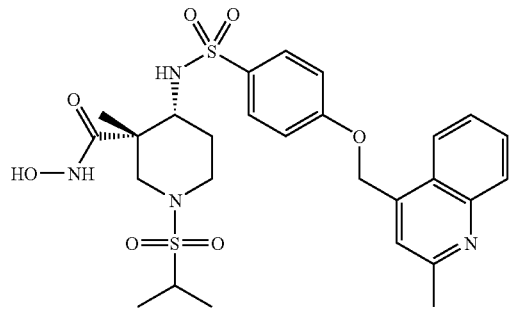

Step 1

To a solution of 0.15 g (0.28 mmol) of (3S,4R)-N-tert-butoxy-3-methyl-4-(4-((2-methylquinolin-4-yl)methoxy)phenylsulfonamido)piperidine-3-carboxamide (Example 47, Step 8) in CH$_2$Cl$_2$ (1.3 mL) was added 3 mL of saturated sodium bicarbonate followed by isopropylsulfonyl chloride (0.1 mL, 0.9 mmol). The reaction mixture was stirred overnight, taken up in ethyl acetate, washed with brine, dried over MgSO$_4$, filtered and concentrated. The residue was purified by silica chromatography (silica pre-washed with methanol) eluting with a gradient of 1-5% MeOH/CH$_2$Cl$_2$ to afford (3S,4R)-N-tert-butoxy-1-(isopropylsulfonyl)-3-methyl-4-[({4-[(2-methylquinolin-4-yl)methoxy]phenyl}sulfonyl)amino]piperidine-3-carboxamide (0.12 g, 66%) as a colorless solid. MS: 647.2 (M+H)$^+$ Step 2

To 0.11 g of (3S,4R)-N-tert-butoxy-1-(isopropylsulfonyl)-3-methyl-4-[({4-[(2-methylquinolin-4-yl)methoxy]phenyl}sulfonyl)amino]piperidine-3-carboxamide was added 3 mL of trifluoroacetic acid and the resulting mixture was stirred at 45° C. for 8 h. The reaction mixture was then concentrated and the residue was purified by silica chromatography (silica prewashed with MeOH) eluting with a gradient of 5-20% MeOH/CH$_2$Cl$_2$ to afford (3S,4R)-N-hydroxy-1-(isopropylsulfonyl)-3-methyl-4-[({4-[(2-methylquinolin-4-yl)methoxy]phenyl}sulfonyl)amino]piperidine-3-carboxamide (0.091 g, 83%) as a colorless solid. MS: 591.2 (M+H)$^+$ Example 53

(1R,2R)-N,1-dihydroxy-2-[({4-[(2-methylquinolin-4-yl)methoxy]phenyl}sulfonyl)amino]cyclopentanecarboxamide

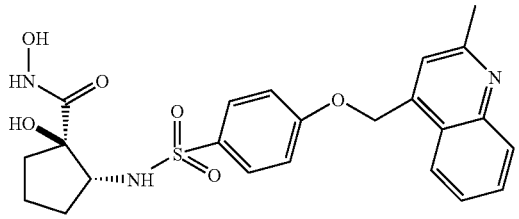

Step 1

According to the procedure of Tet. Asymm., 13, 2002, 1555: To a solution of (R)-N-benzyl-N-α-methylbenzylamine (1.37 mL, 2 eq.) in THF (10 mL) at −78° C. was added n-butyllithium (2.4 M, 2.2 mL, 1.6 eq). The reaction was allowed to stir for 30 min at −78° C. and then methyl 1-cyclopentene-1-carboxylate (0.41 mL, 3.25 mmol, 1 eq) was added dropwise. The reaction was stirred for 3 h at −78° C. and then a solution of (1R)-(−)-(10-camphorsulfonyl)oxaziridine (1.49 g, 2 eq) in THF (12 mL) was added dropwise via cannula. The reaction was allowed to stir at room temperature overnight, and was then taken up in ethyl acetate, washed with NaHCO$_3$ (1×), brine (2×), dried over Na$_2$SO$_4$, filtered and concentrated. Purification by silica chromatography eluting with a gradient of 10-15% ethyl acetate/hexanes afforded methyl (1R,2R)-2-{benzyl[(1R)-1-phenylethyl]amino}-1-hydroxycyclopentanecarboxylate as an off white solid (0.77 g, 69%). MS: 354.2 (M+H)$^+$ Step 2

To a solution of methyl (1R,2R)-2-{benzyl[(1R)-1-phenylethyl]amino}-1-hydroxycyclopentanecarboxylate (0.75 g, 2.1 mmol) in methanol (30 mL) was added formic acid (1.44 mL) and 10% Pd/C (0.5 g). The mixture was purged with nitrogen followed by hydrogen and allowed to stir at 40° C. for 3 h under 1 atmosphere of hydrogen. The reaction mixture was then filtered through celite. Hydrochloric acid (1 mL, 12 M) was added to the filtrate, which was then concentrated and chased three times with methanol/benzene (1:1) to afford methyl (1R,2R)-2-amino-1-hydroxycyclopentanecarboxylate as a white solid (0.415 g, 100%). MS: 160.1 (M+H)$^+$ Step 3

To a solution of methyl (1R,2R)-2-amino-1-hydroxycyclopentanecarboxylate (2.1 mmol) in CH$_2$Cl$_2$ (8 mL) and saturated sodium bicarbonate (8 mL) was added 4-(2-methylquinolin-4-ylmethoxy)-benzenesulfonyl chloride hydrochloride (0.88 g, 1.1 eq). The reaction was allowed to stir for 18 h at room temperature, and then taken up in ethyl acetate, washed with brine, dried over MgSO$_4$, filtered and concentrated. The residue was purified using ilica chromatography eluting with a gradient of 50% -70% ethyl acetate/hexanes afforded methyl (1R,2R)-1-hydroxy-2-[({4-[(2-methylquinolin-4-yl)methoxy]phenyl}sulfonyl)amino]cyclopentanecarboxylate (0.2 g, 20%). MS: 470.1 (M+H)$^+$ Step 4

To a solution of methyl (1R,2R)-1-hydroxy-2-[({4-[(2-methylquinolin-4-yl)methoxy]phenyl}sulfonyl)amino]cyclopentanecarboxylate (0.19 g, 0.4 mmol) in THF (2 mL) was added sodium hydroxide solution (5 M, 2 mL) and methanol (2 mL) to make the reaction mixture homogenous. The reaction was stirred for 5 h, and then the MeOH/THF was removed in vacuo. The reaction was quenched with a pH 3 sodium phoshphate buffer. Ethyl acetate was added to this mixture, resulting in the formation of a white precipitate which was isolated by filtration to afford (1R,2R)-1-hydroxy-2-[({4-[(2-methylquinolin-4-yl)methoxy]phenyl}sulfonyl)amino]cyclopentanecarboxylic acid (0.8 g, 42%) as a white solid. MS: 457.0 (M+H)$^+$ Step 5

To a solution of (1R,2R)-1-hydroxy-2-[({4-[(2-methylquinolin-4-yl)methoxy]phenyl}sulfonyl)amino]cyclopentanecarboxylic acid (0.08 g) in DMF (0.8 mL) was added hydroxylamine hydrochloride (2 eq), benzotriazol-1-yloxy-tris(dimethylamino)-phosphonium hexafluorophosphate (1.3 eq) and diisopropylethylamine (4 eq). The reaction was stirred overnight and injected directly onto a reverse phase HPLC (CH$_3$CN/H$_2$O) to afford (1R,2R)-N,1-dihydroxy-2-[({4-[(2-methylquinolin-4-yl)methoxy]phenyl}sulfonyl)amino]cyclopentanecarboxamide (0.03 g, 37%) as a white solid. MS: 472.1 (M+H)$^+$ Example 54

(1R,2R)-1-fluoro-N-hydroxy-2-[((4-[(2-methylquinolin-4-yl)methoxy]phenyl}sulfonyl)amino]cyclopentanecarboxamide

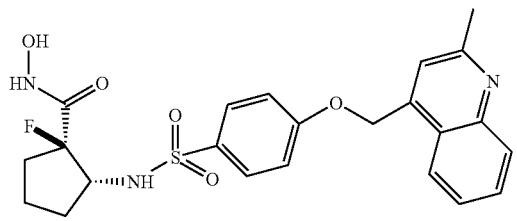

Step 1

According to the procedure of Example 53, Step 1, except the intermediate enolate was treated with N-fluorobenzenesulfonimide (2 eq) instead of (−)-camphorsulfonyl)oxaziridine, methyl (1R,2R)-2-{benzyl[(1R)-1-phenylethyl]amino}-1-fluorocyclopentanecarboxylate was obtained as an oil (1.16 g, 65%) after purification by silica chromatography eluting with a gradient of 2-5% ethyl acetate/hexanes. MS: 356.2 (M+H)+.

Step 2

According to the procedure of Example 53, Step 2, methyl (1R,2R)-2-{benzyl[(1R)-1-phenylethyl]amino}-1-fluorocyclopentanecarboxylate afforded methyl (1R,2R)-2-amino-1-fluorocyclopentanecarboxylate as an oil (0.525 g, 86%). MS: 162.1 (M+H)+.

Step 3

To a solution of methyl (1R,2R)-2-amino-1-fluorocyclopentanecarboxylate (0.47 g, 2.4 mmol, 1 eq) in $CH_2Cl_2$ (10 mL) was added 4-benzyloxy-benzenesulfonyl chloride followed by saturated sodium bicarbonate (10 mL). The reaction was stirred overnight, and then taken up in ethyl acetate. The organics were washed with brine, dried over $MgSO_4$, filtered and concentrated. The residue was purified using silica chromatography eluting with 30% ethyl acetate/hexanes to afford methyl (1R,2R)-2-({[4-(benzyloxy)phenyl]sulfonyl}amino)-1-fluorocyclopentanecarboxylate as an off white solid (0.575 g, 60%). MS: 408.1 (M+H)+.

Step 4

To a solution of methyl (1R,2R)-2-({[4-(benzyloxy)phenyl]sulfonyl}amino)-1-fluorocyclopentanecarboxylate in EtOAc/$CH_2Cl_2$/MeOH (5 mL/2 mL/10 mL) was added 10% Pd/C (0.14 g). The reaction vessel was purged with nitrogen followed by hydrogen. The reaction was stirred for 1 h under 1 atmosphere of hydrogen, and then filtered through celite and concentrated to afford methyl (1R,2R)-1-fluoro-2-{[(4-hydroxyphenyl)sulfonyl]amino}cyclopentanecarboxylate as an amorphous solid (0.433 g, 97%). MS: 318.1 (M+H)+.

Step 5

To a solution of methyl (1R,2R)-1-fluoro-2-{[(4-hydroxyphenyl)sulfonyl]amino}cyclopentanecarboxylate (0.42 g, 1.3 mmol, 1 eq) in DMF (4 mL) was added cesium carbonate (0.86 g, 2 eq) followed by 4-chloromethyl-2-methyl-quinoline. The brown reaction mixture was stirred for 3 days, and then taken up in ethyl acetate, washed with brine, dried over $Na_2SO_4$, filtered and concentrated. Purification using silica chromatography eluting with 40-70% ethyl acetate/hexanes afforded methyl (1R,2R)-1-fluoro-2-[({4-[(2-methylquinolin-4-yl)methoxy]phenyl}sulfonyl)amino]cyclopentanecarboxylate as an off white solid (0.23 g, 41%). MS: 473.1 (M+H)+.

Step 6

Following the procedure of Example 53, Step 4, 1-fluoro-2-[4-(2-methyl-quinolin-4-ylmethoxy)-benzenesulfonylamino]-cyclopentanecarboxylic acid methyl ester provided (1R,2R)-1-fluoro-2-[({4-[(2-methylquinolin-4-yl)methoxy]phenyl}sulfonyl)amino]cyclopentanecarboxylic acid that was carried on to the next step without purification. MS: 459.1 (M+H)+

Step 7

To 0.15 g (3 mmol) of (1R,2R)-1-fluoro-2-[({4-[(2-methylquinolin-4-yl)methoxy]phenyl}sulfonyl)amino]cyclopentanecarboxylic acid in DMF (4 mL) was added benzotriazol-1-yloxytris(dimethylamino)-phosphonium hexafluorophosphate (0.16 g, 1.2 eq), tert-butyl hydroxylamine hydrochloride (0.078 g, 2 eq) and diisopropylethylamine (0.22 mL, 4 eq). The resulting reaction mixture was stirred for 18 h, and then taken up in ethyl acetate, washed with brine, dried over $Mg_2SO_4$, filtered and concentrated. The residue was purified using silica chromatography, eluting with a gradient of 50-80% ethyl acetate/hexanes to afford (1R,2R)-N-(tert-butoxy)-1-fluoro-2-[({4-[(2-methylquinolin-4-yl)methoxy]phenyl}sulfonyl)amino]cyclopentanecarboxamide (0.14 g, 60%, 2 steps). MS: 530.2 (M+H)+.

Step 8

Triethylsilane (0.1 mL, 0.63 mmol) was added to a solution of (1R,2R)-N-(tert-butoxy)-1-fluoro-2-[({4-[(2-methylquinolin-4-yl)methoxy]phenyl}sulfonyl)amino]cyclopentane carboxamide (0.13 g, 0.25 mmol) in trifluoroacetic acid (2 mL). The reaction mixture was stirred at 45° C. for 7 h, and then concentrated and chased three times with methanol/toluene. The residue was purified using silica chromatography, eluting with a gradient of 5-10% MeOH/$CH_2Cl_2$ to afford (1R,2R)-1-fluoro-N-hydroxy-2-[({4-[(2-methylquinolin-4-yl)methoxy]phenyl}sulfonyl)amino]cyclopentanecarboxamide (0.106 g, 91%). MS: 474.1 (M+H)+

Example 55

(1S,2R)-N-hydroxy-1-methyl-2-[({4-[(2-methylquinolin4-yl)methoxy]phenyl}sulfonyl)amino]cyclopentanecarboxamide

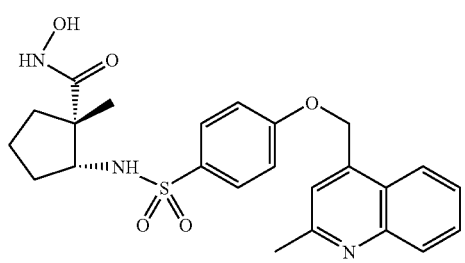

Step 1

According to the procedure of Example 53, Step 1, using (R)-N-benzyl-N-α-methylbenzylamine (4.2 mL, 4.24 g, 20 mmol), n-butyllithium (2.4 M, 7.4 mL), methyl 1-cyclopentene-1-carboxylate (1.3 mL, 1.29 g, 10.2 mmol), and iodomethane (1.3 mL). methyl (1S,2R)-2-{benzyl[(1 R)-1-phenylethyl]amino}-1-methylcyclopentanecarboxylate (2.804 g, 7.97 mmol, 78%) was obtained as a brown oil after column chromatography on silica gel eluting with 5% ethyl acetate/hexanes. $^1$H NMR (400 MHz, CHLOROFORM-D) δ ppm 0.63 (s, 3H) 1.18-1.29 (m, 5H) 1.52-1.64 (m, 1H) 1.74-1.83 (m, J=12.44, 7.67, 7.67, 2.53 Hz, 1H) 1.85-1.92 (m, 1H) 2.03-2.12 (m, 3H) 2.88 (dd, J=10.86, 7.33 Hz, 1H) 3.50-3.54 (m, 3H) 3.57-3.64 (m, 1H) 3.72-3.77 (m, 1H) 3.83 (q, J=6.82 Hz, 1H) 7.17-7.21 (m, 1H) 7.24-7.35 (m, 6H) 7.50 (d, J=7.33 Hz, 2H).

Step 2

According to the procedure of Example 53, Step 2, using methyl (1S,2R)-2-{benzyl[(1R)-1-phenylethyl]amino}-1-methylcyclopentanecarboxylate (1.025 g, 2.92 mmol), 4.4% $HCO_2H$/MeOH (30 mL) and 10% Pd/C (1.058 g), methyl (1S,2R)-2-amino -1-methylcyclopentanecarboxylate (527 mg, 2.72 mmol, 93%) was obtained as a colorless solid. $^1$H NMR (400 MHz, DMSO-D6) δ ppm 1.29 (s, 3H) 1.56-1.62

(m, 1H) 1.64-1.76 (m, 3H) 2.07-2.13 (m, 1H) 2.15-2.22 (m, 1H) 3.24-3.31 (m, 1H) 3.64-3.71 (m, 3H) 8.18 (s, 3H).

Step 3

According to the procedure of Example 47, Step 4, using methyl (1S,2R)-2-amino-1-methylcyclopentanecarboxylate (480 mg, 2.48 mmol) and 4-(benzyloxy)benzene-1-sulfonyl chloride (0.692 g, 2.45 mmol), methyl (1S,2R)-2-({[4-(benzyloxy)phenyl]sulfonyl}amino)-1-methylcyclopentanecarboxylate was obtained (811 mg, 82%) as a colorless solid after purification via column chromatography on silica gel eluting with 25% ethyl acetate/hexane. $^1$H NMR (400 MHz, CHLOROFORM-D) δ ppm 1.20 (s, 3H) 1.45-1.56 (m, 3H) 1.68-1.77 (m, 1H) 2.10 (ddd, J=12.57, 8.53, 3.66 Hz, 1H) 3.27-3.36 (m, 1H) 3.64-3.67 (m, 3H) 5.10 (s, 2H) 5.61 (d, J=10.11 Hz, 1H) 7.00-7.05 (m, 2H) 7.31-7.43 (m, 5H) 7.78-7.83 (m, 2H).

Step 4

According to the procedure of Example 53, Step 4, using methyl (1S,2R)-2-({[4-(benzyloxy)phenyl]sulfonyl}amino)-1-methylcyclopentanecarboxylate (765 mg, 1.90 mmol), (1S,2R)-2-({[4-(benzyloxy)phenyl]sulfonyl}amino)-1-methylcyclopentanecarboxylic acid (745 mg, 1.90 mmol, quant) was obtained as a colorless solid. $^1$H NMR (400 MHz, CHLOROFORM-D) δ ppm 1.29 (s, 3H) 1.48-1.59 (m, 2H) 1.59-1.71 (m, 3H) 2.13-2.22 (m, 1H) 3.28-3.38 (m, 1H) 5.12 (s, 2H) 6.18 (d, J=10.36 Hz, 1H) 7.02-7.08 (m, 2H) 7.33-7.44 (m, 5H) 7.79-7.84 (m, 2H).

Step 5

According to the procedure of Example 53, Step 5, using (1S,2R)-2-({[4-(benzyloxy)phenyl]sulfonyl}amino)-1-methylcyclopentanecarboxylic acid (677 mg, 1.74 mmol), BOP (424 mg, 2.09 mmol), O-tert-butylhydroxylamine (480 mg, 3.82 mmol), and triethylamine (1.2 mL), (1S,5R)-6-{[4-(benzyloxy)phenyl]sulfonyl}-1-methyl -6-azabicyclo[3.2.0]heptan-7-one was obtained (480 mg, 1.29 mmol, 74%) as a colorless solid after purification via column chromatography on silica gel, eluting with 25% ethyl acetate/hexanes. $^1$H NMR (400 MHz, CHLOROFORM-D) δ ppm 1.19-1.28 (m, 1H) 1.30-1.41 (m, 4H) 1.47-1.58 (m, 2H) 1.75 (dt, J=12.69, 6.41 Hz, 1H) 2.02-2.11 (m, 1H) 2.21 (dd, J=14.15, 5.31 Hz, 1H) 4.10 (d, J=4.04 Hz, 1H) 5.11-5.16 (m, 2H) 7.04-7.10 (m, 2H) 7.35-7.44 (m, 5H) 7.92-7.97 (m, 2H).

Step 6

According to the procedure of Example 47, Step 6, using (1S,5R)-6-{[4-(benzyloxy)phenyl]sulfonyl}-1-methyl-6-azabicyclo[3.2.0]heptan-7-one (354 mg, 0.954 mmol) and catalytic 10% Pd/C, with ethyl acetate added to aid solubility, (1S,5R)-6-[(4-hydroxyphenyl)sulfonyl]-1-methyl-6-azabicyclo[3.2.0]heptan-7-one was obtained (291 mg, 100%) as a colorless oil. $^1$H NMR (400 MHz, CHLOROFORM-D) δ ppm 1.24-1.35 (m, 4H) 1.46-1.56 (m, 1H) 1.75 (dt, J=12.32, 6.09 Hz, 1H) 2.02 (dd, J=12.63, 5.56 Hz, 1H) 2.07-2.16 (m, 1H) 4.09 (d, J=4.04 Hz, 1H) 6.93 (s, 1H) 6.97 (d, J=8.84 Hz, 2H) 7.81 (d, J=8.84 Hz, 2H).

Step 7

To (1S,5R)-6-[(4-hydroxyphenyl)sulfonyl]-1-methyl-6-azabicyclo[3.2.0]heptan-7-one (291 mg, 1.04 mmol) was added cesium carbonate (1.011 g, 2.70 mmol) and 4-(chloromethyl) -2-methylquinoline (498 mg, 2.18 mmol) in acetonitrile (2 mL), with DMF to aid solubility. This reaction was stirred at room temperature overnight with partial β-lactam hydrolysis being observed. Water was then added to the reaction mixture and it was heated in a microwave for 5 min at 150° C. The mixture was then diluted with ethyl acetate, washed with water and brine. The aqueous layers were acidified to pH 4 with 1 M HCl and then extracted with ethyl acetate. The combined organic extracts were dried over Na$_2$SO$_4$)] and concentrated to give an orange oil that was carried on without further purification. The orange oil was combined with BOP (500 mg, 1.13 mmol), hydroxylamine hydrochloride (179 mg, 2.56 mmol), and triethylamine (710 μL) in DMF (3 mL). This mixture was stirred at room temperature overnight, the solids were filtered and the filtrate was purified by HPLC eluting with a gradient of 15-100% MeCN/H$_2$O (10 min) to give (1S,2R)-N-hydroxy-1-methyl-2-[({4-[(2-methylquinolin-4-yl)methoxy]phenyl}sulfonyl)amino]cyclopentanecarboxamide (107 mg, 0.228 mmol, 24%) as a colorless solid. LCMS (M–H): 1.72 min; 468.4; $^1$H NMR (400 MHz, DMSO-D6) δ ppm 1.07 (s, 3H) 1.41 (m, 3H) 1.54 (s, 1H) 1.99 (d, J=1.01 Hz, 1H) 2.60-2.70 (m, 3H) 3.13 (s, 1H) 5.72 (s, 2H) 7.27-7.36 (m, 2H) 7.53-7.65 (m, 2H) 7.73-7.85 (m, 2H) 7.98 (d, J=8.34 Hz, 1H) 8.10 (s, 1H).

Example 56

(1S,2R)-N-hydroxy-1-ethyl-2-[({4-[(2-methylquinolin-4-yl)methoxy]phenyl}sulfonyl)amino]cyclopentanecarboxamide

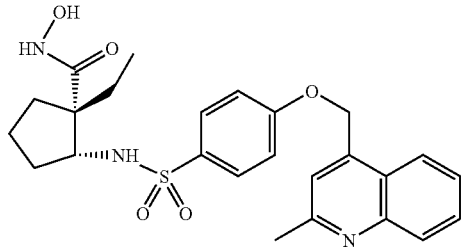

Step 1

According to the procedure of Example 53, Step 1, using (R)-N-benzyl-N-α-methylbenzylamine (4.2 mL, 4.24 g, 20 mmol), n-butyllithium (2.4 M, 7.4 mL), methyl 1-cyclopentene-1-carboxylate (1.3 mL, 1.29 g, 10.2 mmol), and iodoethane (1.6 mL, 3.12 g, 20 mmol), methyl (1S,2R)-2-amino-1-ethylcyclopentanecarboxylate was obtained as a mixture of two components (1.103 g) after purification on silica gel, eluting with 2% ethyl acetate/hexanes.

Step 2

According to the procedure of Example 53, Step 2, using crude methyl (1S,2R)-2-{benzyl[(1R)-1-phenylethyl]amino}-1-ethylcyclopentanecarboxylate (1.103 g), 4.4% formic acid in methanol (30 mL) and 10% Pd/C (2 g), methyl (1S,2R)-2-amino-1-ethylcyclopentanecarboxylate (441 mg, 2.12 mmol, 21%) was obtained as a colorless solid. $^1$H NMR (400 MHz, DMSO-D6) δ ppm 0.78 (t, J=7.45 Hz, 3H) 1.42 (ddd, J=21.10, 7.58, 7.45 Hz, 1H) 1.50-1.78 (m, 5H) 1.92 (ddd, J=21.03, 7.42 Hz, 1H) 2.01-2.12 (m, 1H) 2.16-2.26 (m, 1H) 3.31 (s, 1H) 3.68 (s, 3H) 8.15 (s, 2H).

Step 3

According to the procedure of Example 53, Step 3, using methyl (1S,2R)-2-amino-1-ethylcyclopentanecarboxylate (410 mg, 1.97 mmol) and 4-(2-methyl-quinolin-4-yl-methoxy)-benzenesulfonyl chloride hydrochloride (917 mg, 2.39 mmol), methyl (1S,2R)-1-ethyl-2-[({4-[(2-methylquinolin-4-yl)methoxy]phenyl}sulfonyl)amino]cyclopentanecarboxylate (609 mg, 1.26 mmol, 64%) was obtained as a colorless solid after purification via column chromatography on silica gel, eluting with 30% ethyl acetate/hexanes. $^1$H NMR (400 MHz, CHLOROFORM-D) δ ppm 0.80-0.86 (m, 3H) 1.37-1.41 (m, 1H) 1.42-1.48 (m, 2H) 1.50-1.55 (m, 1H) 1.58-1.65 (m, 2H) 1.71-1.82 (m, 2H) 2.12 (ddd, J=12.76, 8.72, 3.54 Hz, 1H) 2.75-2.77 (m, 3H) 3.42 (td, J=9.79, 7.71 Hz, 1H) 3.69-3.71 (m, 3H) 5.57 (s, 2H) 5.64 (d, J=9.60 Hz, 1H) 7.09-7.13 (m, 2H) 7.43 (s, 1H) 7.56 (ddd, J=8.34, 7.07, 1.26 Hz, 1H) 7.74 (ddd, J=8.40, 7.01, 1.52 Hz, 1H) 7.83-7.92 (m, 3H) 8.10 (d, J=7.83 Hz, 1H).

Step 4

Methyl (1S,2R)-1-ethyl-2-[({4-[(2-methylquinolin-4-yl)methoxy]phenyl}sulfonyl)amino]cyclopentanecarboxylate (315 mg, 0.653 mmol) was combined with aqueous 5M sodium hydroxide solution (0.65 mL, 3.3 mmol) in THF, with MeOH added to homogenize the mixture. This solution was stirred at 50° C. for 5d, after which triethylamine hydrochloride (540 mg, 3.9 mmol) was added. The heterogeneous mixture was concentrated, and chased twice with methanol and twice with benzene to give (1S,2R)-1-ethyl-2-[({4-[(2-methylquinolin-4-yl)methoxy]phenyl}sulfonyl)amino]cyclopentanecarboxylic acid as a white solid that was carried on without further purification. The solid was combined with BOP (349 mg, 0.790 mmol), hydroxylamine hydrochloride (100 mg, 1.43 mmol) and triethylamine (0.45 mL) in DMF (3 mL) and heated at 50° C. overnight. Additional BOP (362 mg, 0.819 mmol), hydroxylamine hydrochloride (150 mg, 2.1 mmol) and Et$_3$N (0.3 mL) were then added and the reaction was stirred at 50° C. overnight. The reaction was still incomplete and more BOP (750 mg, 1.70 mmol), hydroxylamine hydrochloride (333 mg, 4.76 mol) and Et$_3$N (0.6 mL) were added. After 5 h the reaction mixture was diluted with brine and extracted three times with ethyl acetate. The combined organic extracts were dried over Na$_2$SO$_4$, concentrated, and purified via HPLC, eluting with a gradient of 15-100% MeCN/H$_2$O (10 min) to give (1S,2R)-N-hydroxy-1-ethyl-2-[({4-[(2-methylquinolin-4-yl)methoxy]phenyl}sulfonyl)amino]cyclopentanecarboxamide (162 mg, 0.331 mmol, 51%) as a colorless solid. LCMS (M−H): 1.81 min, 483.8; $^1$H NMR (400 MHz, ACETONITRILE-D3) δ ppm 0.67 (t, J=7.45 Hz, 3H) 1.08-1.20 (m, 2H) 1.31-1.42 (m, 2H) 1.49-1.60 (m, 3H) 1.82-1.87 (m, 2H) 2.56-2.58 (m, 3H) 3.19-3.28 (m, 1H) 5.49-5.52 (m, 2H) 6.23 (d, J=8.59 Hz, 1H) 7.08-7.13 (m, 2H) 7.42 (s, 1H) 7.48 (td, J=7.64, 1.39 Hz, 1H) 7.64 (ddd, J=8.40, 6.88, 1.39 Hz, 1H) 7.70-7.75 (m, 2H) 7.91 (m, 2H).

Step 1

To 204 mg (0.423 mmol) of methyl (1S,2R)-1-ethyl-2-[({4-[(2-methylquinolin-4-yl)methoxy]phenyl}sulfonyl)amino]cyclopentanecarboxylate (Example 56, Step 3) in THF (1.5 mL) was added 60% sodium hydride (22 mg, 0.55 mmol) and the resulting mixture was stirred at room temperature for 1 h. Iodomethane (35 μL, 80 mg 0.56 mmol) was added and the reaction was stirred overnight and then quenched with saturated aqueous ammonium chloride. These steps were repeated twice more, until starting material was consumed, and the residue was purified by column chromatography on silica gel eluting with 50% ethyl acetate/hexanes to give methyl (1S,2R)-1-ethyl-2-[methyl({4-[(2-methylquinolin-4-yl)methoxy]phenyl}sulfonyl)amino]cyclopentanecarboxylate (174 mg, 0.350 mmol, 83%) as a colorless solid. $^1$H NMR (400 MHz, CHLOROFORM-D) □ ppm 0.85 (t, J=7.33 Hz, 3H) 1.29-1.40 (m, 1H) 1.48-1.60 (m, 4H) 1.78-1.87 (m, 1H) 2.20-2.30 (m, J=7.01, 7.01, 7.01, 7.01 Hz, 2H) 2.57 (s, 3H) 2.75 (s, 3H) 3.71 (s, 3H) 5.55 (s, 2H) 7.11 (ddd, J=9.41, 2.78, 2.46 Hz, 2H) 7.42 (s, 1H) 7.55 (ddd, J=8.27, 6.88, 1.26 Hz, 1H) 7.70-7.76 (m, 3H) 7.90 (d, J=7.58 Hz, 1H) 8.09 (d, J=7.83 Hz, 1H).

Step 2

According to the procedure of Example 56, Step 4, methyl (1S,2R)-1-ethyl-2-[methyl({4-[(2-methylquinolin-4-yl)methoxy]phenyl}sulfonyl)amino]cyclopentanecarboxylate (147 mg, 0.296 mmol), 5M sodium hydroxide solution (0.30 mL), triethylamine hydrochloride (936.7 mg, 7 mmol) were heated in a microwave (100° C., 110 min) to provide crude (1S,2R)-1-ethyl -2-[methyl({4-[(2-methylquinolin-4-yl)methoxy]phenyl}sulfonyl)amino]cyclopentanecarboxylic acid. To this crude residue were added BOP (677 mg, 1.53 mmol), hydroxylamine hydrochloride (634 mg, 9.06 mmol), and triethylamine (2 mL) to provide (1S,2R)-N-hydroxy-1-ethyl-2-[methyl({4-[(2-methylquinolin-4-yl)methoxy]phenyl}sulfonyl)amino]cyclopentanecarboxamide (79.2 mg, 0.159 mmol, 54%) as a colorless solid after purification via HPLC, eluting with a gradient of 15-100% MeCN/H$_2$0 (10 min). LCMS (M−H): 2.53 min, 496.2; $^1$H NMR (400 MHz, ACETONITRILE-D3) δ ppm 0.79-0.85 (m, 3H) 1.13-1.24 (m, 1H) 1.36-1.47 (m, 4H) 1.61-1.73 (m, 1H) 2.12-2.20 (m, 1H) 2.48-2.51 (m, 3H) 2.64-2.66 (m, 3H) 3.89-3.96 (m, 1H) 5.59 (d, J=1.01 Hz, 2H) 7.17-7.22 (m, 2H) 7.50 (s, 1H) 7.55 (ddd, J=8.34, 6.95, 1.14 Hz, 1H) 7.69-7.75 (m, 3H) 7.95-8.03 (m, 2H) 9.21 (s, 1H).

Example 57

(1S,2R)-N-hydroxy-1-ethyl-2-[methyl({4-[(2-methylquinolin-4-yl)methoxy]phenyl}sulfonyl)amino]cyclopentanecarboxamide Example 58

(1S,2R)-N-hydroxy-1-(hydroxymethyl)-2-[methyl({4-[(2-methylquinolin-4-yl)methoxy]phenyl}sulfonyl)amino]cyclopentanecarboxamide

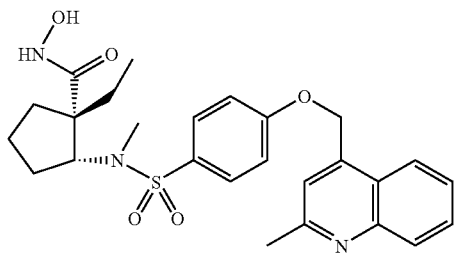

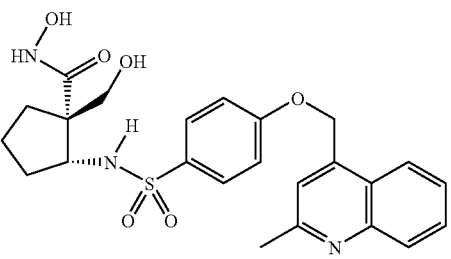

Step 1

According to the procedure of Example 53, Step 1, using (R)-N-benzyl-N-α-methylbenzylamine (4.2 mL, 4.24 g, 20 mmol), n-butyllithium (2.4 M, 7.4 mL), methyl 1-cyclopentene-1-carboxylate (1.3 mL, 1.29 g, 10.2 mmol), and formaldehyde (excess), methyl (1S,2R)-2-amino-1-(hydroxymethyl)cyclopentanecarboxylate was obtained (1.174 g) as a mixture of two components after chromatography on silica gel, eluting with 5% ethyl acetate/hexanes.

Step 2

According to the procedure of Example 53, Step 2, using crude methyl (1S,2R)-2-{benzyl[(1R)-1-phenylethyl]amino}-1-(hydroxymethyl)cyclopentanecarboxylate (800 mg), 4.4% formic acid in methanol (50 mL) and 10% Pd/C (421 mg), methyl (1S,2R)-2-amino-1-(hydroxymethyl)cyclopentanecarboxylate was obtained (404 mg, 1.93 mmol) as a colorless solid. $^1$H NMR (400 MHz, MeOD) δ ppm 1.76-1.82 (m, 2H) 1.84-1.92 (m, 1H) 2.09-2.18 (m, 1H) 2.20-2.30 (m, 1H) 3.58-3.68 (m, 2H) 3.81 (s, 3H) 3.97-4.02 (m, 1H).

Step 3

According to the procedure of Example 53, Step 3, using methyl (1S,2R)-2-amino-1-(hydroxymethyl) cyclopentanecarboxylate (304 mg, 1.4 mmol) and 4-(2-methyl-quinolin-4-ylmethoxy)-benzenesulfonyl chloride hydrochloride (1.033 g, 2.97 mmol), provided methyl (1S,2R)-1-(hydroxymethyl)-2-[({4-[(2-methylquinolin-4-yl)methoxy]phenyl}sulfonyl)amino]cyclopentanecarboxylate (238 mg, 35%) as a colorless solid after purification via HPLC, eluting with a gradient of 15-100% MeCN/H$_2$O (10 min). $^1$H NMR (400 MHz, CHLOROFORM-D) δ ppm 1.46-1.58 (m, 1H) 1.63-1.69 (m, 2H) 1.71-1.77 (m, 2H) 1.91-2.01 (m, 1H) 2.77 (s, 3H) 3.55-3.65 (m, 1H) 3.68-3.72 (m, 1H) 3.73-3.75 (m, 3H) 3.78-3.83 (m, 1H) 5.44 (d, J=10.11 Hz, 1H) 5.58 (s, 2H) 7.11-7.15 (m, 2H) 7.44 (s, 1H) 7.57 (td, J=7.64, 1.14 Hz, 1H) 7.75 (ddd, J=8.46, 6.95, 1.26 Hz, 1H) 7.85 (ddd, J=9.41, 2.91, 2.59 Hz, 2H) 7.92 (d, J=7.58 Hz, 1H) 8.12 (d, J=8.34 Hz, 1H).

Step 4

According to the procedure of Example 56, Step 4, methyl (1S,2R)-1-(hydroxymethyl) -2-[methyl({4-[(2-methylquinolin-4-yl)methoxy]phenyl}sulfonyl)amino]cyclopentanecarboxylate (213 mg, 0.439 mmol), 5M sodium hydroxide solution (0.44 mL), and triethylamine hydrochloride (365 mg, 2.63 mmol) provided methyl (1S,2R)-1-(hydroxymethyl)-2-[methyl({4-[(2-methylquinolin -4-yl)methoxy]phenyl}sulfonyl)amino]cyclopentanecarboxylic acid. To the acid was added BOP (867 mg, 1.96 mmol), hydroxylamine hydrochloride (649 mg, 9.27 mmol), and triethylamine (2.1 mL) to give (1S,2R)-N-hydroxy-1-(hydroxymethyl) -2-[methyl({4-[(2-methylquinolin-4-yl)methoxy]phenyl}sulfonyl)amino]cyclopentanecarboxamide (86.7 mg, 41%) as a colorless solid after purification via HPLC, eluting with a gradient of 15-100% MeCN/H$_2$O (10 min). LCMS (M–H): 1.57 min, 484.3; $^1$H NMR (400 MHz, MeOD) δ ppm 1.44-1.49 (m, 1H) 1.56-1.62 (m, 2H) 1.64-1.68 (m, 1H) 2.02-2.12 (m, 1H) 2.67 (s, 3H) 3.43-3.53 (m, 2H) 3.67 (d, J=11.37 Hz, 1H) 5.58 (s, 2H) 7.21 (d, J=9.09 Hz, 2H) 7.50 (s, 1H) 7.56 (t, J=7.71 Hz, 1H) 7.69-7.75 (m, 1H) 7.84 (d, J=8.84 Hz, 2H) 7.96 (d, J=8.59 Hz, 1H) 8.01 (d, J=8.34 Hz, 1H).

Example 59

(3R,4R)-N,3-dihydroxy-4-[({4-[(2-methylquinolin-4-yl)methoxy]phenyl}sulfonyl)amino]piperidine-3-carboxamide

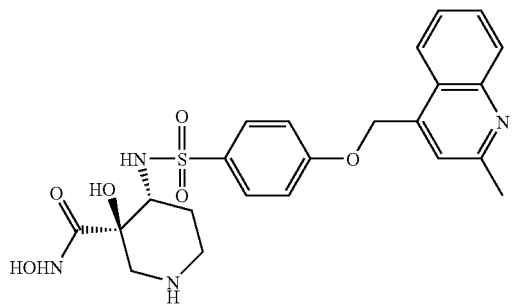

(3R,4R)-N-tert-Butoxy-3-hydroxy-4-(4-((2-methylquinolin-4-yl) methoxy)phenylsulfonamido)piperidine-3-carboxamide trifluoroacetic acid salt (Example 46, Step 8) was treated with neat trifluoroacetic acid (3 mL) at 45° C. for 5 days. After removal of trifluoroacetic acid, the residue was purified using preparative HPLC, eluting with a gradient of 10-30% acetonitrile with triethylamine (10 min) to yield 17.2 mg (22%) of (3R,4R)-N,3-dihydroxy-4-[({4-[(2-methylquinolin-4-yl)methoxy]phenyl}sulfonyl)amino]piperidine-3-carboxamide as white powder. HRMS: calcd for C$_{23}$H$_{26}$N$_4$O$_6$S+H+, 487.16458; found (ESI-FTMS, [M+H]$^{1+}$), 487.1646

Example 60

(1S,2R)-N-hydroxy-2-methyl-2-[({4-[(2-methylquinolin-4-yl)methoxy]phenyl}sulfonyl)amino]cyclohexanecarboxamide (racemic)

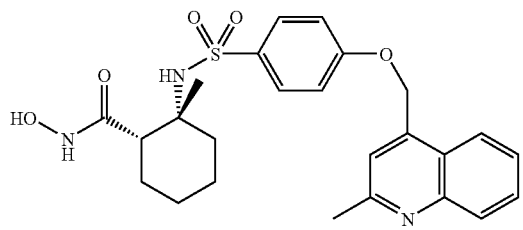

Step 1

Following the procedure of Spurr et al, *J. Am. Chem. Soc.*, 1983, 105, 4735, a solution of 1-methyl-1-cyclohexene (1 g, 10.4 mmol) in dichloromethane (30 mL) was cooled to −20° C. and chlorosulfonylisocyanate (1.08 mL, 12.5 mmol) was added drop wise. The reaction was warmed to −10° C. over 3 h, then warmed to room temperature and stirred for 1 h. The reaction mixture was then concentrated, and taken up in ether (15 mL) and dimethylethyleneglycol (5 mL) to homogenize. To the reaction mixture was added 25% Na$_2$SO$_3$ (25 mL), followed by 10% sodium hydroxide solution to keep the pH between 7-8. The reaction was stirred overnight, taken up in ethyl acetate, washed with brine, dried over MgSO$_4$, filtered and concentrated to afford racemic (1S,6R)-6-methyl-7-azabicyclo[4.2.0]octan-8-one (0.95 g, 66%). MS: 140.1 (M+H)+

Step 2

To a solution of racemic (1S,6R)-6-methyl-7-azabicyclo [4.2.0]octan-8-one (0.46 g, 3.3 mmol) in methanol (9 mL) at 0° C. was added trimethylsilylchloride (0.84 g, 2 eq). The reaction was stirred at room temperature overnight, concentrated and chased with methanol/benzene to afford the crude amino ester. To a solution of the crude amino ester in dichloromethane (10 mL) was added 4-(2-methyl-quinolin-4-yl-methoxy)-benzenesulfonyl chloride hydrochloride (1.5 g, 1.2 eq) followed by saturated sodium bicarbonate and ethyl acetate (2 mL). The reaction was stirred overnight and the methylene chloride was removed in vacuo. The mixture was then extracted with ethyl acetate, washed with brine, dried over MgSO$_4$, filtered and concentrated. Chromatography on silica gel eluting with a gradient of 40-60% ethyl acetate/hexanes afforded racemic methyl (1S,2R)-2-methyl-2-[({4-[(2-methylquinolin-4-yl)methoxy]phenyl}sulfonyl)amino] cyclohexanecarboxylate (0.375 g, 23% over two steps). MS: 483.1 (M+H)+

Step 3

To a solution of racemic methyl (1S,2R)-2-methyl-2-[({4-[(2-methylquinolin-4-yl)methoxy]phenyl}sulfonyl)amino] cyclohexanecarboxylate (0.3 g, 0.62 mmol) in THF (3 mL) was added sodium hydroxide solution (5N, 0.62 mL) followed by methanol (2 mL) to homogenize. The reaction was stirred overnight and concentrated. The addition of water resulted in a precipitate which was centrifuged, filtered and washed to afford racemic (1S,2R)-2-methyl-2-[({4-[(2-methylquinolin-4-yl)methoxy]phenyl}sulfonyl)amino]cyclohexanecarboxylate (0.08 g, 27%). MS: 469.1 (M+H)+

Step 4

To a solution of racemic (1S,2R)-2-methyl-2-[({4-[(2-methylquinolin-4-yl)methoxy]phenyl}sulfonyl)amino]cyclohexanecarboxylate (0.075 g) in DMF (0.8 mL) was added BOP (0.1 g, 1.3 eq), diisopropylethylamine (0.122 mL, 4 eq) and hydroxylamine hydrochloride (0.024 g, 2 eq). The reaction was stirred for 8 h and purified by direct injection onto an HPLC to afford racemic (1S,2R)-N-hydroxy-2-methyl-2-[({4-[(2-methylquinolin-4-yl)methoxy]phenyl}sulfonyl) amino]cyclohexanecarboxamide (0.03 g, 40%) as a white powder. MS: 484.1 (M+H)+

Example 61 trans-N-hydroxy-2-[methyl({4-[(2-methylquinolin-4-yl)methoxy]phenyl}sulfonyl)amino]cyclohexanecarboxamide Step 1

According to the procedure of Example 10, Step 1, the reaction of 487 mg (3.4 mmol) of trans-2-amino-1-cyclohexanecarboxylic acid with 1.31 g of 4-(2-methyl-quinolin-4-ylmethoxy)-benzenesulfonyl chloride hydrochloride provided 382.7 mg of trans-2-[({4-[(2-methylquinolin-4-yl) methoxy]phenyl}sulfonyl)amino]cyclohexanecarboxylic acid in 25% yield. MS: 455.1 (M+H)+

Step 2

To the solution of 374 mg of trans-2-[({4-[(2-methylquinolin-4-yl)methoxy]phenyl}sulfonyl)amino]cyclohexanecarboxylic acid in 3 mL of toluene was added 0.88 mL of N,N-dimethylformamide di-tert-butyl acetal. The solution was refluxed for 4 hr. After removal of the volatile material in vacuo, 131 mg of tert-butyl trans-2-[({4-[(2-methylquinolin-4-yl)methoxy]phenyl}sulfonyl)amino]cyclohexanecarboxylate was obtained in 33% yield after flash column chromatography. MS: 511.2 (M+H)+

Step 3

To the stirred solution of 125 mg of tert-butyl trans-2-[({4-[(2-methylquinolin-4-yl)methoxy]phenyl}sulfonyl)amino] cyclohexanecarboxylate in 4 mL of N,N-dimethylformamide was added 133 mg of potassium carbonate, followed by 68 mg of iodomethane. The suspension was stirred at room temperature over night. After removal of the volatile material in vacuo, 80 ml of ethyl acetate was added. The organic phase was washed with water and saturated sodium chloride solution, dried over magnesium sulfate, filtered and concentrated. The residue was to provide 121 mg (97% yield) of tert-butyl trans-2-[methyl({4-[(2-methylquinolin-4-yl)methoxy] phenyl}sulfonyl)amino]cyclohexanecarboxylate after flash column chromatography eluting with ethyl acetate/hexane (3:7). MS: 525.2 (M+H)+

Step 4

To the stirred solution of 112 mg of tert-butyl trans-2-[methyl({4-[(2-methylquinolin-4-yl)methoxy] phenyl}sulfonyl)amino]cyclohexanecarboxylate in 8 mL of dichloromethane was added 3 ml of trifluoroacetic acid slowly. The solution was stirred at room temperature for 2 hr. After removal of the volatile material trans-2-[methyl({4-[(2-methylquinolin-4-yl)methoxy]phenyl}sulfonyl)amino]cy-clohex-anecarboxylic acid was obtained in quantitative yield. MS: 469.1 (M+H)+

Step 5

According to the procedure of Example 10, Step 2, the reaction of 111 mg of trans-2-[methyl({4-[(2-methylquinolin-4-yl)methoxy]phenyl}sulfonyl)amino]cyclohex-anecarboxylic acid with hydroxylamine provided 71 mg of trans-N-hydroxy-2-[methyl({4-[(2-methylquinolin-4-yl)methoxy] phenyl}sulfonyl)amino]cyclohexanecarboxamide in 77% yield. MS: 484.1 (M+H)+

Determination of Activity

Standard pharmacological test procedures are readily available to determine the ability of compounds of the invention to inhibit TACE. Generally, TACE inhibition is determined by the ability to inhibit TACE mediated cleavage of a TNF-α precursor (pro-TNF protein), or a TACE substrate (such as pro-TNF peptide) which contains the same scissile amide bond as that of the TNF-α precursor. The inhibition is generally reported as the percentage of inhibition of the cleavage of the TNF-α precursor (or a TACE substrate), or as the IC50 (the concentration required for 50% inhibition). Some exemplary standard pharmacological test procedures for TACE inhibition are provided in (a) Jin, G., Huang, X., Black,

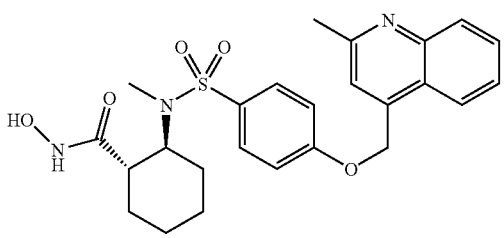

R., Wolfson, M., Rauch, C., McGregor, Ellestad, G., and Cowling, R. (2002) A Continuous Fluorimetric Assay for Tumor Necrosis Factor-α Converting Enzyme. Analytical Biochemistry 302, 269-275; (b) Newton, R C, Solomon, K A, Covington, M B, Decicco, C P, Haley, P J, Friedman, S M, Vaddi, K. (2001); Biology of TACE inhibition. Ann Rheum Dis. 60: iii25-iii32; and (c) Knight, C. G., Willenbrock, F., and Murphy, G. *FEBS Lett*. (1992) 296, 263-266, each of which is hereby incorporated by reference in its entirety.

Biological Assays of Compounds of the Invention

TACE FRET Assay using TACE Cat

The procedure is essentially as described in Jin, G. et al., Analytical Biochemistry (2002) 302, 269-275, incorporated by reference herein in its entirety. The basic measurement of the assay is the percentage of inhibition of the cleavage of the fluorogenic pro-TNF peptide by TACE or the IC50 determination by a filting with the model-39 of LSW data analysis tool, which processes data according to the equation $y=((B*K^n)+(100*x^n))/(K^n+x^n)$, a sigmoidal curve with Hill slope, B to 100. K is the IC50. Generally, n and B are floated, noting that n (hill slope) should be close to 1 and B (background offset) to 0.

Pro-TNF-α substrate peptide Abz-LAQAVRSSSR-Dpa (AnaSpec, San Jose, Calif., WARC-1) was prepared as a 2 mM stock solution in the TACE assay buffer (50 mM Tris-HCI, pH 7.4, 25 mM NaCl, 4% Glycerol, 0.005% Brij 35). The catalytic domain of the recombinant TACE protein was expressed and purified. The TACE protein (1 ug/ml) was pretreated with the inhibitors at various concentrations for 10 min at room temperature. The reaction was initiated by the addition of the substrate peptide. The increase in fluorescence was monitored at an Excitation of 320 nM and an Emission of 420 nM over a period of 10 min. The initial rate (slope) of the reaction was determined using a fluorescence plate reader (Molecular Devices, Spectra Max Gemini XS).

Results of $IC_{50}$ determinations in the TACE FRET assay for representative compounds of the invention are shown in Table 1.

In-Vitro Fluorescence Assay of MMP-1 Activity

A continuous assay was used in which the substrate is a synthetic peptide containing a fluorescent group (7-methoxycoumarin; Mca) that is quenched by energy transfer to a 2,4-dinitrophenyl group. See Knight, C. G. et al., FEBS Lett. (1992) 296, 263-266. When the peptide was cleaved by MMP, a large increase in fluorescence was observed. The source of enzyme in the assay was the recombinant human catalytic domain of MMP-1. See Zhang, Y et al., The Journal of Pharmacology and Experimental Therapeutics (JPET), 309:348-355, 2004. The substrate used was Mca-PQGL-(3-[2,4-dinitrophenyl]-L-2,3-diaminopropionyl)-AR-OH (denoted as Wammp-5, custom synthesized by AnaSpec, Inc.). The assay buffer consisted of 50 mM Hepes (pH 7.4), 100 mM NaCl, 5 mM $CaCl_2$, and 0.005% Brij-35. Each well of black polystyrene 96-well plates contained a 200 µL reaction mixture consisting of assay buffer, purified MMP (final concentration of 25 ng/ml, prepared by diluting with the assay buffer), and varied concentrations of inhibitor (prepared by serially diluting a given inhibitor in DMSO in 96-well polypropylene plate). The plates were then incubated at 30° C. for 15 minutes. The enzymatic reactions were initiated by adding the substrate to a final concentration of 20 µM, and mixing 10 times with a pipette. The final DMSO concentration in the assay was 6.0%. The initial rate of the cleavage reaction was determined at 30° C. temperature with a fluorescence plate reader (excitation filter of 330 nm and emission filter of 395 nm) immediately after substrate addition.

Plots of the inhibitor concentration vs. the percent inhibition were fit to the following equation: $y=(a-d)/[1+(x/c)^b]+d$, a general sigmoidal curve with Hill slope, a to d. x is the inhibitor concentration under test. y is the percent inhibition. a is the limiting response as x approaches zero. As x increases without bound, y tends toward its limit d. c is the inflection point (IC50) for the curve. That is, y is halfway between the lower and upper asymptotes when x=c. b is the slope factor or Hill coefficient. See Knight, C. G., Willenbrock, F., and Murphy, G. *FEBS Lett*. (1992) 296, 263-266, incorporated herein by reference in its entirety.

Results for representative compounds of the invention are shown in Table 1.

In-vitro Fluorescence Assay of MMP-2 Activity

The method was essentially the same as for the determination of MMP-1 activity, described above, except that the source of enzyme in the assay was the recombinant human MMP-2 (66 kDa) purchased from Oncogene Research Products (catalog number PF023 from Calbiochem).

Results for representative compounds of the invention are shown in Table 1.

In-vitro Fluorescence Assay of MMP-7 Activity

The method was similar to that for the determination of MMP-1 activity, described above, with the following differences. Active, recombinant human MMP-7 was purchased from Calbiochem (catalog #444270; expressed in *E. coli*, 19 kDa). The substrate used was Mca-PLGL-(3-[2,4-dinitrophenyl]-L-2,3-diaminopropionyl)-AR—$NH_2$ (purchased from Bachem or AnaSpec, Inc.; first described by Knight, C. G., Willenbrock, F., and Murphy, G. *FEBS Lett*. (1992) 296, 263-266). The concentration of the substrate stock was spectrophotometrically determined using the extinction coefficient at 410 nm of 7500 $M^{-1}$ $cm^{-1}$. The assay buffer (pH 7.4) consisted of 50 mM Hepes, 100 mM NaCl, 5 mM $CaCl_2$, and 0.005% Brij-35. Each well of black polystyrene 96-well plates contained a reaction consisting of assay buffer, purified MMP (final concentration of 1.0 nM, prepared by dilution with assay buffer), and varied concentrations of inhibitor (prepared by serial dilution in DMSO in 96-well polypropylene plates). The plates were then incubated at room temperature for 30 minutes. The enzymatic reactions were initiated by adding substrate to a final concentration of 15 µM and were mixed by pipetting up and down. The final DMSO concentration in the assay was 10% and the final, total assay volume was 200 µl. The initial rate of the cleavage reaction was determined at room temperature with a fluorescence plate reader (excitation at 325 nm with a 12 nm bandwidth and emission at 395 nm with a 12 nm bandwidth) immediately after substrate addition. Plots of the inhibitor concentration vs. the initial cleavage rate were fit to the following equation in order to determine $IC_{50}$ values: $y=V_{max}*(1-(x^n/(K^n+x^n)))$, whereby x=inhibitor concentration, y=initial rate, $V_{max}$=initial rate in the absence of inhibitor, n=slope factor, and K=$IC_{50}$ for the inhibition curve.

Results for representative compounds of the invention are shown in Table 1.

In-vitro Fluorescence Assay of MMP-8 Activity

The method was similar to that for the determination of MMP-1 activity, described above, with the following differences. The source of enzyme in the assay was the recombinant human MMP-8 (51 kDa) purchased from R&D Systems (catalog number 908-MP-010). The substrate used was Mca-PLGL-(3-[2,4-dinitrophenyl]-L-2,3-diaminopropionyl)-

AR-NH$_2$ purchased from AnaSpec (cat.# 27077) or Bachem (cat.# M-1895). The Km of MMP-8 for this substrate is 21 μM under these conditions. The enzyme was activated by incubation with 1 mM APMA (p-aminophenylmercuric acetate, Sigma cat.# A9563). Activation was carried out by diluting a stock solution of 30 mM APMA in DMSO by 1:30 into a solution of 50 μg/ml (1 μM) enzyme in assay buffer and incubating for 1 hour at 37° C. The assay buffer consisted of 50 mM Hepes (pH 7.4), 100 mM NaCl, 5 mM CaCl$_2$, and 0.005% Brij-35. Each well of black polystyrene 96-well plates contained a 200 μL reaction mixture consisting of assay buffer, activated MMP-8 (final concentration of 2.5 nM, prepared by diluting with the assay buffer), and varied concentrations of inhibitor (prepared by serially diluting a given inhibitor in DMSO in a 96-well polypropylene plate). The plates were then incubated at 25° C. for 15 minutes. The enzymatic reactions were initiated by adding the substrate to a final concentration of 20 μM, and mixed by pipelting up and down. The final DMSO concentration in the assay was 5.0%. The initial rate of the cleavage reaction was determined at 25° C. with a fluorescence plate reader (excitation filter of 320 nm and emission filter of 405 nm) immediately after substrate addition.

Plots of the inhibitor concentration vs. the percent inhibition were fit to the following equation: y=((B* K")+(100* x"))/(K"+x"), a general sigmoidal curve with Hill slope, B to 100. x is the inhibitor concentration under test. y is the percent inhibition As x increases without bound, y tends toward 100. K is the inflection point (IC50) for the curve. That is, x is halfway between the lower and upper asymptotes when x=K. n is the slope factor. B is the Hill coefficient. Percent inhibition is defined by the equation: % inhibition=100*(Vo−Vi)/Vo where Vo is the reaction rate in the absence of inhibitor and Vi is the reaction rate in the presence of a given concentration of inhibitor.

Results for representative compounds of the invention are shown in Table 1.

In-vitro Fluorescence Assay of MMP-9 Activity

The method was essentially the same as for the determination of MMP-7 activity, described above, except that the source of enzyme in the assay was recombinant human MMP-9 (83 kDa) was purchased from Calbiochem (catalog #PF024), the final enzyme concentration was 0.5-1.0 nM, and the final substrate concentration was 20 μM.

Results for representative compounds of the invention are shown in Table 1.

In-vitro Fluorescence Assay of MMP-13 Activity

The method was essentially the same as for the determination of MMP-1 activity, described above, except that the final concentration of purified MMP in the assay was 0.5 nM, prepared by diluting with the assay buffer.

Results for representative compounds of the invention are shown in Table 1.

In-vitro Fluorescence Assay of MMP-14 Activity

The method was essentially the same as for the determination MMP-13 activity, described above, except that the source of enzyme in the assay was the recombinant human catalytic domain of MMP-14 (177 amino acids corresponding to Tyr89-Gly265 of mature human enzyme; 20 kDa) purchased from Chemicon International, Inc. (catalog number CC1041), and that each well of black polystyrene 96-well plates contained a 200 μL reaction mixture consisting of assay buffer, MMP (final concentration of 25 ng/ml, prepared by diluting with the assay buffer), and varied concentrations of inhibitor (prepared by serially diluting a given inhibitor in DMSO in 96-well polypropylene plate).

The results were analyzed as described for MMP-13 activity, above.

Results for representative compounds of the invention are shown in Table 1.

TABLE 1

| | [IC$_{50}$ (nM)] | | | | | | | |
|---|---|---|---|---|---|---|---|---|
| | TACE | MMP-1 | MMP-2 | MMP-7 | MMP-8 | MMP-9 | MMP-13 | MMP-14 |
| 1* | 2 | | 6183 | | | | | >16667 |
| 1a** | 1.3 | >16667 | 4575 | | | | >16667 | >16667 |
| 1b*** | 43 | >16667 | >16667 | | | | >16667 | >16667 |
| 2 | 2.2 | | >16667 | | | | >16667 | |
| 3 | 1.1 | >16667 | 4118 | | | | 3306 | >16667 |
| 4 | <0.6 | >16667 | >16667 | | | | 6383 | >16667 |
| 5 | 1.1 | | >16667 | | | | >16667 | |
| 6 | 1 | | >16667 | | | | >16667 | |
| 7 | 1.2 | | >16667 | | | | >16667 | |
| 8 | 1.5 | | >16667 | | | | >16667 | |
| 9 | 0.1 | | >16667 | | | | >16667 | |
| 10 | 1.1 | | >16667 | | | | >16667 | |
| 11 | 0.6 | | >16667 | | | | >16667 | |
| 12 | 1 | | >16667 | | | | >16667 | |
| 13 | <0.6 | >16667 | >10000 | 444 | >16667 | >16667 | >10000 | >16667 |
| 14 | 1.8 | | >16667 | | | | >16667 | |
| 15 | 2.6 | | >16667 | | | | >16667 | |
| 16 | <0.6 | | 9743 | | | | 13659 | |
| 17 | 0.6 | >16667 | >10000 | 668 | >16667 | >16667 | >10000 | >16667 |
| 18 | 0.7 | | >10000 | | | | >10000 | |
| 19 | <0.6 | | >10000 | | | | 10000 | |
| 20 | 1.1 | >16667 | >10000 | 812 | >16667 | >16667 | 10190 | >16667 |
| 21 | <0.6 | | 8802 | | | | 4886 | |
| 22 | 4.7 | | >16667 | | | | >16667 | |
| 23 | 1.3 | >16667 | >16667 | 1171 | >16667 | >16667 | >16667 | >16667 |
| 24 | 0.8 | | >16667 | | | | >16667 | |
| 25 | 7.9 | | >16667 | | | | >16667 | |
| 26 | 0.6 | >16667 | >16667 | 827 | >16667 | >16667 | >16667 | >16667 |
| 27 | 1.4 | | >16667 | | | | >16667 | |

TABLE 1-continued

| | [IC$_{50}$ (nM)] | | | | | | | |
|---|---|---|---|---|---|---|---|---|
| | TACE | MMP-1 | MMP-2 | MMP-7 | MMP-8 | MMP-9 | MMP-13 | MMP-14 |
| 28 | 0.5 | | >16667 | | | | 14402 | |
| 29 | 0.8 | | >16667 | | | | 13241 | |
| 30 | <0.6 | | >10000 | | | | 9091 | |
| 31 | 0.9 | | >10000 | | | | 6634 | |
| 32 | 3.2 | | >10000 | | | | >10000 | |
| 33 | 0.7 | | >16667 | | | | >16667 | |
| 34 | 1 | >16667 | >16667 | | | | >16667 | |
| 35 | 1.4 | >16667 | >16667 | 4617 | >16667 | >16667 | >16667 | >16667 |
| 36 | 1.3 | >16667 | >16667 | | | | >16667 | |
| 37 | 10 | | >16667 | | | | >16667 | |
| 38 | 51 | | 8680 | | | | >16667 | |
| 39 | 172 | | | | | | | |
| 40 | 56 | | | | | | | |
| 41 | | | | | | | | |
| 42 | | | | | | | | |
| 43 | | | | | | | | |
| 44 | 0.5 | | >16667 | | | | >16667 | |
| 45 | 6.2 | | >16667 | | | | >16667 | |
| 46 | 1.4 | | >16667 | | | | >16667 | |
| 47 | 6.4 | | >16667 | | | | >16667 | |
| 48 | 211 | | >16667 | | | | >16667 | |
| 49 | 19 | | >16667 | | | | >16667 | |
| 50 | 3.7 | | >16667 | | | | >16667 | |
| 51 | <0.6 | | >16667 | | | | >10000 | |
| 52 | 2.4 | | >16667 | | | | >10000 | |
| 53 | 0.4 | | >16667 | | | | >16667 | |
| 54 | <0.6 | | >16667 | | | | >10000 | |
| 55 | <0.6 | | >16667 | | | | >16667 | |
| 56 | 2.3 | | >10000 | | | | >10000 | |
| 57 | 9.6 | | >10000 | | | | >10000 | |
| 58 | <0.6 | | >10000 | | | | >10000 | |
| 59 | 109 | | >10000 | | | | >10000 | |
| 60 | <0.6 | | >16667 | | | | >16667 | |
| 61 | 1.4 | | >16667 | | | | >16667 | |

*Racemate of Example 1, supra.
**Enantiomer 1 of Example 1, supra.
***Enantiomer 2 of Example 1, supra.

Human Whole Blood Assay for LPS-induced TNF-α Secretion procedure is essentially as described in Newton, R. C., et al., (2001) Ann Rheum Dis. 60, iii25-iii32, incorporated by reference herein in its entirety. The basic measurement of the assay is the percentage of inhibition of TNF-α secretion and the IC$_{50}$ determination by a filting with the model-39 of LSW data analysis tool.

350 μl of fresh human blood drawn from healthy volunteers were pre-incubated with compounds for one hour at the various concentrations at 37° C. with turning generally, the final DMSO concentrations should be kept below 0.2%. At the end of cubation, LPS (Sigma, L2262) was added to the blood at 100 ng/ml and the samples were further incubated for 4 hours or overnight at 37° C. with constant rotation. At the end of the incubation period, 650 μl of serum-free medium was added to the blood samples and the samples were centrifuged at 1500 rpm for 15 minutes. 500 μl of supernate was collected and frozen at −80° C.

The TNF-α and other proinflammatory cytokines were detected by ELISA assay according to the manufacturer's instruction (Biosource International, Inc., Camarillo, Calif.). Results for representative compounds of the invention are shown in Table 2.

Cell-based Assay for Inhibition of TNF-α Secretion in Raw Cells

The basic measurement of the assay is the percentage of inhibition of TNF-α secretion and the IC$_{50}$ determination by a fitting with the model-39 of LSW data analysis tool.

Raw 264.7 cells (ATCC Cat No. TIB-71) are maintained in DMEM medium containing 10% of serum P/S, and Glutamine. Cells are split twice a week by scraping and 1 to 10 or 20 dilutions. For testing compounds, cells are cultured to confluence and are seeded the day before the experiment in 24 well culture dishes at 0.5 to 1 million/ml well. On the next morning, the medium from the overnight culture is replaced with the fresh growth medium. The compounds are added at various concentration at the 0.2% of final DMSO concentrations (10 μl of a 20% DMSO solution containing testing compounds is added to each well). The cells are pre-incubated with compounds for 1 hr. LPS (Sigma, L2262) is added to cells at a final concentration of 100 ng/ml (10 μl of a 10 μM LPS solution freshly diluted from a 1 mg/ml LPS stock solution in PBS is added to each well) and cells are further incubated for 4 hr at 37° C. 1 ml of the supernatant was collected, cells are spun down and the supernatants are frozen at −80° C. until use.

The TNF-α and other proinflammatory cytokines were detected by an ELISA assay according to the manufacturer's instructions (Biosource International, Inc., Camarillo, Calif. (For IL-1b measurement in Raw cells, one round of freeze and thaw of the cells was required).

Results for representative compounds of the invention are shown in Table 2

TABLE 2

| Example | TNF Secretion Raw Cells IC50 (uM) | TNF Secretion HWB IC50 (uM) |
|---|---|---|
| 1* | 0.018 | 3 |
| 1a** | | 2.8 |
| 1b*** | 0.25 | 14 |
| 2 | | 9.9 |
| 3 | 0.01 | 2.2 |
| 4 | 0.018 | 1.6 |
| 5 | 0.052 | 9.6 |
| 6 | | 47 |
| 7 | | 34 |
| 8 | | >50 |
| 9 | | 9.3 |
| 10 | | 4.2 |
| 11 | 0.011 | 0.74 |
| 12 | 0.08 | 2.2 |
| 13 | 0.009 | 0.25 |
| 14 | 0.06 | 4.5 |
| 15 | >1.0 | >50 |
| 16 | 0.093 | 4.78 |
| 17 | 0.024 | 0.34 |
| 18 | 0.09 | 1 |
| 19 | 0.02 | 0.2 |
| 20 | 0.02 | 0.12 |
| 21 | 0.038 | 1.3 |
| 22 | 0.09 | 0.27 |
| 23 | 0.051 | 0.28 |
| 24 | 0.017 | 0.23 |
| 25 | >1.0 | >50 |
| 26 | 0.012 | 0.2 |
| 27 | 0.929 | 41 |
| 28 | 0.46 | 0.8 |
| 29 | 0.007 | 0.086 |
| 30 | 0.03 | 0.25 |
| 31 | 0.02 | 0.05 |
| 32 | 0.18 | 1.9 |
| 33 | 0.058 | 4.7 |
| 34 | 0.021 | 0.5 |
| 35 | 0.058 | 0.8 |
| 36 | 0.202 | 1 |
| 37 | | 59 |
| 38 | | 26 |
| 39 | | |
| 40 | | |
| 41 | | |
| 42 | | |
| 43 | | |
| 44 | 1.674 | 46 |
| 45 | 1.923 | >50 |
| 46 | 0.16 | 2.9 |
| 47 | >1.0 | >50 |
| 48 | >1.0 | >50 |
| 49 | >1.0 | >50 |
| 50 | >1.0 | 22 |
| 51 | >1.0 | 30 |
| 52 | 0.762 | 37 |
| 53 | 0.082 | 3.6 |
| 54 | 0.019 | 2.3 |
| 55 | 0.27 | 5.9 |
| 56 | >1.0 | 48 |
| 57 | >1.0 | >50 |
| 58 | 0.44 | 14 |
| 59 | >1.0 | 49 |
| 60 | 0.025 | 4.9 |
| 61 | 0.911 | 43 |

*Racemate of Example 1, supra.
**Enantiomer 1 of Example 1, supra.
***Enantiomer 2 of Example 1, supra.

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the Formula I:

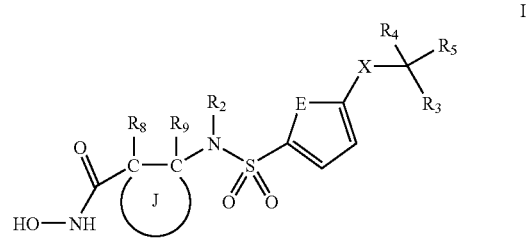

or and an entiomer or diastereomer or a pharmaceutically acceptable salt thereof, wherein:

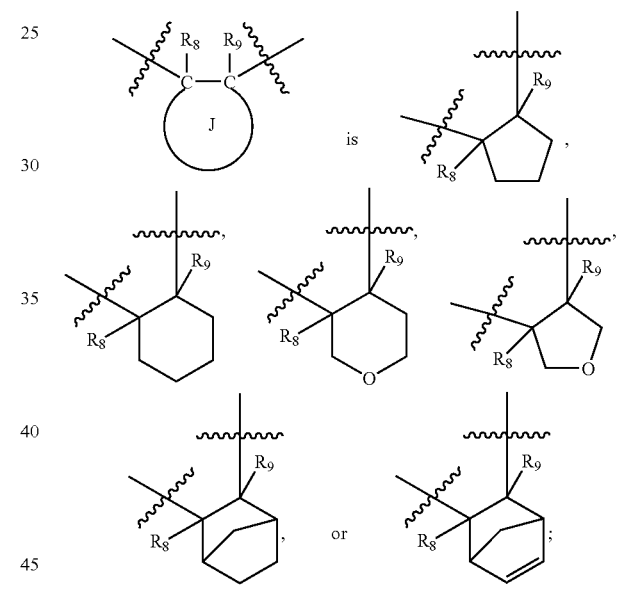

$R_2$ is hydrogen, $C_1$-$C_6$ alkyl, $C_2$-$C_6$ alkenyl or $C_2$-$C_6$ alkynyl;
  wherein each of said $C_1$-$C_6$ alkyl, $C_2$-$C_6$ alkenyl or $C_2$-$C_6$ alkynyl optionally is substituted with up to four independently selected $R_{14}$ groups;
$R_3$ is 2-methylquinolin-4-yl, 1-H-1,2,3-benzotriazol-1-yl, 1-H-benzimidazol-5-yl, or 2,1,3-benzoxadiazol-5-yl; each optionally substituted with up to four independently selected $R_{14}$ groups;
$R_4$ and $R_5$ are each independently hydrogen, $C_1$-$C_6$ alkyl, $C_2$-$C_6$ alkenyl, or $C_2$-$C_6$ alkynyl;
  wherein each of said $C_1$-$C_6$ alkyl, $C_2$-$C_6$ alkenyl, or $C_2$-$C_6$ alkynyl is optionally substituted with up to four independently selected $R_{15}$ groups;
$R_8$ and $R_9$ are each independently hydrogen, OH, $OR_{17}$, —$OCOR_{12}$, —OC(O)$NR_{12}R_{13}$, —$NR_{12}R_{13}$, —N($R_{12}$)$COR_{13}$, —N($R_{20}$)$COOR_{12a}$, —N($R_{20}$)$SO_2R_{13a}$, —N($R_{20}$)$CONR_{12}R_{13}$, halogen, $C_1$-$C_6$ alkyl, $C_2$-$C_6$ alkenyl, $C_2$-$C_6$ alkynyl, $C_3$-$C_8$ cycloalkyl, phenyl, naphthyl;

wherein each of said $C_1$-$C_6$ alkyl, $C_2$-$C_6$ alkenyl, $C_2$-$C_6$ alkynyl, $C_1$-$C_6$ alkoxy, $C_3$-$C_8$ cycloalkyl, phenyl, or naphthyl is optionally substituted with up to four independently selected $R_{16}$ groups;

each $R_{14}$, $R_{15}$ and $R_{16}$ is independently halogen, $NO_2$, CN, $C_{1-6}$ alkyl, $C_{2-6}$ alkenyl, $C_{2-6}$alkynyl, $C_{3-8}$cycloalkyl, —$OR_{17}$, $COR_{12}$, —$OCOR_{12}$, $C_{1-6}$ haloalkyl, $C_{1-6}$ perhaloalkyl, $CONR_{12}R_{13}$, —$S(O)_nR_{13a}$ —$OPO(OR_{12a})OR_{12a}$, —$PO(OR_{12a})R_{13}$, —$OC(O)OR_{12a}$, —O—$C_{1-6}$ alkyl-$NR_{12}R_{13}$, —$OC(O)NR_{12}R_{13}$, —$C(O)NR_{12}OR_{12a}$, —$COOR_{12a}$, —$NR_{12}R_{13}$, —$N(R_{20})$—$C_{1-6}$ alkyl—$NR_{12}R_{13}$, —$N(R_{12})COR_{13}$, —$N(R_{20})COOR_{12a}$, —$SO_2NR_{12}R_{13}$, —$N(R_{20})SO_2R_{13a}$, —$N(R_{20})CONR_{12}R_{13}$, —$N(R_{20})C(=NR_{13})NR_{12}R_{13}$, —$N(R_{20})C(=NR_{13})N(SO_2R_{13a})R_{13}$, —$SO_2NHCN$, —$SO_2NHCONR_{12}R_{13}$, aryl, phenyl, $C_{1-6}$ alkyl—$OR_{22}$, —$C_{1-6}$ alkyl —$SR_{22}$, —C(=$NR_{13}$)—, $CSR_{12}$, or —C(=$NR_{13}$)$NR_{12}R_{13}$;

each $R_{12}$ and $R_{13}$ is, independently, H, $OR_{12a}$, $C_{1-6}$ alkyl, $C_{2-6}$ alkenyl, $C_{2-6}$ alkynyl, $C_{2-6}$ alkynyl, $C_{1-6}$ haloalkyl, $C_{1-6}$ perhaloalkyl, $C_{3-8}$ cycloalkyl, aryl, $C_{1-6}$ alkoxy, $C_{2-6}$ alkenyloxy, $C_{2-6}$ alkynyloxy, $C_{1-6}$ haloalkoxy, $C_{1-6}$ perhaloalkoxy, or aralkyl;

each $R_{12a}$ is, independently, H, $C_{1-6}$ alkyl, $C_{2-6}$ alkenyl, $C_{2-6}$ alkynyl, $C_{1-6}$ haloalkyl, $C_{1-8}$ perfluoroalkyl, $C_{3-8}$ cycloalkyl, aryl, or aralkyl;

each $R_{13a}$ is, independently, H, OH, $C_{1-6}$ alkyl, $C_{2-6}$ alkenyl, $C_{2-6}$ alkynyl, $C_{1-6}$ haloalkyl, $C_{1-6}$ perfluoroalkyl, $C_{3-8}$ cycloalkyl, $C_{1-6}$ alkoxy, $C_{2-6}$ alkenyloxy, $C_{2-6}$ alkynyloxy, aryl, or aralkyl;

each $R_{20}$ is independently H or $C_{1-6}$ alkyl;

each $R_{17}$ is, independently, H, $C_{1-6}$ alkyl, $C_{2-6}$ alkenyl, $C_{2-6}$ alkynyl, $C_{1-6}$ haloalkyl, $C_{1-6}$ perhaloalkyl, $C_{3-8}$ cycloalkyl, aryl, or aralkyl;

each $R_{22}$ is independently H or $C_{1-3}$ alkyl;

E is —C═C—;

X is O; and n is 0, 1 or 2.

2. The compound of claim 1 or and an entiomer or diastereomer or a pharmaceutically acceptable salt thereof, wherein at least one of $R_8$ and $R_9$ is other than hydrogen.

3. The compound of claim 1 or and an entiomer or diastereomer or a pharmaceutically acceptable salt thereof, wherein at least one of $R_8$ and $R_9$ is selected from $C_{1-6}$ alkyl, $OR_{17}$, and halogen, wherein said $C_1$-$C_6$ alkyl optionally is substituted with up to four independently selected $R_{14}$ groups.

4. The compound of claim 1 or and an entiomer or diastereomer or a pharmaceutically acceptable salt thereof, wherein at least one of $R_8$ and $R_9$ is selected from methyl, ethyl, $CH_2OH$, OH, and fluorine.

5. The compound of claim 1 or and an entiomer or diastereomer or a pharmaceutically acceptable salt thereof, wherein $R_2$ is hydrogen or $C_1$-$C_6$ alkyl, and $R_4$ and $R_5$ are each hydrogen.

6. The compound of claim 1 or and an entiomer or diastereomer or a pharmaceutically acceptable salt thereof, wherein $R_2$, $R_4$, and $R_5$ are each hydrogen, and $R_3$ is 2- methylquinolin-4-yl.

7. The compound of claim 6 or and an entiomer or diastereomer or a pharmaceutically acceptable salt thereof, wherein the sulfonamide and hydroxamate substituents attached to ring J occupy cis-positions relative to each other.

8. The compound of claim 7 or and an entiomer or diastereomer or a pharmaceutically acceptable salt thereof, wherein at least one of $R_8$ and $R_9$ is selected from $C_{1-6}$ alkyl, $OR_{17}$, and halogen, wherein said $C_1$-$C_6$ alkyl optionally is substituted with up to four independently selected $R_{16}$ groups.

9. The compound of claim 7 or and an entiomer or diastereomer or a pharmaceutically acceptable salt thereof, wherein at least one of $R_8$ and $R_9$ is selected from methyl, ethyl, $CH_2OH$, OH, and fluorine.

10. The compound of claim 1 or and an entiomer or diastereomer or a pharmaceutically acceptable salt thereof, wherein $R_2$ is hydrogen or $C_1$-$C_6$ alkyl.

11. The compound of claim 10 or and an entiomer or diastereomer or a pharmaceutically acceptable salt thereof, wherein the sulfonamide and hydroxamate substituents attached to ring J occupy cis-positions relative to each other.

12. The compound of claim 1 wherein $R_3$ is 2-methylquinolin-4-yl.

13. The compound of claim 1 wherein $R_2$ is hydrogen or methyl, and $R_4$ and $R_5$ are each hydrogen.

14. The compound of claim 1 having the absolute sterochemistry shown in Formula II:

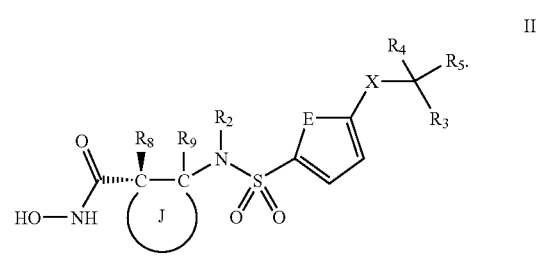

or a pharmaceuticatly acceptable salt thereof.

15. The compound of claim 1 having the absolute stereochemistry shown in Formula III:

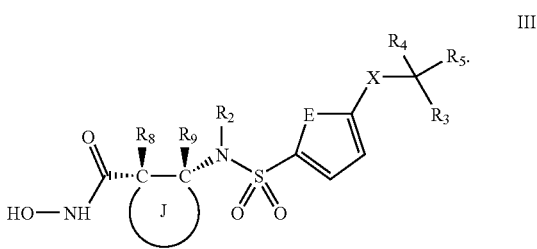

or a pharmaceuticatly acceptable salt thereof.

16. A compound that is selected from:
a) exo-N-Hydroxy-3-[methyl({4-[(2-methylquinolin-4-yl) methoxy]phenyl}sulfonyl)amino]bicyclo[2.2.1]heptane-2-carboxamide;
b) ;
c) ;
d) exo-N-Hydroxy-3-[({4-[(2-methylquinolin-4-yl) methoxy]phenyl}sulfonyl)amino]bicyclo[2.2.1]heptane-2-carboxamide;
e) endo-N-Hydroxy-3-[methyl({4-[(2-methylquinolin-4-yl) methoxy]phenyl}sulfonyl)amino]bicyclo[2.2.1]heptane-2-carboxamide;
f) endo-N-Hydroxy-3-[({4-[(2-methylquinolin-4-yl) methoxy]phenyl}sulfonyl)amino]bicyclo[2.2.1]heptane-2-carboxamide;
g) endo-N-Hydroxy-3-[({4-[(2-methylquinolin-4-yl) methoxy]phenyl}sulfonyl)amino]bicyclo[2.2.1]hept-5-ene-2-carboxamide;

h) endo-N-Hydroxy-3-[methyl({4-[(2-methylquinolin-4-yl) methoxy]phenyl}sulfonyl)amino]bicyclo[2.2.1]hept-5-ene-2-carboxamide;
i) exo-N-Hydroxy-3-[({4-[(2-methylquinolin-4-yl) methoxy]phenyl}sulfonyl)amino]bicyclo[2.2.1]hept-5-ene-2-carboxamide;
j) cis-N-hydroxy-6-[({4-[(2-methylquinolin-4-yl) methoxy]phenyl}sulfonyl)amino]cyclohex-3-ene-1-carboxamide;
k) cis-N-Hydroxy-2-[({4-[(2-methylquinolin-4-yl) methoxy]phenyl}sulfonyl)amino]cyclopentanecarboxamide;
l) cis-N-hydroxy-2-[({4-[(2-methylquinolin-4-yl) methoxy]phenyl}sulfonyl)amino]cyclohexanecarboxamide;
m) (1S,2R)-N-Hydroxy-2-[({4-[(2-methylquinolin-4-yl) methoxy]phenyl}sulfonyl)amino]cyclopentanecarboxamide;
n) trans-N-Hydroxy-2-[({4-[(2-methylquinolin-4-yl) methoxy]phenyl}sulfonyl)amino]cyclohexanecarboxamide;
o) cis-N-Hydroxy-6-[methyl({4-[(2-methylquinolin-4-yl) methoxy]phenyl}sulfonyl)amino]cyclohex-3-ene-1-carboxamide;
p) cis-N-Hydroxy-2-[methyl({4-[(2-methylquinolin-4-yl) methoxy]phenyl}sulfonyl)amino]cyclopentanecarboxamide;
q) (3S,4R)-4-[4-(2-Methyl-quinolin-4-ylmethoxy)-benzenesulfonylamino]tetrahydro-pyran-3-carboxylic acid hydroxyamide;
r) (3S,4R)-4-{Methyl-[4-(2-methyl-quinolin-4-ylmethoxy)-benzenesulfonyl]-amino}- tetrahydro-pyran-3-carboxylic acid hydroxyamide;
s) (3S,4R)-4-[4-(2-Methyl-quinolin-4-ylmethoxy)-benzenesulfonylamino]-tetrahydro-furan-3-carboxylic acid hydroxyamide;
t) (3S,4R)-4-{Methyl-[4-(2-methyl-quinolin-4-ylmethoxy)-benzenesulfonyl]-amino}-tetrahydro-furan-3-carboxylic acid hydroxyamide;
u) (1R,2S,3R,4S)-N-hydroxy-3-(methyl{[4-(2-naphthylmethoxy) phenyl]sulfonyl}amino)bicyclo[2.2.1]heptane-2-carboxamide;
v) (1R,2S,3R,4S)-3-[{[4-(2,1,3-benzoxadiazol-5-ylmethoxy) phenyl]sulfonyl}(methyl)amino]-N-hydroxybicyclo[2.2.1]heptane-2-carboxamide;
w) (1R,2S,3R,4S)-N-hydroxy-3-(methyl{[4-(quinolin-2-ylmethoxy) phenyl]sulfonyl}amino)bicyclo[2.2.1]heptane-2-carboxamide;
x) (1R,2S,3R,4S)-3-[{[4-(1H-benzimidazol-2-ylmethoxy) phenyl]sulfonyl}(methyl)amino]-N-hydroxybicyclo[2.2.1]heptane-2-carboxamide;
y) (1R,2S,3R,4S)-3-[{[4-(1H-1,2,3-benzotriazol-1-ylmethoxy) phenyl]sulfonyl}(methyl)amino]-N-hydroxybicyclo[2.2.1]heptane-2-carboxamide;
z) (3R,4R)-N-hydroxy-3-methyl-4-[({4-[(2-methylquinolin-4-yl) methoxy]phenyl}sulfonyl)amino]tetrahydro-2H-pyran-3-carboxamide;
aa) (3S,4R)-N-hydroxy-3-methyl-4-[({4-[(2-methylquinolin-4-yl) methoxy]phenyl}sulfonyl)amino]tetrahydro-2H-pyran-3-carboxamide;
ab) (1R,2R)-N,1-dihydroxy-2-[({4-[(2-methylquinolin-4-yl) methoxy]phenyl}sulfonyl)amino]cyclopentanecarboxamide;
ac) (1R,2R)-1-fluoro-N-hydroxy-2-[({4-[(2-methylquinolin-4-yl) methoxy]phenyl}sulfonyl)amino]cyclopentanecarboxamide;
ad) (1S,2R)-N-hydroxy-1-methyl-2-[({4-[(2-methylquinolin-4-yl) methoxy]phenyl}sulfonyl)amino]cyclopentanecarboxamide;
ae) (1S,2R)-N-hydroxy-1-ethyl-2-[({4-[(2-methylquinolin-4-yl) methoxy]phenyl}sulfonyl)amino]cyclopentanecarboxamide;
af) (1S ,2R)-N-hydroxy-1-ethyl-2-[methyl({4-[(2-methylquinolin-4-yl) methoxy]phenyl}sulfonyl)amino]cyclopentanecarboxamide;
ag) (1S,2R)-N-hydroxy-1-(hydroxymethyl)-2-[methyl({4-[(2-methylquinolin-4-yl) methoxy] phenyl}sulfonyl)amino]cyclopentanecarboxamide;
ah) (1S,2R)-N-hydroxy-2-methyl-2-[({4-[(2-methylquinolin-4-yl) methoxy]phenyl}sulfonyl)amino]cyclohexanecarboxamide (racemic); and
ai) trans-N-hydroxy-2-[methyl({4-[(2-methylquinolin-4-yl) methoxy]phenyl}sulfonyl)amino]cyclohexanecarboxamide, or a pharmaceuticatly acceptable salt thereof.

17. A composition comprising a compound according to claim 1 or and an entiomer or diastereomer or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO.        : 7,595,327 B2                                           Page 1 of 1
APPLICATION NO.   : 11/377886
DATED             : September 29, 2009
INVENTOR(S)       : Levin et al.

It is certified that error appears in the above-identified patent and that said Letters Patent is hereby corrected as shown below:

On the title page,

[*] Notice:   Subject to any disclaimer, the term of this patent is extended or adjusted under 35 USC 154(b) by 267 days.

Delete the phrase "by 267 days" and insert -- by 382 days --

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,595,327 B2 Page 1 of 1
APPLICATION NO. : 11/377886
DATED : September 29, 2009
INVENTOR(S) : Levin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 497 days.

Signed and Sealed this

Twenty-eighth Day of September, 2010

David J. Kappos
*Director of the United States Patent and Trademark Office*